United States Patent
Gan et al.

(10) Patent No.: US 9,873,889 B2
(45) Date of Patent: Jan. 23, 2018

(54) INCREASING LEAF LONGEVITY AND DISEASE RESISTANCE BY ALTERING SALICYLIC ACID CATABOLISM

(71) Applicant: CORNELL UNIVERSITY, Ithaca, NY (US)

(72) Inventors: Susheng Gan, Ithaca, NY (US); Kewei Zhang, Zhejiang (CN)

(73) Assignee: Cornell University, Ithaca, NY (US)

(*) Notice: Subject to any disclaimer, the term of this patent is extended or adjusted under 35 U.S.C. 154(b) by 0 days.

(21) Appl. No.: 14/909,641

(22) PCT Filed: Aug. 1, 2014

(86) PCT No.: PCT/US2014/049418
§ 371 (c)(1),
(2) Date: Feb. 2, 2016

(87) PCT Pub. No.: WO2015/017786
PCT Pub. Date: Feb. 5, 2015

(65) Prior Publication Data
US 2016/0312239 A1    Oct. 27, 2016

Related U.S. Application Data

(60) Provisional application No. 61/913,691, filed on Dec. 9, 2013, provisional application No. 61/861,858, filed on Aug. 2, 2013.

(51) Int. Cl.
*C12N 15/82* (2006.01)
*C12N 9/02* (2006.01)

(52) U.S. Cl.
CPC ....... *C12N 15/8266* (2013.01); *C12N 9/0073* (2013.01); *C12N 15/8279* (2013.01); *C12N 15/8281* (2013.01); *C12Y 114/13* (2013.01)

(58) Field of Classification Search
None
See application file for complete search history.

(56) References Cited

U.S. PATENT DOCUMENTS

2006/0150283 A1    7/2006    Alexandrov et al.

FOREIGN PATENT DOCUMENTS

| WO | 1998/51801 A1 | 11/1998 |
|---|---|---|
| WO | 2002/10210 A2 | 2/2002 |
| WO | 2003/000898 A1 | 1/2003 |

OTHER PUBLICATIONS

Holton et al, Cloning and expression of flavonol synthase from Petunia hybrid, The Plant Journal, 4 (6), 1003-1010 (1993).*
Blast of SEQ ID No. 1 and alignment of 100% identical hits.*
*Arabidopsis thaliana* proteins containing the consensus sequence of SEQ ID No. 1.*
International Search Report and Written Opinion for corresponding PCT/US2014/049418 (dated Dec. 22, 2014).
Zhang et al., "An Abscisic Acid-AtNAP Transcription Factor-SAG113 Protein Phosphatase 2C Regulatory Chain for Controlling Dehydration in Senescing *Arabidopsis* Leaves," including Supplemental Data, Plant Physiology 158(2): 961-969 (online pub Dec. 19, 2011).
Zhang et al., "Salicylic Acid 3-Hydroxylase Regulates *Arabidopsis* Leaf Longevity by Mediating Salicylic Acid Catabolism," including Supporting Information, Proc Natl Acad Sci USA 110(36): 14807-14812 (Epub Aug. 19, 2013).

* cited by examiner

*Primary Examiner* — Eileen B O Hara
(74) *Attorney, Agent, or Firm* — LeClairRyan, a Professional Corporation

(57) ABSTRACT

The present invention relates to a transgenic plant having an altered level of salicylic acid 3-hydroxylase ("S3H") protein, compared to that of a non-transgenic plant, where the transgenic plant displays an altered leaf senescence phenotype, relative to a non-transgenic plant. The present invention relates to a mutant plant comprising an inactivated gene encoding S3H protein, where the mutant plant displays a premature or precocious leaf senescence phenotype, relative to a non-mutant plant. The present invention also relates to methods for promoting premature or precocious leaf senescence in a plant, delaying leaf senescence in a plant, and making a mutant plant having a decreased level of S3H protein compared to that of a non-mutant plant, where the mutant plant displays a premature or precocious leaf senescence phenotype relative to a non-mutant plant. The present invention also relates to inducing or promoting pathogen resistance in plants.

13 Claims, 15 Drawing Sheets

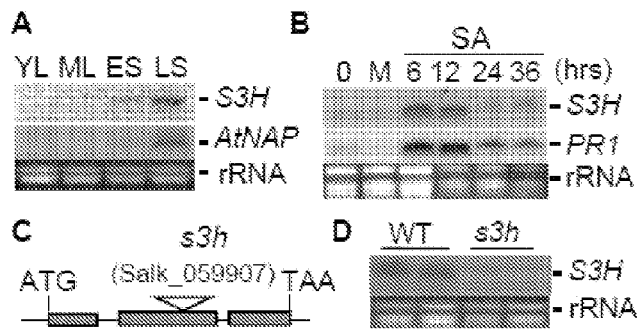

FIGS. 1A-1D

Primers used in this research

| | Primer name | Primer sequences (5'→3') | Engineered restriction site (underlined) | Purpose |
|---|---|---|---|---|
| SEQ ID NO: 32 | G2563 | ACTAGTATGGCAACTTCTGCAATATC | HindIII | For characterization of T-DNA lines and construction of over-expression vector |
| SEQ ID NO: 33 | G2564 | CTGCAGTTAGGTTGTTGGAGCTTTGA | PstI | |
| SEQ ID NO: 34 | G2325 | TGGTTCACGTAGTGGGCCATCG | | T-DNA border (LB1) for mutant characterization |
| SEQ ID NO: 35 | S3H_BamHI | AACGGATCCATGGCAACTTCTGCAATATC | BamHI | For construction of His-tagged S3H protein expression |
| SEQ ID NO: 36 | S3H_HindIII | GGCAAGCTTTTAGGTTGTTGGAGCTTTGA | HindIII | |
| SEQ ID NO: 37 | G3149 | CGTAAAGCATCAACGAAACG | | For making AtNAP probe for RNA gel blot analysis |
| SEQ ID NO: 38 | G3150 | TCATGTACCCAAAACTAACCA | | |
| SEQ ID NO: 39 | G10 | CAGCTGCGGATGTTCTTG | | For making SAG13 probe for RNA gel blot analysis |
| SEQ ID NO: 40 | G246 | CCACTTTCTCCCCATTTTG | | |
| SEQ ID NO: 41 | G9 | GCAACCAAAGGAGCCATG | | For making SAG13 probe for RNA gel blot analysis |
| SEQ ID NO: 42 | G16 | GTTTGGCCAACTAGTCTGC | | |
| SEQ ID NO: 43 | EDS1F | GGATACAAGATGAATACAAGCC | | For making EDS1 probe for RNA gel blot analysis |
| SEQ ID NO: 44 | EDS1R | ACCTAAGGTTCAGGTATCTGT | | |
| SEQ ID NO: 45 | PAD4F | ATGGACGATTGTCGATTCGAG | | For making PAD4 probe for RNA gel blot analysis |
| SEQ ID NO: 46 | PAD4R | CTAAGTCTCCATTGCGTCACT | | |
| SEQ ID NO: 47 | PR1F | TGGCTATTCTCGATTTTTAATCG | | For making PR1 probe for RNA gel blot analysis |
| SEQ ID NO: 48 | PR1R | CCATTGCACGTGTTCGCAG | | |

FIG. 1E

Analysis of metabolites SA, 2,3-DHBA, 2,5-DHBA and their sugar conjugates in young and senescing rosette leaves[a]

| Genotypes | Free acids (μg/g FW) | | | Xyloside derivatives (μg/g FW) | | | Glucoside derivatives (μg/g FW) | | |
|---|---|---|---|---|---|---|---|---|---|
| | SA | 2,3-DHBA | 2,5-DHBA | SAX | 2,3-DHBX | 2,5-DHBX | SAG | 2,3-DHBG | 2,5-DHBG |
| WT(Y) | 0.08 ± 0.02 | n.d. | n.d. | n.d. | 17.32 ± 1.64 | 14.74 ± 1.05 | 0.33 ± 0.04 | 2.06 ± 0.18 | 0.20 ± 0.07 |
| s3h(Y) | 0.50 ± 0.08* | n.d. | n.d. | n.d. | n.d. | 16.52 ± 0.92 | 0.88 ± 0.12* | n.d. | 0.40 ± 0.11 |
| S3HOE1(Y) | 0.01 ± 0.00* | n.d. | n.d. | n.d. | 34.14 ± 4.66* | 6.34 ± 1.26* | n.d. | 2.11 ± 0.35 | 0.03 ± 0.03* |
| WT(S) | 0.40 ± 0.1 | n.d. | n.d. | n.d. | 41.44 ± 4.90 | 36.35 ± 3.11 | 0.52 ± 0.09 | 3.87 ± 0.51 | 1.24 ± 0.10 |
| s3h(S) | 2.84 ± 0.42* | n.d. | n.d. | n.d. | n.d. | 58.00 ± 5.31* | 1.65 ± 0.09* | n.d. | 3.00 ± 0.30* |
| S3HOE1(S) | 0.04 ± 0.02* | n.d. | n.d. | n.d. | 92.18 ± 9.80* | 14.79 ± 1.78* | n.d. | 9.40 ± 1.71* | 0.18 ± 0.08* | a. The data represent the means ± SE of five to six replications. Y, rosette leaves from 25-DAG plants; S, rosette leaves from 35-DAG plants. FW, fresh weight. * Student's t-test, p<0.01, represents significant difference between wild type and s3h mutant or wild type and S3HOE1. n.d., not detectable. SA, salicylic acid; 2,3-DHBA, 2,3-dihydroxybenzoic acid; 2,5-DHBA, 2,5-dihydroxybenzoic acid; SAX, SA xyloside; 2,3-DHBX, 2,3-DHBA xyloside; 2,5-DHBX, 2,5-DHBA xyloside; SAG, SA glucoside; 2,3-DHBG, 2,3-DHBA glucoside; 2,5-DHBG, 2,5-DHBA glucoside.

INCREASING LEAF LONGEVITY AND DISEASE RESISTANCE BY ALTERING SALICYLIC ACID CATABOLISM

This application is a national stage application under 35 U.S.C. §371 of PCT Application No. PCT/US2014/049418, filed Aug. 1, 2014, which claims the benefit of U.S. Provisional Patent Application Ser. No. 61/861,858, filed Aug. 2, 2013, and U.S. Provisional Application Ser. No. 61/913,691, filed Dec. 9, 2013, each of which is hereby incorporated by reference in its entirety.

This invention was made with government support under grant number DE-FG02ER15341 awarded by the Department of Energy, and NSF-MCB-0445596 awarded by the National Science Foundation. The government has certain rights in this invention.

FIELD OF THE INVENTION

The present invention relates generally to control of plant lifecycle and disease resistance, as well as compositions and methods relating to the same.

BACKGROUND OF THE INVENTION

Salicylic acid ("SA") (2-hydroxy benzoic acid), a phenolic compound, has been studied for its medicinal use in humans for more than 200 years (Vlot et al., "Salicylic Acid, a Multifaceted Hormone to Combat Disease," *Annu. Rev. Phytopathol.* 47:177-206 (2009)) and its role as a plant hormone in disease resistance, leaf senescence, flowering and thermogenesis have also more recently been investigated (Vlot et al., "Salicylic Acid, a Multifaceted Hormone to Combat Disease," *Annu. Rev. Phytopathol.* 47:177-206 (2009) and Raskin, "Role of Salicylic Acid in Plants," *Annu. Rev. Plant Physiol. Plant Mol. Biol.* 43:439-463 (1992)). The roles of SA in plant defense and the hypersensitive response (a fast form of programmed cell death or PCD) have been intensively investigated (Vlot et al., "Salicylic Acid, a Multifaceted Hormone to Combat Disease," *Annu. Rev. Phytopathol.* 47:177-206 (2009) and Raskin, "Role of Salicylic Acid in Plants," *Annu. Rev. Plant Physiol. Plant Mol. Biol.* 43:439-463 (1992)). Leaf senescence is a slow form of programmed cell death that allows plants to mobilize nutrients released from senescing cells to seeds, storage organs or actively growing tissues (Zhang et al., "An ABA-Regulated and Golgi-Localized Protein Phosphatase Controls Water Loss During Leaf Senescence in *Arabidopsis*," *Plant J.* 69(4):667-678 (2012) and Gan & Amasino, "Making Sense of Senescence: Molecular Genetic Regulation and Manipulation of Leaf Senescence," *Plant Physiol* 113(2): 313-319 (1997)). Although the role of SA in leaf senescence and its underlying molecular mechanism have been less studied, there is some evidence that both disease defense and leaf senescence seem to share some components in SA signaling and regulation (Love et al., "Timing Is Everything: Regulatory Overlap in Plant Cell Death," *Trends Plant Sci.* 13(11):589-595 (2008) and Rivas-San Vicente & Plasencia, "Salicylic Acid Beyond Defence: Its Role in Plant Growth and Development," *J. Exp. Bot.* 62(10):3321-3338 (2011)).

Much research has been carried out on SA biosynthesis. There are two SA biosynthetic pathways in plants: the phenylalanine ammonia lyase (PAL) pathway and the isochorismate (IC) pathway; both pathways use the primary metabolite chorismate (Dempsey et al., "Salicylic Acid Biosynthesis and Metabolism," *Arabidopsis Book* 9:e0156 (2011)). The chorismate-derived L-phenylalanine can be converted into SA via either benzoate intermediates or coumaric acid through a series of enzymatic reactions involving PAL, benzoic acid 2-hydroxylase (BA2H) and other uncharacterized enzymes (Leon et al., "Benzoic Acid 2-Hydroxylase, a Soluble Oxygenase From Tobacco, Catalyzes Salicylic Acid Biosynthesis," *Proc. Nat'l Acad. Sci. U.S.A.* 92(22):10413-10417 (1995)). Chorismate can also be converted to SA via isochorismate in a two-step process involving isochorismate synthase (ICS) and isochorismate pyruvate lyase (IPL). In *Arabidopsis*, two ICS enzymes, which convert chorismate to isochorimate, have been identified; the IC pathway contributes approximately 90% of the SA production induced by pathogens and UV light (Wildermuth et al., "Isochorismate Synthase Is Required to Synthesize Salicylic Acid for Plant Defence," *Nature* 414(6863): 562-565 (2001) and Garcion et al., "Characterization and Biological Function of the ISOCHORISMATE SYNTHASE2 Gene of *Arabidopsis*," *Plant Physiol.* 147(3): 1279-1287 (2008)).

In plants, SA may undergo biologically relevant chemical modifications such as glucosylation, methylation and amino acid (AA) conjugation (Dempsey et al., "Salicylic Acid Biosynthesis and Metabolism," *Arabidopsis Book* 9:e0156 (2011)). SA has been shown to be converted to SA sugar conjugates SA O-β-glucoside (SAG) and salicyloyl glucose ester (SGE) by SA glucosyltransferases (SAGT) (Lim et al., "The Activity of *Arabidopsis* Glycosyltransferases Toward Salicylic Acid, 4-Hydroxybenzoic Acid, and Other Benzoates," *J. Biol. Chem.* 277(1):586-592 (2002) and Dean & Delaney, "Metabolism of Salicylic Acid in Wild-Type, ugt74f1 and ugt74f2 Glucosyltransferase Mutants of *Arabidopsis thaliana*," *Physiol. Plant* 132(4):417-425 (2008)).

The SA glycosides are actively transported from the cytosol to the vacuole as an inactive storage form that can later be converted back to SA (Dean et al., "The Formation, Vacuolar Localization, and Tonoplast Transport of Salicylic Acid Glucose Conjugates in Tobacco Cell Suspension Cultures," *Planta* 221(2):287-296 (2005)). Methylation inactivates SA but increases SA's membrane permeability and volatility, thus allows more effective long distance transport of this defense signal (Park et al., "Methyl Salicylate Is a Critical Mobile Signal for Plant Systemic Acquired Resistance," *Science* 318(5847):113-116 (2007)). AA conjugation of SA at trace levels was found in infected *Arabidopsis* plants (Zhang et al., "Dual Regulation Role of GH3.5 in Salicylic Acid and Auxin Signaling During *Arabidopsis*-*Pseudomonas syringae* Interaction," *Plant Physiol.* 145(2): 450-464 (2007)). Recently, high levels of 2,3- and 2,5-dihydroxybenzoic acid (2,3-DHBA and 2,5-DHBA, respectively) sugar conjugates were detected in infected or aged *Arabidopsis* leaves, and they appeared to be the major inactive form of SA (Bartsch et al., "Accumulation of Isochorismate-Derived 2,3-Dihydroxybenzoic 3-O-beta-D-Xyloside in *Arabidopsis* Resistance to Pathogens and Ageing of Leaves," *J. Biol. Chem.* 285(33):25654-25665 (2010)). SA in transgenic *Arabidopsis* plants expressing a bacterial salicylate hydroxylase (encoded by NahG) was shown to be converted to catechol; the NahG transgenic plants have thus been useful in plant defense and senescence studies involving SA (Friedrich et al., "Characterization of Tobacco Plants Expressing a Bacterial Salicylate Hydroxylase Gene," *Plant Mol. Biol.* 29(5):959-968 (1995) and Yamamoto et al., "Salicylate Hydroxylase, a Monooxygenase Requiring Flavin Adenine Dinucleotide: I. Purification and General Properties," *J. Biol. Chem.* 240(8):3408-3413 (1965)). However, the enzyme(s), presumably SA hydroxylases, responsible for the formation of 2,3- and 2,5-DHBA have yet to be identified in plants.

The present invention is directed to overcoming these and other deficiencies in the art.

SUMMARY OF THE INVENTION

One aspect of the present invention relates to a transgenic plant having an altered level of salicylic acid 3-hydroxylase ("S3H") protein, compared to that of a non-transgenic plant, where the transgenic plant displays an altered leaf senescence phenotype, relative to a non-transgenic plant.

Another aspect of the present invention relates to a mutant plant comprising an inactivated gene encoding S3H protein, where the mutant plant displays a premature or precocious leaf senescence phenotype, relative to a non-mutant plant.

Yet another aspect of the present invention relates to a method for promoting premature or precocious leaf senescence in a plant. This methods involves providing a transgenic plant or plant seed transformed with a nucleic acid construct effective in silencing expression of a S3H protein capable of causing leaf senescence in a plant; and growing the transgenic plant or the plant grown from the transgenic plant seed under conditions effective to promote premature or precocious leaf senescence in the transgenic plant or the plant grown from the transgenic plant seed.

Another aspect of the present invention relates to a method for delaying leaf senescence in a plant. This method involves transforming a plant cell with a nucleic acid molecule encoding a S3H capable of causing leaf senescence in a plant operably associated with a promoter to obtain a transformed plant cell, where expression of the nucleic acid molecule in the plant cell causes delayed leaf senescence; and regenerating a plant from the transformed plant cell under conditions effective to delay leaf senescence in the plant.

Another aspect of the present invention relates to a method of making a mutant plant having a decreased level of S3H protein compared to that of a non-mutant plant, where the mutant plant displays a premature or precocious leaf senescence phenotype relative to a non-mutant plant. This method involves providing at least one cell of a non-mutant plant containing a gene encoding a functional S3H protein and treating the at least one cell of a non-mutant plant under conditions effective to inactivate said gene, thereby yielding at least one mutant plant cell containing an inactivated S3H protein encoding gene. This method also involves propagating the at least one mutant plant cell into a mutant plant, where the mutant plant has a decreased level of S3H protein compared to that of the non-mutant plant and displays a premature or precocious leaf senescence phenotype relative to a non-mutant plant.

Another aspect of the present invention relates to a method of inducing or promoting pathogen resistance in plants. This method involves providing a transgenic plant or plant seed transformed with a nucleic acid construct effective in silencing expression of a salicylic acid 3-hydroxylase protein capable of causing leaf senescence in a plant; and growing the transgenic plant or the plant grown from the transgenic plant seed under conditions effective to induce or promote pathogen resistance in the transgenic plant or the plant grown from the transgenic plant seed.

The plant hormone SA plays critical roles in plant defense, stress responses and senescence. While the SA biosynthesis is well understood, the pathways by which SA is catabolized remains elusive.

Described herein is the characterization of a novel SA 3-hydroxylase ("S3H") that converts SA to 2,3-DHBA, a precursor of SA's major storage form 2,3-DHBA sugar conjugates, and plays a pivotal role in SA catabolism and homeostasis and in regulation of leaf senescence. S3H is senescence associated and is inducible by SA, and is thus a key part of a negative feedback regulation system of SA levels during senescence. The enzyme converts SA (with a $K_m$ 58.29 µM) to both 2,3-dihydroxybenzoic acid (2,3-DHBA) and 2,5-DHBA in vitro but only 2,3-DHBA in vivo. The s3h knockout mutants fail to produce 2,3-DHBA sugar conjugates, accumulate very high levels of SA and its sugar conjugates, and exhibit a precocious senescence phenotype. Conversely, the gain-of-function lines contain high levels of 2,3-DHBA sugar conjugates, extremely low levels of SA and its sugar conjugates, and display a significantly extended leaf longevity. This research reveals an elegant SA catabolic mechanism by which plants regulate SA levels by converting it to 2,3-DHBA to prevent SA over-accumulation. The research also provides strong molecular genetic evidence for an important role of SA in regulating the onset and rate of leaf senescence. The control of leaf senescence is a significant advance and permits the control and enhancement of crop productivity and quality. For instance, delay of leaf senescence may have certain agricultural benefits, including, but not limited to, increase in grain yield and biomass, improvement in horticultural performance, and/or enhanced tolerance to drought stress. In addition, the Examples herein describe results indicating that S3H has a role in plant defense.

BRIEF DESCRIPTION OF THE DRAWINGS

FIGS. 1A-1E show experimental results demonstrating senescence-associated and SA-induced expression of S3H in WT and in a T-DNA insertion line. FIG. 1A shows results demonstrating S3H was expressed during leaf senescence. YL, young leaves, ML, mature leaves, ES, early senescence leaves; LS, late senescence leaves. AtNAP, a senescence maker gene, was used as a positive control. FIG. 1B shows experimental results demonstrating that S3H was induced by SA. The SA-inducible gene PR1 served as a positive control. 0, leaves without treatment. M, leaves treated with mock solution for 36 hrs. FIG. 1C is an illustration of T-DNA insertions in line SALK_059907. FIG. 1D shows the characterization of T-DNA insertion line of FIG. 1C by RNA gel blot analysis of S3H expression in the early senescence leaves of wild type (WT) and the s3h mutant plants (s3h). Two independently isolated RNA samples were used. FIG. 1E is a table showing the primers used in the studies described herein.

FIG. 2A is an image of s3h null mutant (right) exhibited an accelerated leaf senescence phenotype compared to WT (left) at 35 DAG. FIG. 2B is a graph of experimental results relating to chlorophyll contents in the $5^{th}$ to $10^{th}$ leaves (counted from bottom to top with the $1^{st}$ the oldest) of WT and s3h mutant shown in FIG. 2A (bars show SE, n=6). FIG. 2C is a graph of experimental results $F_v/F_m$ ratios of leaves of WT and s3h mutant shown in in FIG. 2A (bars show SE, n=6). FIG. 2D shows experimental results demonstrating S3H overexpression line 1 (S3HOE1, right) displayed a remarkably delayed leaf senescence phenotype compared with that of WT at 45 DAG. FIG. 2E is a graph of experimental results relating to chlorophyll contents of the $5^{th}$ to $10^{th}$ leaves from WT and S3HOE1 plant in FIG.

2D. Bars are SE, n=6. (F) $F_v/F_m$ ratios of leaves of WT and S3HOE1 shown in FIG. 2A. Bars show SE, n=6. FIG. 2G is a graph of experimental results showing altered onset and pace of leaf senescence in s3h and S3HOE1 plants compared with those of WT. The bottom section of each bar indicates days from leaf emergence to the onset of senescence (visible yellowing at the leaf tip). The top section of each bar indicates the time period (days) it takes for senescence to progress from the first visible yellowing at the leaf tip to the leaf petiole. The $6^{th}$ rosette leaves were used for the assay. Bars show SE, n=6. FIG. 2H is a graph showing the survival curve of WT, s3h mutant and S3HOE1 transgenic plant. Bars show SE, n=16.

FIG. 3A includes images showing phenotypes of s3h mutant, WT, and S3HOE plants at different ages (DAG, days after germination). FIG. 3B includes images of RNA gel blot analyses of expression of senescence-associated genes (SAG12 and SAG13) and SA responsive genes (EDS1, PAD4 and PR1) in leaves of WT, s3h and S3HOE1 plants at 25, 30, 35 and 40 DAG, respectively. All rosette leaves from two plants at each time point were harvested for RNA extraction.

FIGS. 4A-4H show experimental results relating to conversion of SA to 2,3-DHBA and 2,5-DHBA by recombinant S3H enzyme in vitro. FIG. 4A is a schematic showing the biochemical reaction catalyzed by recombinant S3H in vitro. FIG. 4B is a graph showing HPLC profiles of 30-min reaction of the recombinant S3H protein and empty vector extracts (Ev) incubated with SA. The authentic 2,3-DHBA and 2,5-DHBA were used as standards. FIG. 4C is a graph showing that the UV spectra of the enzymatic product 2,3-DHBA is identical to that of the 2,3-DHBA standard. FIG. 4D is a graph showing that the UV spectra of the enzymatic product 2,5-DHBA is identical to that of the 2,5-DHBA standard. The S3H enzymatic products 2,3-DHBA and 2,5-DHBA also have the same tandem ESI-mass spectra MS (as shown in FIG. 4E) and MS2 (as shown in FIG. 4F), respectively. FIG. 4G is a graph of experimental results showing the kinetics of the recombinant S3H (SA as the substrate). The mean and SE are shown, n=4. The metabolite profiles of SA in young and senescing plants of WT, s3h and S3HOE lines were analyzed using LC-MS/MS. The levels of free SA, SA sugar conjugates, SA derivatives including 2,3-DHBA, 2,5-DHBA and their sugar conjugates are summarized in FIG. 4H.

FIG. 6A is an image of an s3h knockout mutant has normal bolting time and did not show any difference to WT at 25 days after germination (DAG). FIG. 6B is an image of an s3h mutant showing a significantly accelerated leaf senescence phenotype at 42 DAG (the shoots were removed for better observation). FIG. 6C is an image showing the accelerated leaf senescence phenotype in s3h is restored by the S3H genomic fragment. The pGL3228 represent the complementary construct containing the intact S3H genomic DNA including its promoter region.

DETAILED DESCRIPTION OF THE INVENTION

Figures 2A, 2B, 2C, 2D, 2E, 2F, 2G, 2H:
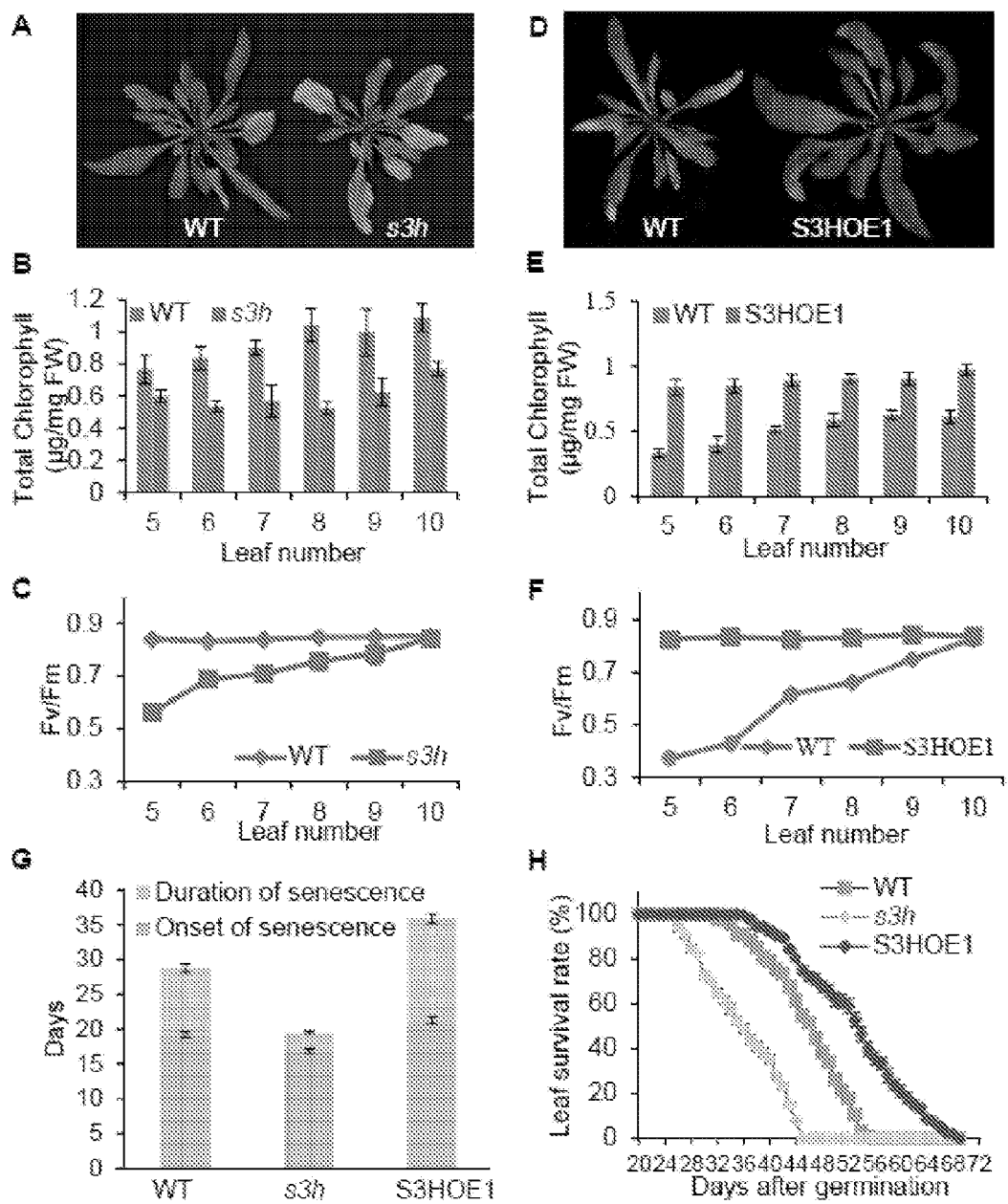
FIGS. 2A-2H show experimental results relating to phenotypic analysis of s3h knockout and S3H overexpression lines.

One aspect of the present invention relates to transgenic plant having an altered level of salicylic acid 3-hydroxylase ("53H") protein, compared to that of a non-transgenic plant, where the transgenic plant displays an altered leaf senescence phenotype, relative to a non-transgenic plant.

Nucleic acid molecules encoding S3H, as well as corresponding S3H amino acid sequences, each of which may be used in accordance with the present invention include those from a plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, *sorghum*, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca, Populus trichocarpa*, and *zinnia*.

In one embodiment, SH3 includes the amino acid sequence of NxYPxCPxPxLxxGxxxHxDxxxxTxLLQD (SEQ ID NO: 1), where x is any amino acid. SEQ ID NO:1 is a consensus sequence of those S3H amino acid sequences aligned in FIG. 14. In one embodiment, nucleic acid molecules encoding S3H, as well as corresponding S3H amino acid sequences, include those from *Arabidopsis thaliana, Populus trichocarpa, Zea mays, Sorghum bicolor, Oryza sativa* (rice), *Hordeum vulgare* (common barley), *Triticum aestivum* (wheat), *Nicotiana tabacum, petunia, Glycine max* (Soybean), cotton, *Malus domestica* (Apple), *Brassica napus, Solanum tuberosum* (Potato), or *Solanum lycopersicum* (Tomato). Such nucleic acid molecules and amino acid sequences include the following:

```
Arabidopsis thaliana S3H coding cDNA sequence
(SEQ ID NO: 2):
ATGGCAACTTCTGCAATATCTAAGCTCTTAGTGTCTGATTTCGCCTCCTC
CGTTCACATCCCTTCAAACTATGTCCGACCAATCTCCGACCGTCCGAACT
TGTCCGAGGTCGAGAGTTCTGGCGATTCCATCCCTCTGATCGATCTCCGG
GACCTCCATGGACCTAATCGAGCCGTAATTGTCCAACAACTTGCTAGTGC
GTGTTCCACTTATGGTTTCTTTCAGATCAAGAATCATGGAGTACCAGATA
CAACCGTCAATAAAATGCAAACCGTTGCGAGAGAGTTCTTCCATCAACCC
GAGAGCGAAAGAGTCAAACACTACTCCGCAGATCCAACAAAGACAACGAG
ACTCTCCACCAGTTTCAACGTCGGCGCAGACAAAGTCTTGAACTGGAGAG
ACTTCCTTAGACTCCATTGCTTTCCCATAGAAGATTTCATCGAAGAATGG
CCATCTAGTCCCATCTCTTTCAGAGAAGTCACAGCTGAATATGCCACGAG
CGTAAGAGCTTTGGTTTTGAGACTTCTTGAGGCCATCTCAGAGAGTTTAG
GCCTTGAAAGCGACCATATAAGCAATATATTAGGCAAACACGCTCAACAC
ATGGCGTTTAACTACTATCCGCCGTGTCCAGAACCCGAGCTAACTTACGG
ACTTCCCGGACATAAAGACCCAACCGTTATCACTGTCCTTCTTCAAGACC
AAGTCTCTGGTTTGCAAGTCTTTAAGGATGATAAATGGGTCGCTGTTAGT
CCAATTCCCAACACTTTCATCGTCAATATCGGCGACCAAATGCAGGTCAT
AAGCAATGATAAATACAAGAGTGTGCTCCATAGAGCCGTAGTAAACACCG
AGAACGAGCGGTTATCGATTCCGACTTTCTATTTCCCTTCAACAGATGCA
GTGATTGGTCCAGCACACGAGCTGGTCAATGAACAAGACTCTCTTGCCAT
TTACAGAACCTACCCGTTTGTTGAGTATTGGGACAAGTTTTGGAACAGAT
CACTTGCTACTGCGAGCTGTCTAGACGCCTTCAAAGCTCCAACAACCTAA
Arabidopsis thaliana S3H protein sequence
(SEQ ID NO: 3):
MATSAISKLLVSDFASSVHIPSNYVRPISDRPNLSEVESSGDSIPLIDLR
DLHGPNRAVIVQQLASACSTYGFFQIKNHGVPDTTVNKMQTVAREFFHQP
ESERVKHYSADPTKTTRLSTSFNVGADKVLNWRDFLRLHCFPIEDFIEEW
PSSPISFREVTAEYATSVRALVLRLLEAISESLGLESDHISNILGKHAQH
MAFNYYPPCPEPELTYGLPGHKDPTVITVLLQDQVSGLQVFKDDKWVAVS
PIPNTFIVNIGDQMQVISNDKYKSVLHRAVVNTENERLSIPTFYFPSTDA
VIGPAHELVNEQDSLAIYRTYPFVEYWDKFWNRSLATASCLDAFKAPTT
Populus trichocarpa S3H homologous coding cDNA
sequence (SEQ ID NO: 4):
ATGGCTCCCACCGCCAAGCTACTACTAGCCGACCTTGCATCTTCAGGTGT
AAAACAAATTCCTTCCAACTTCATCCGTCCCATCTCCGACCGTCCGAATC
TCTCCGATGTTCAGATTTCGGATGGCTCGATTCCTCTAATTGACCTTCGT
GGCCTTGATGGTCCCAACCACTCTACTATAATCGAACAAATTGGCCAAGC
ATGCCAAAGGGATGGGTTCTTTCAGGTGAAGAATCATGGGATACCAGAGG
AAATGATCAGTATCATACTAAACATAGCTAGACAGTTCTTCAAATTGCCT
GAAAGTGAAAGGTTAAAAAATTACTCTGACGATCCCACTAAGACAACCAG
GTTGTCTACTAGTTTCAATATTAAGACAGAACAAGTTTCAAGCTGGAGAG
ATTTCTTGAGACTTCATTGTTATCCTCTCGAAGATTACGTACATGAATGG
CCTAGCAATCCTCCATCATTCAGGAAAGATGTGGCTGAATATTGCACAAG
TGTTAGAGGTCTAGTGTTGAGACTGCTTGAGGCCATATCCGAGAGCTTGG
GTTTGGAAAGAGACTATATTGATAAGAAATTAGGCGGGCATGGACAACAT
```

```
ATGGCTATGAACTACTATCCACCCTGTCCACAGCCAGAACTCACATATGG

ATTGCCTGGACACACCGACCCTAATTTAATCACCATCCTGTTACAAGATC

ACGTGCCTGGATTGCAGGTTCTAAGAAATGGCAAGTGGATTGCTGTGAAT

CCGATTCCCAATACTTTCATCGTCAACATCGGTGATCAAATGCAGGTACT

TAGCAATGATCGTTACAAGAGTGTGCTTCACCGAGCAGTTGTGAACAGTG

ATAAAGACCGAATATCTATACCGACGTTCTACTGTCCTTCACCGGATGCT

GTAATCGGGCCTCCAAAGGAGCTAGTCGACGACGAGCATCCTGCCGTCTA

TAGAGATTTTACGTACGGTGAATACTATGAGAAGTTTTGGAACAAGGGAC

TTGTAAAAGAATGTTGCTTGGACTTGTTCAAGCCTTCTAATAATACAACC

TAG
```

Populus trichocarpa S3H homologous protein
sequence (SEQ ID NO: 5):
MAPTAKLLLADLASSGVKQIPSNFIRPISDRPNLSDVQISDGSIPLIDLR
GLDGPNHSTIIEQIGQACQRDGFFQVKNHGIPEEMISIILNIARQFFKLP
ESERLKNYSDDPTKTTRLSTSFNIKTEQVSSWRDFLRLHCYPLEDYVHEW
PSNPPSFRKDVAEYCTSVRGLVLRLLEAISESLGLERDYIDKKLGGHGQH
MAMNYYPPCPQPELTYGLPGHTDPNLITILLQDHVPGLQVLRNGKWIAVN
PIPNTFIVNIGDQMQVLSNDRYKSVLHRAVVNSDKDRISIPTFYCPSPDA
VIGPPKELVDDEHPAVYRDFTYGEYYEKFWNKGLVKECCLDLFKPSNNTT Zea mays S3H homologous coding cDNA sequence
(SEQ ID NO: 6):
```
ATGGCCCCAGCCATTTCCAAGCCTCTCCTTACCGATCTCGTTGCACAGAT

CGGGAAGGTCCCATCGAGCCACATCAGGCCTGTCGGAGACCGCCCGGACC

TCGCCAATGTCGACAACGAGTCCGGCGCCGGGATCCCGCTCATCGACCTC

AAGAAGCTCAACGGCCCGGAGCGCCGTAAGGTGGTGGAGGCCATCGGCAA

GGCCTGCGAATCCGACGGCTTCTTCATGGTGACGAACCACGGCATCCCGG

CGGCGGTCGTGGAGGGCATGCTGCGCGTGGCGCGGGAGTTCTTCCACCTG

CCGGAGTCGGAGCGGCTCAAGTGCTACTCCGACGACCCCAACAAGGCGAT

CCGGCTGTCCACCAGCTTCAACGTGCGCACGGAGAAGGTCAGCAACTGGC

GCGACTTCCTGCGCCTGCATTGCTACCCCCTCCAGAGCTTCGTCGACCAG

TGGCCGTCAAACCCGCCGTCCTTCAGGCAAGTGGTGGGCACCTACGCGAC

GGAGGCCAGGGCGCTGGCGCTGAGGCTGCTGGAGGCCATATCGGAGAGCC

TGGGCCTGGAGCGGAGCCACATGGTGGCGGCCATGGGGAGGCACGCGCAG

CACATGGCGGTGAACTACTACCCGCCGTGCCCGCAGCCGGAGCTCACCTA

CGGGCTGCCGGGCCACAAGGACCCCAATGCCATCACGCTGCTGCTGCAGG

ACGGCGTCTCCGGCCTCCAGGTGCAGCGTGGCGGCCGCTGGGTGGCCGTC

AACCCCGTGCCCAACGCGCTGGTCATCAACATCGGAGACCAGATGCAGGC

ACTGAGCAACGACCGGTACAAGAGCGTGCTCCACCGCGTGATCGTCAACA

GCGAGAGCGAGCGGATCTCGGTGCCGACGTTCTACTGCCCGTCCCCGGAC

GCGGTGATCGCGCCGGCCGACGCGCTGGTGGACGACGGCCACCCTCTGGC

CTACCGCCCCTTCACTTACCAGGAGTACTACGACGCGTTCTGGAACATGG

GCCTCCAGTCGGCCAGCTGCCTCGACCGGTTTAGGCCCGGAGGATCGTTG
```
GAGTGA
```

Zea mays S3H homologous protein sequence
(SEQ ID NO: 7):
MAPAISKPLLTDLVAQIGKVPSSHIRPVGDRPDLANVDNESGAGIPLIDL
KKLNGPERRKVVEAIGKACESDGFFMVTNHGIPAAVVEGMLRVAREFFHL
PESERLKCYSDDPNKAIRLSTSFNVRTEKVSNWRDFLRLHCYPLQSFVDQ
WPSNPPSFRQVVGTYATEARALALRLLEAISESLGLERSHMVAAMGRHAQ
HMAVNYYPPCPQPELTYGLPGHKDPNAITLLLQDGVSGLQVQRGGRWVAV
NPVPNALVINIGDQMQALSNDRYKSVLHRVIVNSESERISVPTFYCPSPD
AVIAPADALVDDGHPLAYRPFTYQEYYDAFWNMGLQSASCLDRFRPGGSL
E Sorghum bicolor S3H homologous coding cDNA
sequence (SEQ ID NO: 8):
```
ATGGCCCCAGCCATTTCCAAGCCTCTCCTCAGCGATCTCGTGGCACAGAT

CGGGAAAGTCCCATCGAGCCACATCAGGCCTGTGGGAGACCGCCCGGACC

TCGCCAATGTCGACAACGAGTCCGGCGCCGGGATCCCGCTCATCGACCTC

AAGATGCTCAACGGGCCGGAGCGCCGTAAGGTGGTGGAGGCCATCGGCAG

GGCCTGCGAATCCGACGGCTTCTTCATGGTGACGAACCACGGCATCCCGG

CGGCGGTGGTGGAGGGGATGCTGCGCGTGGCGAGGGAGTTCTTCCACCTG

CCGGAGTCGGAGCGGCTCAAGTGCTACTCCGACGACCCCAAGAAGGCGAT

CCGGCTGTCCACCAGCTTCAACGTGCGCACGGAGAAGGTGAACAACTGGC

GCGACTTCCTGCGCCTGCATTGCTACCCGCTCGAGAGCTTCGTCGACCAG

TGGCCGTCAAACCCGCCATCCTTCAGGCAAGTGGTGGGCACCTACGCGAC

GGAAGCGAGGGCGCTAGCGCTGAGGCTGCTGGAGGCCATATCGGAGAGCC

TGGGCCTGGAGCGGAGCCACATGGTGCGCGCCATGGGGAGGCACGCGCAG

CACATGGCGGTGAACTACTACCCGCCGTGCCCGCAGCCGGAGCTCACCTA

CGGGCTGCCGGGCCACAAGGACCCCAATGCCATCACGCTGCTGCTCCAGG

ACGGCGTCTCCGGCCTGCAGGTGCAGCGCGGCGGCCGATGGGTGGCCGTG

AACCCCGTGCCCGACGCGCTGGTCATCAACATCGGAGACCAGATGCAGGC

ACTGAGCAACGACCGATACAAGAGCGTGCTCCACCGCGTGATCGTCAACA

GCGAGAGCGAGCGGATCTCGGTGCCGACGTTTTACTGCCCGTCGCCGGAC

GGGGTGATCGCGCCGGCCGACGCGCTGGTGGACGACGCCCACCCTCTGGC

CTACCGCCCCTTCACTTACCAGGAGTACTACGACGAGTTCTGGAACATGG

GCCTCCAGTCGGCAAGCTGCCTCGACCGGTTTAGGCCCGGAGGATCCATA
```
GAGTGA

Sorghum bicolor S3H homologous Protein sequence
(SEQ ID NO: 9):
MAPAISKPLLSDLVAQIGKVPSSHIRPVGDRPDLANVDNESGAGIPLIDL
KMLNGPERRKVVEAIGRACESDGFFMVTNHGIPAAVVEGMLRVAREFFHL
PESERLKCYSDDPKKAIRLSTSFNVRTEKVNNWRDFLRLHCYPLESFVDQ
WPSNPPSFRQVVGTYATEARALALRLLEAISESLGLERSHMVRAMGRHAQ
HMAVNYYPPCPQPELTYGLPGHKDPNAITLLLQDGVSGLQVQRGGRWVAV
NPVPDALVINIGDQMQALSNDRYKSVLHRVIVNSESERISVPTFYCPSPD
GVIAPADALVDDAHPLAYRPFTYQEYYDEFWNMGLQSASCLDRFRPGGSI

*Oryza sativa* (rice) S3H homologous Coding cDNA
sequence (SEQ ID NO: 10):
ATGGCTCCAGCCATTGCCAAGCCTCTCCTGAGCGATCTGGTGGCACAATC

CGGGCAAGTCCCCTCGAGCCACATTCGTCCGGTTGGCGACCGCCCGGACC

TCGACAACGTCGACCACGAGTCCGGCGCCGGCATTCCGGTCATCGACCTG

AAACAGCTCGACGGCCCGGATCGCCGCAAGGTTGTCGAGGCCATCGGTTC

GGCGTGCGAAACCGACGGTTTTTTCATGGTGAAGAATCACGGGATCCCGG

AGGAGGTGGTGGAAGGGATGCTGCGCGTGGCGAGGGAGTTCTTCCACATG

CCGGAGTCGGAGCGGCTCAAGTGCTATTCCGACGACCCCAAGAAGGCGAT

CCGGCTGTCGACGAGCTTCAACGTGCGCACCGAGAAGGTGAGCAACTGGC

GCGACTTCCTGCGCTTGCATTGCTACCCTCTCGAGAGCTTCATCGACCAG

TGGCCCTCCAACCCACCCTCCTTCAGGCAAGTGGTCGGCACCTACTCGAG

GGAGGCGAGGGCGCTGGCGCTGCGGTTGCTGGAGGCGATATCTGAGAGCC

TCGGGCTGGAGAGGGGCCACATGGTGTCGGCCATGGGGCGGCAGGCGCAG

CACATGGCGGTGAACTACTATCCGCCATGCCCACAGCCGGAGCTCACCTA

CGGCCTGCCGGGGCACAAGGACCCCAATGCCATCACGCTGCTGCTCCAGG

ACGGCGTCTCCGGCCTGCAGGTCCAGCGCAACGGCCGCTGGGTGGCCGTC

AACCCCGTGCCCGACGCCCTGGTCATCAACATCGGAGATCAAATCCAGGC

GCTGAGCAACGACCGGTATAAGAGCGTGCTCCACCGGGTGATCGTGAACA

GCGAGAGCGAGAGGATCTCCGTGCCGACGTTCTACTGCCCGTCCCCGGAC

GCGGTGATCGCGCCGGCCGGCGCGCTGGTGGACGGCGCCCTGCACCCGCT

GGCGTACCGGCCCTTCAAGTACCAGGCCTACTACGACGAATTCTGGAACA

TGGGCCTCCAGTCCGCCAGCTGCTTAGACCGGTTCCGGCCTAACGATCAG

GCCGTCTGA

*Oryza sativa* (Rice) S3H homologous protein
sequence (SEQ ID NO: 11):
MAPAIAKPLLSDLVAQSGQVPSSHIRPVGDRPDLDNVDHESGAGIPVIDL

KQLDGPDRRKVVEAIGSACETDGFFMVKNHGIPEEVVEGMLRVAREFFHM

PESERLKCYSDDPKKAIRLSTSFNVRTEKVSNWRDFLRLHCYPLESFIDQ

WPSNPPSFRQVVGTYSREARALALRLLEAISESLGLERGHMVSAMGRQAQ

HMAVNYYPPCPQPELTYGLPGHKDPNAITLLLQDGVSGLQVQRNGRWVAV

NPVPDALVINIGDQIQALSNDRYKSVLHRVIVNSESERISVPTFYCPSPD

AVIAPAGALVDGALHPLAYRPFKYQAYYDEFWNMGLQSASCLDRFRPNDQ

AV

*Hordeum vulgare* (common barley) S3H homologous
coding cDNA sequence (SEQ ID NO: 12):
ATGGCTCCGGCGATCGCCGCCAAGCCTCTCCTCAGTGATCTGGTGGCACA

AACCCGGCGAGTTCCGTCGAGCCACATCAGAGCGGTCGGAGACCGTCCGG

ACCTCGCCAATGTCGACCACGAGTCCGGCGCGGGCATTCCGCTCATCGAC

CTGAAGCACCTCGACGGGCCAGGGCGTCGCAGGGTCGTCGAGGCCATCGG

CTCGGCGTGCGAGAACGACGGTTTTTTCATGGTGACGAACCACGGCATCC

CGGAGGCGGTCGTGGACGGGATGCTGCGCGTGGCGAGGGAGTTCTTCCAC

CTGCCGGAGTCTGAACGGCTCAAGTGCTACTCAGACGACCCCAAGAAGGC

GATCCGGCTGTCCACGAGCTTCAACGTGCGCACCGAGAAGGTGAGCAACT

GGCGCGATTTCCTCCGCCTGCATTGCTACCCTCTCGAGAGCTTCATCGAC

CAGTGGCCCTCAAACCCGCCGGCCTTCAGGGAAGCAGTCGGCACCTACTC

GACGGAGGCGAGAGCGCTGGCGCTCAGGCTGCTGGAGGCGATATCGGAGA

GCCTTGGGCTGGAGAGAGGCCACATGGTGAAGGCCATGGGGCGGCACGCG

CAGCACATGGCGGTGAACTACTACCCGCCGTGCCCGCAGCCGGAGCTGAC

GTACGGACTGCCGGGCCACAAGGACCCCAATGCCGTCACGCTGCTCCTCC

AGGACGGCGTGTCCGGGCTTCAGGTCCGGCGCGACGGCCGCTGGGTCGCC

GTCAACCCCGTGCCCGGCGCGTTGGTCATCAACATCGGCGATCAACTGCA

GGCTCTGAGCAACGACCGATACAAGAGCGTACTTCACCGGGTGATTGTGA

ACAGCGAGAGCGAGAGGATCTCGGTGCCGACGTTCTACTGCCCGTCCCCG

GACGCGGTGGTCGCGCCGGCGGAGGCGCTGGTGGACGGCGGCCACCGTCT

GGCCTATCGGCCCTTCACCTACCAGGAGTACTACGAGGAGTTCTGGAACA

TGGGCCTCGAGGCCGCCAGCTGCCTCGACCGCTTCCGACCGATCGCGTGA

*Hordeum vulgare* (common barley) S3H homologous
Protein sequence (SEQ ID NO: 13):
MAPAIAAKPLLSDLVAQTRRVPSSHIRAVGDRPDLANVDHESGAGIPLID

LKHLDGPGRRRVVEAIGSACENDGFFMVTNHGIPEAVVDGMLRVAREFFH

LPESERLKCYSDDPKKAIRLSTSFNVRTEKVSNWRDFLRLHCYPLESFID

QWPSNPPAFREAVGTYSTEARALALRLLEAISESLGLERGHMVKAMGRHA

QHMAVNYYPPCPQPELTYGLPGHKDPNAVTLLLQDGVSGLQVRRDGRWVA

VNPVPGALVINIGDQLQALSNDRYKSVLHRVIVNSESERISVPTFYCPSP

DAVVAPAEALVDGGHRLAYRPFTYQEYYEEFWNMGLEAASCLDRFRPIA

*Triticum aestivum* (wheat) S3H homologous Coding
cDNA sequence (SEQ ID NO: 14):
ATGGCGCCGGTGAGCAACGAGACGTTCCTCCCGACGGCGGCCTGGGGGGA

GGCGACGCTGCGCCCGTCCTTCGTGCGGGACGAGGACGAGCGGCCCAAGG

TGGCGCACGACCGCTTCAGCGATGCGGTGCCGGTGATCTCGCTCGATGGC

ATCGACGGCGCGCGCCGGGCCGAGATCCGGGACCGCGTGGCGGCGGCCTG

CGAGGGCTGGGGCATCTTCCAGGTGGTCGACCACGGCGTCGACGCCGACC

TCATCGCCGACATGACGCGCCTCTCTCGCGAGTTCTTCGCGCTGCCCGCC

GAGGACAAGCTCCGGTACGACATGTCCGGTGGCAAGAAGGGCGGCTTCAT

CGTCTCCAGCCACCTGCAGGGTGAGGCGGTGCAGGACTGGAGGGAGATTG

TGACCTACTTCTCGTACCCGGTGAAAGCACGGGACTACGGGCGGTGGCCG

GAGAAGCCGGCGGGGTGGCGCGCGGTAGTGGAGCGGTACAGCGAGCGGCT

GATGGAGCTGTCGTGCAAGCTGCTGGGCGTGCTCTCGGAGGCGATGGGCC

TGGAGACGGAGTCCCTGGCCAAGGCGTGCGTGGACATGGACCAGAAGGTG

GTGGTCAACTTCTACCCGGTGTCCCCAGCCCGAGCTCACCCTGGGCGT

CAAGCGCCACACCGACCCCGGCACCATCACCCTCCTCCTCCAGGACCTAG

TCGGCGGCCTGCAGGCCACCCGCGACGGCGGCAAGACCTGGATCACCGTC

CAGCCCATCTCCGGCGCCTTCGTCGTCAACCTCGGCGACCACGGCCACTT

CATGAGCAACGGCAGGTTCAAGAACGCGGACCACCAGGCGGTGGTGAACG

GGCAGAGCAGCCGGCTGTCGATCGCGACGTTCCAGAACCCGGCGCCGGAC

```
GCGAGGGTGTGGCCGCTGGCGGTGAGGGAGGGGGAGGAGCCCATACTGGA
GGAGCCCATCACCTTCTCCGAGATGTACCGCCGCAAGATGGAGCGCGACC
TCGACCTCGCCAAGCGCAAGAAGCAGGCCAAGGACCAGCTGATGCAGCAG
CAGCTCCAGCTCCAGCAGCAGCAGCAGGCGGTCGCCGCCGCGCCCATGCC
CACCGCCACCAAGTCTCTCAACGAAATTCTTGCCTAG
```

Triticum aestivum S3H homologous protein sequence (SEQ ID NO: 15):
MAPVSNETFLPTAAWGEATLRPSFVRDEDERPKVAHDRFSDAVPVISLDG
IDGARRAEIRDRVAAACEGWGIFQVVDHGVDADLIADMTRLSREFFALPA
EDKLRYDMSGGKKGGFIVSSHLQGEAVQDWREIVTYFSYPVKARDYGRWP
EKPAGWRAVVERYSERLMELSCKLLGVLSEAMGLETESLAKACVDMDQKV
VVNFYPRCPQPELTLGVKRHTDPGTITLLLQDLVGGLQATRDGGKTWITV
QPISGAFVVNLGDHGHFMSNGRFKNADHQAVVNGQSSRLSIATFQNPAPD
ARVWPLAVREGEEPILEEPITFSEMYRRKMERDLDLAKRKKQAKDQLMQQ
QLQLQQQQQAVAAAPMPTATKSLNEILA Nicotiana tabacum S3H homologous coding cDNA sequence (SEQ ID NO: 16):
ATGGCACCTTCGACATTGACAGCTCTAGCAGAGGAAAAGACACTTCAAAC
AAGTTTCATAAGGGATGAAGATGAGCGTCCAAAAGTGGCTTATAATCAAT
TCAGTGACGAGATTCCGATCATATCGTTGAAGGGTATTGATGATGAGAGT
GGAATTAATGGAAAAGAGGTGAAATATGTGAAAGATTGTTAAGGCATG
TGAAGATTGGGCATTTTCCAGGTAGTTGATCATGGTGTTGATGCCCAAC
TTATCTCACAAATGACAACCCTTGCTAAACAATTCTTCGCTTTGCCTCCT
GAGGAAAAACTACGCTTTGATATGTCTGGTGGCAAGAAAGGTGGCTTCAT
TGTCTCTAGCCATCTACAGGGTGAAGTGGTCCAAGATTGGCGTGAAATAG
TGACCTATTTCTCATATCCAATTCGGGCTAGAGACTACTCTAGATGGCCA
GACAAACCAGATGGATGGATAGGTGTGACTCAGAAGTACAGTGAAAAGTT
AATGGAGTTGGCTTGCAAATTATTGGAAGTACTATCAGAGGCAATGGGCT
TAGAGAAGGAGGCCTTAACCAAGGCATGTGTGGATATGGACCAAAAAGTG
GTTGTCAATTTTTACCCAAAGTGTCCACAGCCCGACCTTACCCTTGGACT
GAAACGACACACTGATCCAGGAACCATTACCCTCTTGTTACAAGACCAAG
TTGGTGGGCTTCAAGCCACTAAAGATAATGGCAAAACTTGGATTACTGTT
CAGCCCGTTGAAGGCGCTTTTGTTGTCAATCTTGGTGACCATGGTCACTT
TTTGAGCAATGGAAGGTTTAAGAATGCTGATCATCAAGCAGTGGTGAACT
CGAATAGTAGCAGATTATCGATAGCTACGTTTCAGAATCCAGCACCAGAA
GCTATAGTGTACCCATTGAAAATTAGGGAAGGAGAGAAGGCAGTAATGGA
CGAGCCCATAACATTTGCAGAGATGTACAGGAGGAAAATGAGCAAGGACC
TTGAGCTTGCTAGGCTCAAGAAACTGGCCAAGGAACACCAAATACAAGCT
GAAAAAGCTGCTGAGAAGGCCAAGTTGAAAACCAAGCCCATTGAAGAAAT
TCTTGCTTAA Nicotiana tabacum S3H homologous protein sequence (SEQ ID NO: 17):
MAPSTLTALAEEKTLQTSFIRDEDERPKVAYNQFSDEIPIISLKGIDDES
GINGKRGEICEKIVKACEDWGIFQVVDHGVDAQLISQMTTLAKQFFALPP
EEKLRFDMSGGKKGGFIVSSHLQGEVVQDWREIVTYFSYPIRARDYSRWP
DKPDGWIGVTQKYSEKLMELACKLLEVLSEAMGLEKEALTKACVDMDQKV
VVNFYPKCPQPDLTLGLKRHTDPGTITLLLQDQVGGLQATKDNGKTWITV
QPVEGAFVVNLGDHGHFLSNGRFKNADHQAVVNSNSSRLSIATFQNPAPE
AIVYPLKIREGEKAVMDEPITFAEMYRRKMSKDLELARLKKLAKEHQIQA
EKAAEKAKLKTKPIEEILA Petunia S3H homologous coding cDNA sequence (SEQ ID NO: 18):
ATGAAAACAGCTCAAGGTGTCAGTGCAACCCTAACAATGGAAGTGGCAAG
AGTACAAGCAATAGCATCGTTAAGCAAGTGCATGGACACAATTCCATCAG
AGTACATTAGGTCCGAGAATGAGCAACCAGCAGCCACAACCCTGCATGGG
GTAGTTCTTCAAGTGCCAGTGATTGACCTACGTGACCCTGATGAGAACAA
GATGGTGAAGCTCATAGCTGATGCTAGCAAAGAGTGGGGGATATTCCAAC
TGATCAACCATGGCATTCCTGATGAGGCTATCGCGGATTTACAGAAAGTA
GGGAAAGAGTTCTTTGAACATGTTCCACAGGAGGAGAAAGAGCTGATTGC
CAAGACTCCAGGATCAAACGACATTGAAGGCTATGGAACTTCTCTGCAGA
AGGAAGTGGAAGGCAAGAAAGGTTGGGTGGATCATTTGTTCCATAAGATT
TGGCCTCCTTCTGCCGTCAACTATCGTTATTGGCCTAAAAACCCTCCTTC
ATACAGGGAAGCAAACGAAGAATATGGAAAGAGGATGCGAGAAGTTGTAG
ACAGAATTTTTAAGAGCTTGTCTCTTGGGCTTGGGCTTGAAGGCCATGAA
ATGATAGAGGCAGCTGGTGGTGATGAGATAGTTTACTTGTTGAAGATCAA
CTATTACCCACCATGCCCAAGGCCCGATTTGGCTCTTGGTGTTGTGGCCC
ATACGGACATGTCATATATCACCATTCTTGTCCCAAATGAAGTCCAAGGC
CTCCAAGTGTTCAAGGATGGCCATTGGTATGATGTCAAGTACATACCAAA
TGCCTTAATTGTCCATATTGGTGACCAAGTTGAGATTCTTAGCAATGGCA
AATACAAGAGTGTATACCATAGGACAACGGTGAACAAGGACAAGACAAGA
ATGTCATGGCCGGTTTTCTTGGAGCCCCCGTCAGAGCATGAAGTTGGGCC
AATTCCTAAGCTGCTTAGTGAGGCCAACCCACCCAAATTCAAGACCAAGA
AGTACAAGGATTACGTCTATTGTAAGCTTAACAAGCTTCCTCAGTGA Petunia S3H homologous protein sequence (SEQ ID NO: 19):
MKTAQGVSATLTMEVARVQAIASLSKCMDTIPSEYIRSENEQPAATTLHG
VVLQVPVIDLRDPDENKMVKLIADASKEWGIFQLINHGIPDEAIADLQKV
GKEFFEHVPQEEKELIAKTPGSNDIEGYGTSLQKEVEGKKGWVDHLFHKI
WPPSAVNYRYWPKNPPSYREANEEYGKRMREVVDRIFKSLSLGLGLEGHE
MIEAAGGDEIVYLLKINYYPPCPRPDLALGVVAHTDMSYITILVPNEVQG
LQVFKDGHWYDVKYIPNALIVHIGDQVEILSNGKYKSVYHRTTVNKDKTR
MSWPVFLEPPSEHEVGPIPKLLSEANPPKFKTKKYKDYVYCKLNKLPQ.

Glycine max (Soybean) S3H homologous coding cDNA sequence (SEQ ID NO: 20)
ATGGCCACCACAAAGCCATTGTTAACCGACTTAGCCTCCACCGTTGATCG
TGTTCCCTCTAACTTCATCAGGCCCATTGGTGACCGTCCAAACCTTCAGC
AACTTCACTCCTCCATTGCTTCTATTCCCATCATCGACCTTCAAGGCCTT

```
GGTGGCTCCAATCATTCCCAAATCATCCAAAACATTGCACATGCTTGCCA
AAATTATGGCTTCTTTCAAATTGTGAACCATGGGATTCCGGAGGAGGTGG
TGAGCAAGATGGTGAATGTGTCAAAAGAGTTCTTTGGTTTGCCGGAGAGT
GAGAGGCTGAAGAATTACTCTGATGACCCAACCAAGACCACAAGACTCTC
CACCAGTTTCAATGTCAAGACTGAGAAAGTTTCCAACTGGAGAGACTTCT
TGAGACTTCACTGCCACCCCTTGAGGATTACATTCAAGAATGGCCTGGC
AACCCTCCATCTTTCAGGGAAGATGTGGCGGAGTATAGTAGAAAGATGAG
GGGTTTATCACTGAAGTTGCTTGAGGCAATCTCAGAGAGTTTGGGGTTGG
AAAAGGATTATATAGACAAAGCATTGGGGAAACATGGGCAGCACATGGCC
ATAAACTACTACCCTCCATGTCCTGAGCCAGAGTTAACATATGGTTTGCC
AGCTCATGCTGACCCAAATGCAATTACTATTCTGCTCCAAAATCAAGTCC
CTGGCTTGCAAGTCCTCCATGATGGCAAGTGGCTAACCGTCAATCCTGTT
CCTAACACCTTCATTGTCAATATTGCTGACCAAATTCAGGTGATAAGCAA
CGATAGGTACAAGAGTGTGCTGCATCGAGCATTGGTGAATTGTGAGAAGG
AGAGAATGTCCATTCCAACATTCTATTGCCCTTCACCTGATGCATTGATA
AAACCAGCACCACAACTCGTAGACAAGGAACATCCTGCGCAGTACACAAA
CTTCACATACAGAGAATACTACGACAAGTTCTGGATCAGAGGACTTTCAA
AAGAAACATGCGTGGACATGTTCAAGGCTCAAGATTAA

Glycine max (Soybean) S3H homologous protein
sequence (SEQ ID NO: 21):
MATTKPLLTDLASTVDRVPSNFIRPIGDRPNLQQLHSSIASIPIIDLQGL
GGSNHSQIIQNIAHACQNYGFFQIVNHGIPEEVVSKMVNVSKEFFGLPES
ERLKNYSDDPTKTTRLSTSFNVKTEKVSNWRDFLRLHCHPLEDYIQEWPG
NPPSFREDVAEYSRKMRGLSLKLLEAISESLGLEKDYIDKALGKHGQHMA
INYYPPCPEPELTYGLPAHADPNAITILLQNQVPGLQVLHDGKWLTVNPV
PNTFIVNIADQIQVISNDRYKSVLHRALVNCEKERMSIPTFYCPSPDALI
KPAPQLVDKEHPAQYTNFTYREYYDKFWIRGLSKETCVDMFKAQD Cotton S3H coding cDNA homologous sequence
(SEQ ID NO: 22):
ATGGCTCCTCAACTCTGACGGCTCTTGCGGAAGAGAAAACCTTGCAGGC
AAGCTTCGTTCGTGATGAAGATGAGCGTCCTAAGGTTGCTTACAACCAAT
TCAGTAATGATATCCCTGTCATCTCTCTTGCTGGTATCGATGATGTTGAT
GGCAAGAGGGGTGAGATATGCAAGAAGATTGTTGAGGCTTGTGAGGATTG
GGGTGTCTTCCAGGTTGTGGATCATGGTGTTGATACTAAACTCGTGTCCG
AAATGACCCGTTTTGCCAGAGAGTTTTTTGCTTTGCCTGCTGAAGAGAAG
CTTCGGTTCGATATGTCTGGTGGCAAGAAAGGTGGTTTCATCGTCTCCAG
CCACCTTCAGGGAGAAGCAGTGCAAGATTGGCGGAGATTGTGACATACT
TTTCATACCCATTGAAGAGCAGGGACTATTCAAGGTGGCCTGATAAGCCA
GAGGGTTGGATTGAAGTTACAAAGGAGTACAGCGAGAAGTTGATGGGCCT
AGCTTGCAAGCTTCTTGAGGTGTTGTCAGAGGCCATGGGGTTAGAGAAGG
AGGCTTTGACTAAGGCATGTGTGGACATGGATCAGAAAGTGGTGGTTAAC
TTCTATCCTAAATGCCCTCAACCTGACCTCACTTTAGGACTCAAGCGCCA
CACTGACCCAGGCACCATCACACTCTTGCTTCAAGACCAAGTTGGTGGGC
```

```
TTCAGGCCACCCGGGACAATGGCAAGACGTGGATCACTGTCCAACCTGTG
GAAGGAGCCTTTGTGGTCAACCTTGGAGACCATGGCCATTATCTGAGCAA
TGGGAGGTTCAAGAATGCTGATCACCAAGCAGTGGTGAACTCAAACTGCA
GCAGATTGTCAATAGCCACATTCCAAAATCCAGCACCCGATGCCACAGTG
TATCCCTTGAAGATCAGAGAGGGAGAGAAACCAATCCTTGAGGAGCCCAT
CACATTTGCTGAGATGTATAGGAGGAAGATGAGCAAGGATCTTGAGCTTG
CCAGGCTGAAGAAGCTGGCCAAAGAGCAGCAACAGTTGAAGGAGAAAGAG
GCTGAGAATGAGAAGCCCAAGCTTGAAGCCAAGCCATTGGAGGAAATCCT
TGCCTAA

Cotton S3H protein homologous sequence
(SEQ ID NO: 23):
MAPSTLTALAEEKTLQASFVRDEDERPKVAYNQFSNDIPVISLAGIDDVD
GKRGEICKKIVEACEDWGVFQVVDHGVDTKLVSEMTRFAREFFALPAEEK
LRFDMSGGKKGGFIVSSHLQGEAVQDWREIVTYFSYPLKSRDYSRWPDKP
EGWIEVTKEYSEKLMGLACKLLEVLSEAMGLEKEALTKACVDMDQKVVVN
FYPKCPQPDLTLGLKRHTDPGTITLLLQDQVGGLQATRDNGKTWITVQPV
EGAFVVNLGDHGHYLSNGRFKNADHQAVVNSNCSRLSIATFQNPAPDATV
YPLKIREGEKPILEEPITFAEMYRRKMSKDLELARLKKLAKEQQQLKEKE
AENEKPKLEAKPLEEILA Malus domestica (Apple) S3H homologous coding cDNA
sequence (SEQ ID NO: 24):
ATGGCTCCTCCTGCTACTACGCTGACATCCATTGCGCATGAGAAAACCCT
ACAACAAAAATTCGTCCGAGACGAAGACGAGCGTCCAAAGGTTGCCTACA
ACGAATTCAGCAACGAAATTCCGATCATCTCGCTTGCCGGGATCGATGAG
GTTGAAGGCCGCCGGGCCGAGATTTGCAAGAAGATTGTGGAAGCTTGTGA
GGACTGGGGTATTTTCCAGATTGTTGATCATGGAGTTGATGCCGAGCTCA
TATCGGAAATGACCGGTCTCGCCAAAGAGTTCTTTGATTTGCCATCGGAG
GAGAAGCTCCGCTTCGACATGTCCGGTGGCAAAAAGGGTGGATTCATCGT
GTCCAGTCATTTACAGGGAGAAGCTGTGCAAGATTGGCGTGAAATTGTGA
CCTACTTTTTATACCCGATTCGCCACCGGGACTACTCGAGGTGGCCGGAC
AAGCCAGAGGCATGGAGGGAGGTGACGAAGAAGTACAGCGACGAGCTGAT
GGGGCTGGCATGCAAGCTCTTGGGGGTTTTATCAGAAGCCATGGGGTTGG
ATACAGAGGCATTGACAAAGGCATGTGTGGACATGGACCAAAAAGTGGTG
GTGAATTTCTATCCGAAGTGCCCTCAGCCCGACCTAACTCTTGGCCTCAA
GCGCCACACGACCCGGGCACAATTACCCTTTTGCTTCAGGACCAAGTTG
GTGGCCTTCAGGCTACTAGGGATGATGGGAAGACATGGATCACCGTTCAA
CCAGTGGAAGGAGCTTTTGTGGTCAATCTCGGAGATCATGGTCATTTTCT
GAGCAATGGGAGGTTCAAGAATGCTGATCACCAAGCAGTGGTGAACTCAA
ACAGCAGCAGGCTGTCCATAGCCACATTCCAGAACCCAGCTCAAGATGCA
ATAGTGTATCCACTCAGTGTGAGGGAGGGAGAGAAGCCGATTCTCGAGGC
GCCGATCACCTACACCGAGATGTACAAGAAGAAGATGAGCAAAGATCTTG
AGCTTGCCAGGCTGAAAAAGCTGGCCAAGGAACAGCAACTGCAGGACTTG
GAGAAAGCCAAAGTGGAGACAAAGCCAGCGGACGACATATTTGCTTAG
```

*Malus domestica* (Apple) S3H homologous protein sequence (SEQ ID NO: 25):
MAPPATTLTSIAHEKTLQQKFVRDEDERPKVAYNEFSNEIPIISLAGIDE
VEGRRAEICKKIVEACEDWGIFQIVDHGVDAELISEMTGLAKEFFDLPSE
EKLRFDMSGGKKGGFIVSSHLQGEAVQDWREIVTYFLYPIRHRDYSRWPD
KPEAWREVTKKYSDELMGLACKLLGVLSEAMGLDTEALTKACVDMDQKVV
VNFYPKCPQPDLTLGLKRHTDPGTITLLLQDQVGGLQATRDDGKTWITVQ
PVEGAFVVNLGDHGHFLSNGRFKNADHQAVVNSNSSRLSIATFQNPAQDA
IVYPLSVREGEKPILEAPITYTEMYKKKMSKDLELARLKKLAKEQQLQDL
EKAKVETKPADDIFA

*Brassica napus* S3H Coding cDNA homologous sequence (SEQ ID NO: 26):
ATGGCTCCAGGAACTCTAAATGAGCTTGCCGGAGAGACTAAGCTCAACTC
CAAGTTTGTCCGGGACGAGGACGAACGTCCCAAGGTTGCCTACAATGAGT
TTAGCACGGAGATCCCCGTGATCTCTCTCGCCGGAATCGACGATGTTGGT
GAGAAAAGAGGAGAGATCTGTCGACAGATCGTTGAGGCTTGTGAGAACTG
GGGTGTTTTTCAGGTGGTCGATCATGGAGTGGATACTAGTTTGGTGGCCG
ATATGACTCGTCTCGCTCGAGACTTCTTCGCGTTACCTCCTGAGGAGAAA
CTCAAGTTCGACATGTCTGGTGGTAAAAAGGGAGGATTCATTGTCTCTAG
TCATCTTCAGGGAGAGTCTGTTCAAGATTGGAGAGAGATCGTGACGTATT
TCTCGTACCCGGTGAGAAACAGAGACTACTCACGGTGGCCGACTAAGCCG
GAAGGATGGGTGAAAGTGACGGAGGAGTACAGCGAGAGGCTGATGGGTTT
GGCTTGTAAACTTCTTGAGGTTTTGTCTGAAGCTATGGGGCTCGAGAAAG
AGGCACTCACCAATGCATGCGTCGATATGGACCAGAAAATAGTTGTTAAC
TATTACCCAAAATGCCCTCAGCCTGATCTAACCCTCGGGCTCAAGCGTCA
CACTGACCCTGGAACCATCACTTTGCTGCTCCAAGACCAAGTTGGTGGTT
TACAAGCCACACGAGACGATGGGAAGACATGGATTACAGTTCAGCCTGTT
GAAGGAGCTTTTGTTGTTAATCTTGGCGACCATGGTCACTATCTGAGCAA
CGGGAGGTTCAAGAACGCTGACCACCAGGCGGTGGTGAACTCCAACTCGA
GCAGACTATCAATAGCCACGTTCCAGAATCCGGCGCCGGAAGCAACCGTG
TATCCGCTTAAAGTGAGAGAAGGAGAGAAGCCGATCTTGGAGGAGCCAAT
TACGTTTGCGGAGATGTATAAGAGAAAGATGAGTAGAGATCTCGAGCTGG
CTCGCCTCAAGAAGCTGGCGAAAGAAGAGCATGACCACAAGGAAGCTGCC
AAGCCTCTAGACCAAATCATCGCTTAG

*Brassica napus* S3H homologous protein sequence (SEQ ID NO: 27):
MAPGTLNELAGETKLNSKFVRDEDERPKVAYNEFSTEIPVISLAGIDDVG
EKRGEICRQIVEACENWGVFQVVDHGVDTSLVADMTRLARDFFALPPEEK
LKFDMSGGKKGGFIVSSHLQGESVQDWREIVTYFSYPVRNRDYSRWPTKP
EGWVKVTEEYSERLMGLACKLLEVLSEAMGLEKEALTNACVDMDQKIVVN
YYPKCPQPDLTLGLKRHTDPGTITLLLQDQVGGLQATRDDGKTWITVQPV
EGAFVVNLGDHGHYLSNGRFKNADHQAVVNSNSSRLSIATFQNPAPEATV
YPLKVREGEKPILEEPITFAEMYKRKMSRDLELARLKKLAKEEHDHKEAA
KPLDQIIA

*Solanum tuberosum* (Potato) S3H homologous coding cDNA sequence (SEQ ID NO: 28):
ATGGCTTCAACACTAACAGCTCTAGCTAATGAAAAGACCCTTCAACAAG
TTTTATTAGGGATGAAGAAGAACGTCCAAAAGTGGCTTACAATAAATTTA
GTGACGAAATTCCAGTAATATCGTTGCAAGGTATTGATGATATTAATGGA
AGAAGAAGTGAAATATGTGAGAAAATTGTAAATGCTTGTGAAGATTGGGG
AGTTTTTCAGGTAATTGATCATGGGGCCGATGCTCAATTAATATCAGAAA
TGACAAAATTGGCTAAGGAATTTTTCGAATTGCCTCCTGACGAAAAGCTT
CGGTTTGACATGTCTGGTGGCAAGAAAGGCGGCTTTATTGTCTCAAGCCA
TTTACAGGGTGAAGTGGTTCAAGACTGGCGTGAAATAGTGACCTACTTTT
CTTACCCAATTCGAGCTAGAGACTACTCCAGATGGCCAGACAAACCACAA
GGCTGGATAGCTGTAACTGAGAAATACAGTGAAAAATTAATGGACTTGGC
TTGCAAATTATTAGAAGTATTATCAGAGGCAATGGGCTTAGAGAAAGAGG
CTTTAACCAAGGCATGTGTGGATATGGACCAAAAAGTAGTTGTCAATTTT
TACCCAAAGTGTCCAGAGCCTGACCTTACCCTTGGGCTGAAACGACATAC
TGATCCAGGAACCATCACCCTCTTGTTACAAGACCAAGTTGGTGGGCTTC
AAGCCACTAAAGATAATGGCAAAACTTGGATCACTGTTCAGCCCGTTGAA
GGCGCTTTTGTTGTTAATCTTGGTGATCATGGTCATTATTTGAGCAATGG
GAGGTTCAAGAATGCTGATCATCAAGCAGTTGTGAATTCGAATAGCAGCA
GATTATCGATAGCCACTTTTCAGAATCCAGCACCGGATGCAAAAGTGTAT
CCGTTAAAAATTAGGGAAGGAGAAAGGCAATAATGGATGAGCCGATTAC
ATTTGCAGAAATGTACAGGAGGAAAATGAGTAAGGATCTTGAGCTTGCTA
GGCTCAAGAAACTGGCCAAGGAACAGACTGAAGAGGCCAAGTTGGAGTCC
AAGCCCATTGAGGAAATTCTTGCTTAA

*Solanum tuberosum* (Potato) S3H homologous protein sequence (SEQ ID NO: 29):
MASTLTALANEKTLQTSFIRDEEERPKVAYNKFSDEIPVISLQGIDDING
RRSEICEKIVNACEDWGVFQVIDHGADAQLISEMTKLAKEFFELPPDEKL
RFDMSGGKKGGFIVSSHLQGEVVQDWREIVTYFSYPIRARDYSRWPDKPQ
GWIAVTEKYSEKLMDLACKLLEVLSEAMGLEKEALTKACVDMDQKVVVNF
YPKCPEPDLTLGLKRHTDPGTITLLLQDQVGGLQATKDNGKTWITVQPVE
GAFVVNLGDHGHYLSNGRFKNADHQAVVNSNSSRLSIATFQNPAPDAKVY
PLKIREGEKAIMDEPITFAEMYRRKMSKDLELARLKKLAKEQTEEAKLES
KPIEEILA

*Solanum lycopersicum* (Tomato) S3H homologous coding cDNA sequence (SEQ ID NO: 30):
ATGACAACAACAAGTGTTCTTTCTAGTGGATTCAACCACTCAACCCTCCC
TCAGTCTTACGTTCGACCTGAATCTCAAAGACCTTGCATGTCTGAAGTTG
TTGATAGCGACGATCTTGTCCCAGTCATTGATATGTCTTGTACTAATAGG
AACGTTATCGTTCATCAAATCGGTGAAGCTTGTCGTCTTTATGGGTTTTT
CCAGGTGATAAATCACGGTGTGTCGAAGAAGGTGATAGATGAAATGTTAG -continued
GGGTAAGTCATGAATTTTTTAAGCTACCAGTTGAAGAAAAGATGAAATTG

TATTCTGATGATCCATCAAAAACTATGAGATTATCAACTAGTTTTAATGT

TAAGAAGGAAGCTGTTCATAATTGGAGAGATTATCTTAGGCTACATTGTT

ATCCTTTGGACAAATATGCCCCTGAATGGCCTTCTAATCCTCCTTCTTTC

AGGGAAATAGTAAGCAAATATTGCATGGAAGTTAGAGAGCTTGGATATAG

ATTGGAAGAAGCAATATCAGAGAGCTTAGGGCTTGAGAAGGATTGTATAA

AAAATGTGTTAGGTGAACAAGGACAACATATGGCTATCAATTTTTATCCT

CAGTGTCCACAACCTGAATTAACTTATGGGTTACCAGCCCATACAGATCC

AAATGCAATTACAATTCTTCTTCAAGATTTGCAAGTGGCTGGCCTTCAAG

TTCTTAAGGATGGAAAATGGCTATCTATTAAACCTCAGCCTAATGCCTTT

GTCATCAATCTTGGTGATCAATTGGAGGCGTTGAGTAATGGGAAGTATAA

AAGTATATGGCATAGAGCTATAGTGAATTCAGACAAAGCAAGGATGTCTG

TGGCTTCTTTCCTCTGTCCCAATGATTGTTCCATTATCAGTGCTCCAAAA

ACCTTAACTGAAGATGGATCTTCTGCAATTTATCGACATTTCACTTATGC

TGAATATTATGAAAAATTCTGGAGCAGGAATTTAGATCAGGAATATTGTT

TAGAACTTTTCAAGAACGATGGAACCTAG

*Solanum lycopersicum* (Tomato) S3H homologous
protein sequence (SEQ ID NO: 31):
MTTTSVLSSGFNHSTLPQSYVRPESQRPCMSEVVDSDDLVPVIDMSCTNR

NVIVHQIGEACRLYGFFQVINHGVSKKVIDEMLGVSHEFFKLPVEEKMKL

YSDDPSKTMRLSTSFNVKKEAVHNWRDYLRLHCYPLDKYAPEWPSNPPSF

REIVSKYCMEVRELGYRLEEAISESLGLEKDCIKNVLGEQGQHMAINFYP

QCPQPELTYGLPAHTDPNAITILLQDLQVAGLQVLKDGKWLSIKPQPNAF

VINLGDQLEALSNGKYKSIWHRAIVNSDKARMSVASFLCPNDCSIISAPK

TLTEDGSSAIYRHFTYAEYYEKFWSRNLDQEYCLELFKNDGT

In one embodiment, the transgenic plant has a reduced level of S3H and displays a precocious or premature leaf senescence phenotype.

In one embodiment, the plant is transformed with a nucleic acid construct comprising a nucleic acid molecule configured to silence S3H protein expression.

In one embodiment, the nucleic acid molecule is configured to silence a protein having the amino acid sequence of NxYPxCPxPxLxxGxxxHxDxxxxTxLLQD (SEQ ID NO: 1), where x can be any amino acid residue. In another embodiment, the nucleic acid construct is configured to silence a protein having the amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31.

In one embodiment, the transgenic plant has an increased level of S3H protein and displays a delayed leaf senescence phenotype. In this embodiment, the plant may be transformed with a nucleic acid construct configured to overexpress S3H protein.

Figure 14:
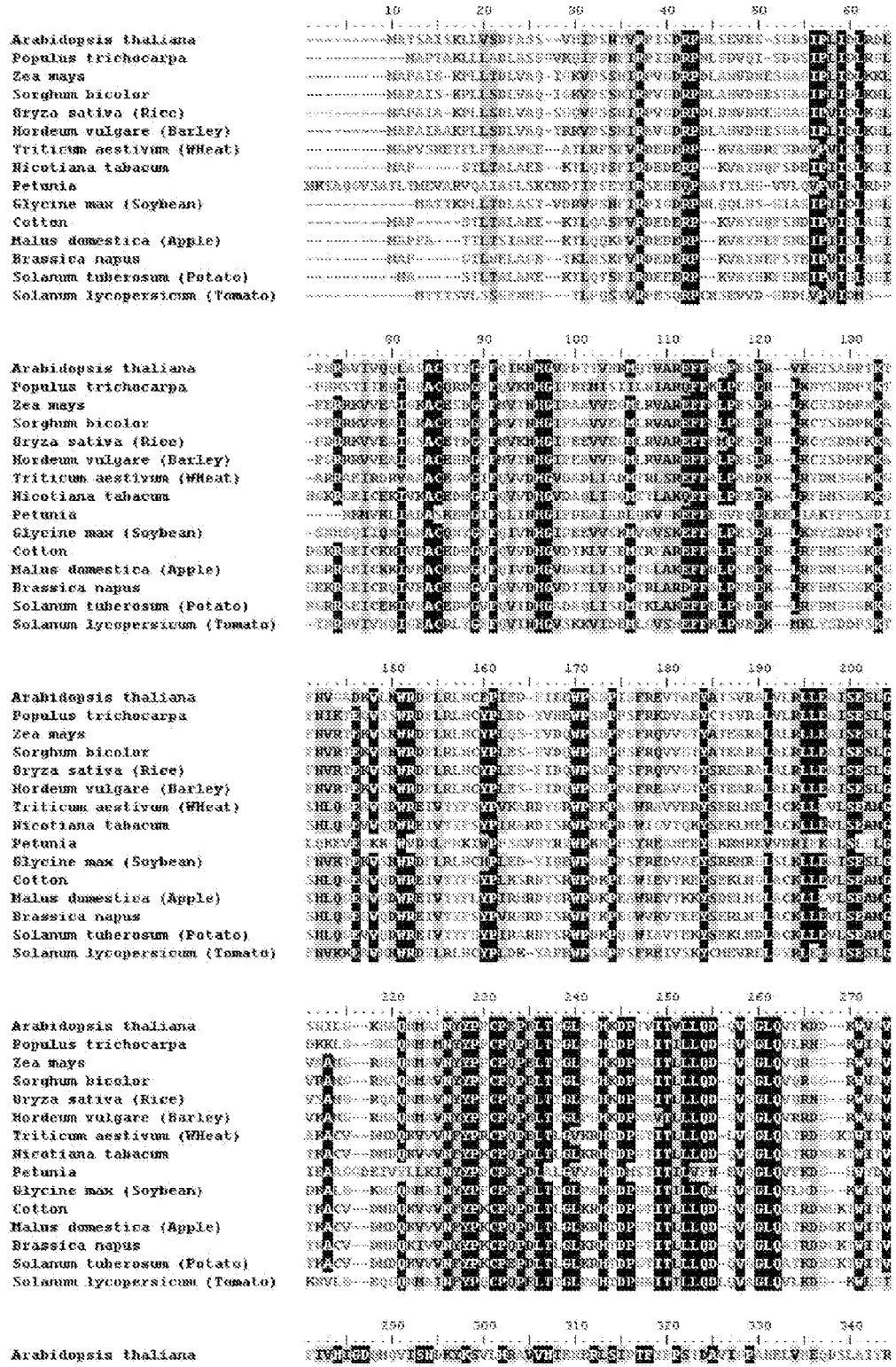
FIG. 14 shows an amino acid sequence alignment of S3H protein, as well as an alignment of nucleotide sequences encoding S3H protein, from *Arabidopsis thaliana, Populus trichocarpa, Zea mays, Sorghum bicolor, Oryza sativa* (rice), *Hordeum vulgare* (common barley), *Triticum aestivum* (wheat), *Nicotiana tabacum, petunia, Glycine max* (Soybean), cotton, *Malus domestica* (Apple), *Brassica napus, Solanum tuberosum* (Potato), and *Solanum lycopersicum* (Tomato) (amino acid sequences of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31, respectively; nucleotide sequences of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30, respectively).
Figure 14:
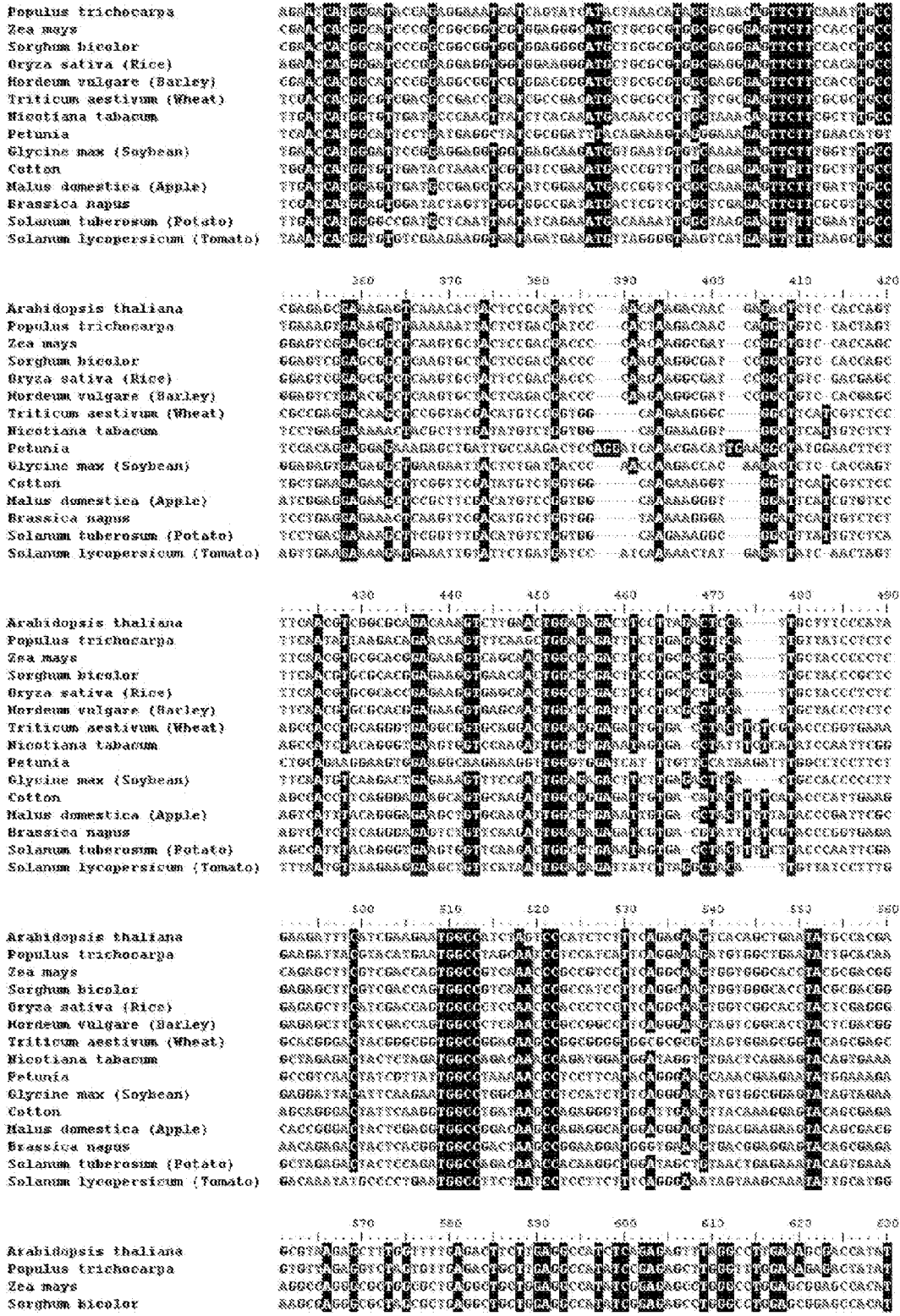
Figure 14:
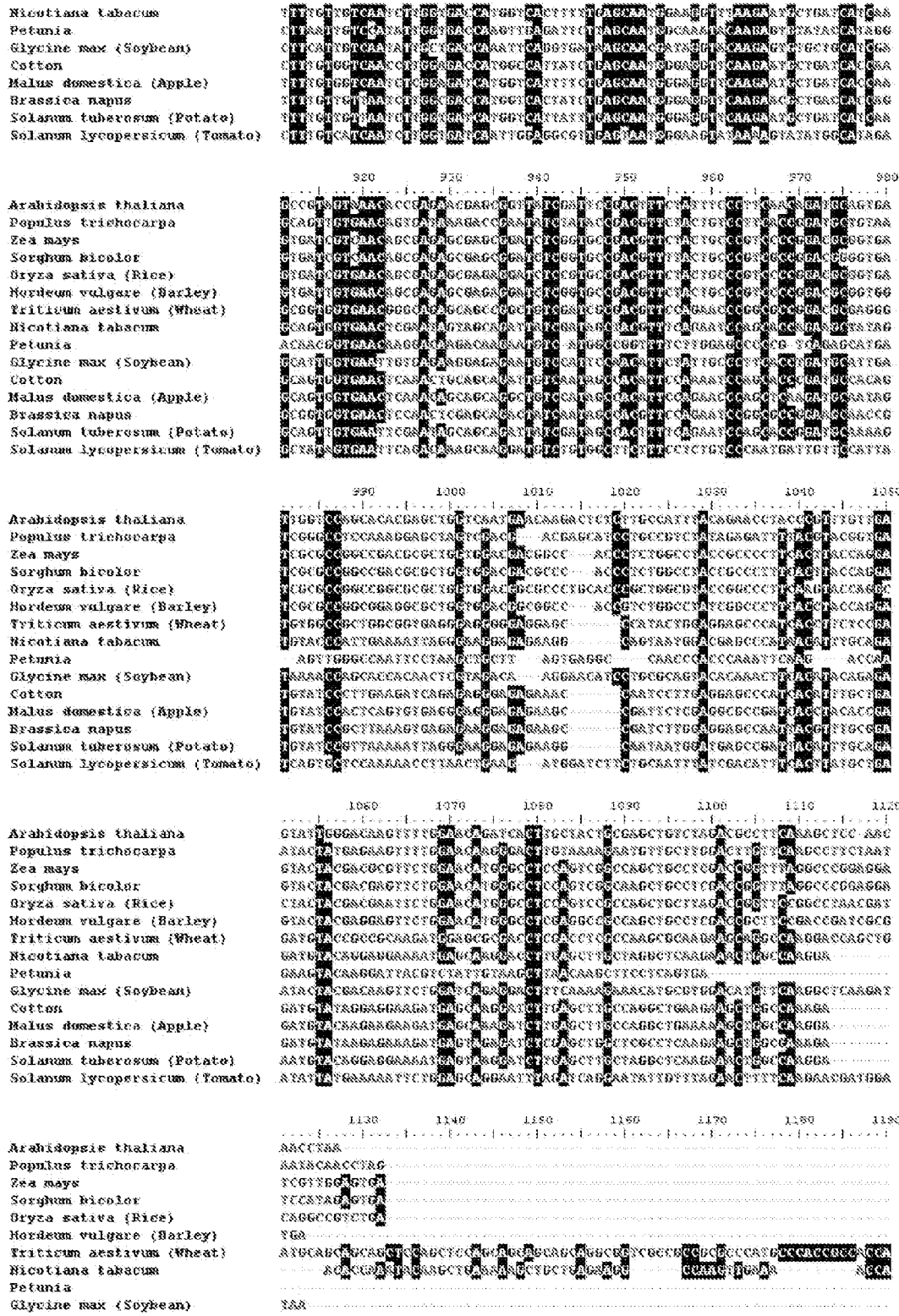

Accordingly, the nucleic acid construct may encode a protein having the amino acid sequence of NxYPxCPxPx-LxxGxxxHxDxxxxTxLLQD (SEQ ID NO: 1), wherein x can be any amino acid residue. The nucleic acid construct may also encode a protein having the amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and SEQ ID NO: 31. An alignment of these sequences is shown in FIG. 14.

The nucleic acid molecule may include the nucleotide sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30.

While activity in particular polypeptide or protein sequences has been identified, variants of those polypeptides are also contemplated and may also be used as described herein (e.g., to alter senescence and/or impart or enhance disease resistance). In some embodiments, the polypeptides of the invention comprise one or more (e.g., 1, 2, 3, 4, 5 or more) amino acid insertions, deletions, or modifications (e.g., substitution of one amino acid for another) compared to SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and/or SEQ ID NO: 31 or are otherwise substantially identical (e.g., having a sequence at least 80%, 85%, 90%, 95%, 96%, 97%, 98%, 99% or more identical) with the entire sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, and/or SEQ ID NO: 31. For example, polypeptides comprising or consisting of an amino acid sequence having one or more (e.g., 1, 2, 3, 4, 5, or more) conservative amino acid substitutions relative to such sequences, but retaining the function of such sequences (e.g., in altering leaf senescence and/or imparting or enhancing disease resistance) are encompassed. Further, nucleic acid molecules encoding such variants of the peptides of the present invention are also contemplated. Such nucleic acid molecules may have, for example, a nucleotide sequence at least 80%, 85%, 90%, 95%, 96%, 97%, 98%, 99% or more identical) with the entire sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and/or SEQ ID NO: 30.

Components of nucleic acid constructs according to the present invention may be heterologous or exogenous. A polynucleotide sequence is "heterologous to" or "exogenous to" an organism or a second polynucleotide sequence if it is synthetic or originates from a foreign species, or, if from the same species, is modified from its original form. For example, a promoter operably linked to a heterologous coding sequence (or vice versa) refers to a coding sequence from a species different from that from which the promoter was derived, or, if from the same species, a coding sequence which is not naturally associated with the promoter (e.g. a genetically engineered coding sequence or an allele from a different ecotype or variety).

Methods of producing recombinant nucleic acids for purposes of, e.g., making transgenic plants are well-known. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning:*

*A Laboratory Manual*, Second Edition, Cold Spring Harbor, N.Y., Cold Spring Harbor Press (1989), and Ausubel et al., *Current Protocols in Molecular Biology*, New York, N.Y., John Wiley & Sons (1989), which are hereby incorporated by reference in their entirety.

In preparing a nucleic acid vector for expression, the various nucleic acid sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly-used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. Tissue-specific and organ-specific promoters can also be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens* (U.S. Pat. No. 5,034,322 to Rogers et al., which is hereby incorporated by reference in its entirety), the cauliflower mosaic virus (CaMV) 35S and 19S promoters (U.S. Pat. No. 5,352,605 to Fraley et al., which is hereby incorporated by reference in its entirety), those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11:605-612 (1997); and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known by those of ordinary skill in the art (U.S. Pat. No. 5,750,385 to Shewmaker et al., which is hereby incorporated by reference in its entirety).

A number of tissue- and organ-specific promoters have been developed for use in genetic engineering of plants (Potenza et al., "Targeting Transgene Expression in Research, Agricultural, and Environmental Applications: Promoters Used in Plant Transformation," *In Vitro Cell. Dev. Biol. Plant* 40:1-22 (2004), which is hereby incorporated by reference in its entirety). Examples of such promoters include those that are floral-specific (Annadana et al., "Cloning of the *Chrysanthemum* UEP1 Promoter and Comparative Expression in Florets and Leaves of *Dendranthema gran-* diflora," *Transgenic Res.* 11:437-445 (2002), which is hereby incorporated by reference in its entirety), seed-specific (Kluth et al., "5' Deletion of a gbss1 Promoter Region Leads to Changes in Tissue and Developmental Specificities," *Plant Mol. Biol.* 49:669-682 (2002), which is hereby incorporated by reference in its entirety), root-specific (Yamamoto et al., "Characterization of cis-acting Sequences Regulating Root-Specific Gene Expression in Tobacco," *Plant Cell* 3:371-382 (1991), which is hereby incorporated by reference in its entirety), fruit-specific (Fraser et al., "Evaluation of Transgenic Tomato Plants Expressing an Additional Phytoene Synthase in a Fruit-Specific Manner," *Proc. Natl. Acad. Sci. USA* 99:1092-1097 (2002), which is hereby incorporated by reference in its entirety), and tuber/storage organ-specific (Visser et al., "Expression of a Chimaeric Granule-Bound Starch Synthase-GUS Gene in Transgenic Potato Plants," *Plant Mol. Biol.* 17:691-699 (1991), which is hereby incorporated by reference in its entirety). Targeted expression of an introduced gene (transgene) is necessary when expression of the transgene could have detrimental effects if expressed throughout the plant. On the other hand, silencing a gene throughout a plant could also have negative effects. However, this problem could be avoided by localizing the silencing to a region by a tissue-specific promoter.

Nucleic acid constructs of the present invention include an operable 3' regulatory region, selected from among those which are capable of providing correct transcription termination and polyadenylation of mRNA for expression in the host cell of choice, operably linked to a nucleic acid molecule configured to silence BBTV. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313 (6005):810-812 (1985), which is hereby incorporated by reference in its entirety). Virtually any 3' regulatory region known to be operable in plants would be suitable for use in conjunction with the present invention.

The different components described supra can be ligated together to produce the expression systems which contain the nucleic acid constructs of the present invention, using well known molecular cloning techniques as described in Sambrook et al., *Molecular Cloning: A Laboratory Manual*, Second Edition Cold Spring Harbor, N.Y., Cold Spring Harbor Press (1989), and Ausubel et al. *Current Protocols in Molecular Biology*, New York, N.Y., John Wiley & Sons (1989), which are hereby incorporated by reference in their entirety.

Once the nucleic acid construct of the present invention has been prepared, it is ready to be incorporated into a host cell. Accordingly, another aspect of the present invention relates to a recombinant host cell containing one or more of the nucleic acid constructs of the present invention. Basically, this method is carried out by transforming a host cell with a nucleic acid construct of the present invention under conditions effective to achieve transcription of the nucleic acid molecule in the host cell. This is achieved with standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the nucleic acid under control of the promoter. Preferably, a nucleic acid construct of the present invention is stably inserted into the genome of the recombinant plant cell as a result of the transformation, although transient expression can serve an important purpose.

Plant tissue suitable for transformation includes leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue can be achieved by particle bombardment (Klein et al., "High-Velocity Microprojectiles for Delivering Nucleic Acids Into Living Cells," *Nature* 327:70-73 (1987), which is hereby incorporated by reference in its entirety), also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety.

In particle bombardment, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct of the present invention. As described supra, the Ti (or RI) plasmid of *Agrobacterium* enables the highly successful transfer of a foreign nucleic acid molecule into plant cells. A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety).

Yet another method of introduction is fusion of protoplasts with other entities, either minicells, cells, lysosomes, or other fusible lipid-surfaced bodies (Fraley et al., "Liposome-mediated Delivery of Tobacco Mosaic Virus RNA Into Tobacco Protoplasts: A Sensitive Assay for Monitoring Liposome-protoplast Interactions," *Proc. Natl. Acad. Sci. USA* 79:1859-63 (1982), which is hereby incorporated by reference in its entirety). The nucleic acid molecule may also be introduced into the plant cells by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). The precise method of transformation is not critical to the practice of the present invention. Any method that results in efficient transformation of the host cell of choice is appropriate for practicing the present invention.

Yet a further method for introduction is by use of known techniques for genome editing or alteration. Such techniques for targeted genomic insertion involve, for example, inducing a double stranded DNA break precisely at one or more targeted genetic loci followed by integration of a chosen transgene or nucleic acid molecule (or construct) during repair. Such techniques or systems include, for example, zinc finger nucleases ("ZFNs") (Urnov et al., "Genome Editing with Engineered Zinc Finger Nucleases," *Nat Rev Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat Rev Mol Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nat* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7): 397-405 (2013), each of which is hereby incorporated by reference in its entirety).

After transformation, the transformed plant cells must be regenerated. Plant regeneration from cultured protoplasts is described in Evans et al., *Handbook of Plant Cell Cultures*, Vol. 1, New York, N.Y., MacMillan Publishing Co. (1983); Vasil, ed., *Cell Culture and Somatic Cell Genetics of Plants*, Vol. I (1984) and Vol. III (1986), Orlando, Acad. Press; and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in their entirety.

Means for regeneration varies from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the neomycin phosphotransferae II ("nptII") gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene (Sambrook et al., *Molecular Cloning: A Laboratory Manual*, Cold Spring Harbor, N.Y., Cold Spring Harbor Press (1989), which is hereby incorporated by reference in its entirety).

In one embodiment, the transgenic plant is transformed with a bacterial artificial chromosome ("BAC"). A BAC is a cloning vector derived from the naturally occurring F factor of *Escherichia coli*. BACs can accept large inserts of a DNA sequence. BACs have a propensity for coming together to form contiguous stretches of DNA. A BAC "assembles" to a contig based on sequence alignment, if the BAC is sequenced, or via the alignment of its BAC fingerprint to the fingerprints of other BACs.

Accordingly, one aspect of the present invention relates to a plant or plant seed transformed with one or more nucleic acid constructs described herein. The present invention also encompasses the whole plant, or a component part of a plant, including shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same.

Suitable plants may be selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, *sorghum*, sugarcane, banana, *Arabidopsis thaliana, Saintpaulia, petunia, pelargonium*, poinsettia, *chrysanthemum*, carnation, *crocus*, marigold, daffodil, pine, *Medicago truncatula, Sandersonia aurantiaca, Populus trichocarpa*, and *zinnia*. Suitable plants as described herein may also be selected from *Arabidopsis thaliana, Populus trichocarpa, Zea mays, Sorghum bicolor, Oryza sativa* (rice), *Hordeum vulgare* (common barley), *Triticum aestivum* (wheat), *Nicotiana tabacum, petunia, Glycine max* (Soybean), cotton,

*Malus domestica* (Apple), *Brassica napus, Solanum tuberosum* (Potato), or *Solanum lycopersicum* (Tomato).

Accordingly, yet another aspect of the present invention relates to a method for promoting premature or precocious leaf senescence in a plant. This methods involves providing a transgenic plant or plant seed transformed with a nucleic acid construct effective in silencing expression of a S3H protein capable of causing leaf senescence in a plant; and growing the transgenic plant or the plant grown from the transgenic plant seed under conditions effective to promote premature or precocious leaf senescence in the transgenic plant or the plant grown from the transgenic plant seed.

In one embodiment, the plant is transformed. In another embodiment, a plant seed is transformed.

In one embodiment, the nucleic acid construct includes a nucleic acid molecule configured to silence S3H protein expression; a 5' DNA promoter sequence; and a 3' terminator sequence, where the nucleic acid molecule, the promoter, and the terminator are operatively coupled to permit expression of the nucleic acid molecule.

Suitable nucleic acid molecules and corresponding S3H protein sequence for use in accordance with the present invention are described above.

In one embodiment, the nucleic acid molecule is positioned in the nucleic acid construct to result in suppression or interference of endogenous mRNA encoding the S3H protein.

In one embodiment, the nucleic acid molecule includes an antisense nucleic acid molecule to a nucleic acid molecule encoding an S3H protein or a portion thereof.

In one aspect of the present invention, the nucleic acid construct results in suppression or interference of S3H protein expression by the nucleic acid molecule of the construct containing a dominant negative mutation and encoding a non-functional S3H protein.

In another aspect of the present invention, the nucleic acid construct results in interference of S3H protein expression by sense or co-suppression in which the nucleic acid molecule of the construct (e.g., that encoding S3H or a fragment thereof) is in a sense (5'→3') orientation. Co-suppression has been observed and reported in many plant species and may be subject to a transgene dosage effect or, in another model, an interaction of endogenous and transgene transcripts that results in aberrant mRNAs (Senior, "Uses of Plant Gene Silencing," *Biotechnology and Genetic Engineering Reviews* 15:79-119 (1998); Waterhouse et al., "Exploring Plant Genomes by RNA-Induced Gene Silencing," *Nature Review: Genetics* 4: 29-38 (2003), which are hereby incorporated by reference in their entirety). A construct with the nucleic acid molecule (or fragment thereof) in the sense orientation may also give sequence specificity to RNA silencing when inserted into a vector along with a construct of both sense and antisense nucleic acid orientations as described infra (Wesley et al., "Construct Design for Efficient, Effective and High-Throughput Gene Silencing in Plants," *Plant Journal* 27(6) 581-590 (2001), which is hereby incorporated by reference in its entirety).

In another embodiment of the present invention, the nucleic acid construct results in interference of S3H protein expression by the use of antisense suppression in which the nucleic acid molecule of the construct (e.g., that encoding S3H or a fragment thereof) is an antisense (3'→5') orientation. The use of antisense RNA to down-regulate the expression of specific plant genes is well known (van der Krol et al., *Nature*, 333:866-869 (1988) and Smith et al., *Nature*, 334:724-726 (1988), which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). In the target cell, the antisense nucleic acids hybridize to a target nucleic acid and interfere with transcription, and/or RNA processing, transport, translation, and/or stability. The overall effect of such interference with the target nucleic acid function is the disruption of protein expression (Baulcombe, "Mechanisms of Pathogen-Derived Resistance to Viruses in Transgenic Plants," *Plant Cell* 8:1833-44 (1996); Dougherty, et al., "Transgenes and Gene Suppression: Telling us Something New?," *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety). Accordingly, one aspect of the present invention involves a nucleic acid construct which contains an antisense nucleic acid molecule to a nucleic acid molecule encoding an S3H protein (or fragment thereof).

Such sense and antisense molecules could be readily generated based on the nucleotide sequences of S3H described above (e.g., SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and/or SEQ ID NO: 30).

RNA interference of S3H protein expression is also achieved in the present invention by the generation of double-stranded RNA ("dsRNA") through the use of inverted-repeats, segments of gene-specific sequences oriented in both sense and antisense orientations. In one embodiment of this aspect of the present invention, sequences in the sense and antisense orientations are linked by a third segment, and inserted into a suitable expression vector having the appropriate 5' and 3' regulatory nucleotide sequences operably linked for transcription. The expression vector having the modified nucleic acid molecule is then inserted into a suitable host cell or subject. In the present invention, the third segment linking the two segments of sense and antisense orientation may be any nucleotide sequence such as a fragment of the β-glucuronidase ("GUS") gene. In another embodiment of this aspect of the present invention, a functional (splicing) intron of the s3h gene may be used for the third (linking) segment, or, in yet another aspect of the present invention, other nucleotide sequences without complementary components in the s3h gene may be used to link the two segments of sense and antisense orientation (Chuang et al., "Specific and Heritable Genetic Interference by Double-Stranded RNA in *Arabidopsis thaliana,*" *Proc. Nat'l Academy of Sciences USA* 97(9): 4985-4990 (2000); Smith et al., "Total Silencing by Intron-Spliced Hairpin RNAs," *Nature* 407:319-320 (2000); Waterhouse et al., "Exploring Plant Genomes by RNA-Induced Gene Silencing," *Nature Review: Genetics* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety). In any of the embodiments with inverted repeats of S3H protein, the sense and antisense segments may be oriented either head-to-head or tail-to-tail in the construct.

Another aspect of the present invention involves using hairpin RNA ("hpRNA") which may also be characterized as dsRNA. This involves RNA hybridizing with itself to form a hairpin structure that comprises a single-stranded loop region and a base-paired stem. Though a linker may be used between the inverted repeat segments of sense and antisense sequences to generate hairpin or double-stranded RNA, the use of intron-free hpRNA can also be used to achieve silencing of S3H protein expression.

Alternatively, in another aspect of the present invention, a plant may be transformed with constructs encoding both sense and antisense orientation molecules having separate promoters and no third segment linking the sense and antisense sequences (Chuang et al., "Specific and Heritable Genetic Interference by Double-Stranded RNA in *Arabidopsis thaliana*," *Proc. Nat'l Academy of Sciences USA* 97(9): 4985-4990 (2000); Waterhouse et al., "Exploring Plant Genomes by RNA-Induced Gene Silencing," *Nat Rev Genet.* 4:29-38 (2003); Wesley et al., "Construct Design for Efficient, Effective and High-Throughput Gene Silencing in Plants," *Plant Journal* 27(6):581-590 (2001), which are hereby incorporated by reference in their entirety).

Altering expression (e.g., inhibition of, or interference with, endogenous expression) of S3H can also be accomplished using known techniques for targeted alteration of genes, such as ZFNs, TALENs, CRISPR-associated endonucleases, which are described above.

Another aspect of the present invention relates to a method for delaying leaf senescence in a plant. This method involves transforming a plant cell with a nucleic acid molecule encoding a S3H capable of causing leaf senescence in a plant operably associated with a promoter to obtain a transformed plant cell, where expression of the nucleic acid molecule in the plant cell causes delayed leaf senescence; and regenerating a plant from the transformed plant cell under conditions effective to delay leaf senescence in the plant.

In one embodiment, such transforming includes transforming the plant cell with a nucleic acid construct comprising the nucleic acid molecule; a 5' heterologous DNA promoter sequence; and a 3' terminator sequence, where the nucleic acid molecule, the DNA promoter sequence, and the terminator sequence are operatively coupled to permit transcription of the nucleic acid molecule.

In one embodiment, the method involves regenerating a plant from the transformed plant cell and inducing the promoter under conditions effective to cause delayed leaf senescence in the plant.

Yet another aspect of the present invention relates to a method of making a mutant plant having a decreased level of S3H protein compared to that of a non-mutant plant, where the mutant plant displays a premature or precocious leaf senescence phenotype relative to a non-mutant plant. This method involves providing at least one cell of a non-mutant plant containing a gene encoding a functional S3H protein and treating the at least one cell of a non-mutant plant under conditions effective to inactivate said gene, thereby yielding at least one mutant plant cell containing an inactivated S3H protein encoding gene. This method also involves propagating the at least one mutant plant cell into a mutant plant, where the mutant plant has a decreased level of S3H protein compared to that of the non-mutant plant and displays a premature or precocious leaf senescence phenotype relative to a non-mutant plant.

In one embodiment, this method involves providing at least one cell of a non-mutant plant containing a gene encoding a functional S3H protein. Next, the at least one cell of a non-mutant plant is treated under conditions effective to inactivate the gene, thereby yielding at least one mutant plant cell containing an inactivated S3H gene. The at least one mutant plant cell is then propagated into a mutant plant, where the mutant plant has a decreased level of S3H protein compared to that of the non-mutant plant and displays a delayed leaf senescence phenotype relative to a non-mutant plant.

In other embodiments of this method of making a mutant plant, the functional S3H protein can be any S3H protein from a wide variety of plants as described herein supra.

In another embodiment of this method of making a mutant plant, the treating step involves subjecting the at least one cell of the non-mutant plant to a chemical mutagenizing agent under conditions effective to yield at least one mutant plant cell containing an inactive S3H gene. Suitable chemical mutagenizing agents can include, for example, ethylmethanesulfonate.

In another embodiment of this method of making a mutant plant, the treating step involves subjecting the at least one cell of the non-mutant plant to a radiation source under conditions effective to yield at least one mutant plant cell containing an inactive S3H gene. Suitable radiation sources can include, for example, sources that are effective in producing ultraviolet rays, gamma rays, or fast neutrons.

In another embodiment of this method of making a mutant plant, the treating step involves inserting an inactivating nucleic acid molecule into the gene encoding the functional S3H protein or its promoter under conditions effective to inactivate the gene. Suitable inactivating nucleic acid molecules can include, for example, a transposable element. Examples of such transposable elements include, but are not limited to, an Activator (Ac) transposon, a Dissociator (Ds) transposon, or a Mutator (Mu) transposon.

In yet another embodiment of this method of making a mutant plant, the treating step involves subjecting the at least one cell of the non-mutant plant to *Agrobacterium* transformation under conditions effective to insert an *Agrobacterium* T-DNA sequence into the gene, thereby inactivating the gene. Suitable *Agrobacterium* T-DNA sequences can include, for example, those sequences that are carried on a binary transformation vector of pAC106, pAC161, pGABI1, pADIS1, pCSA110, pDAP101, derivatives of pBIN19, or pCAMBIA plasmid series.

In still another aspect of this method of making a mutant plant, the treating step involves subjecting the at least one cell of the non-mutant plant to site-directed mutagenesis of the S3H gene or its promoter under conditions effective to yield at least one mutant plant cell containing an inactive S3H gene. The treating step can also involve mutagenesis by homologous recombination of the S3H gene or its promoter, targeted deletion of a portion of the S3H gene sequence or its promoter, and/or targeted insertion of a nucleic acid sequence into the S3H gene or its promoter. The various plants that can be used in this method are the same as those described supra with respect to the transgenic plants and mutant plants. Other embodiments of the present invention relate to mutant plants produced by this method, as well as mutant plant seeds produced by growing the mutant plant under conditions effective to cause the mutant plant to produce seed.

Accordingly, another aspect of the present invention relates to a mutant plant comprising an inactivated gene encoding S3H protein, where the mutant plant displays a premature or precocious leaf senescence phenotype, relative to a non-mutant plant.

Another aspect of the present invention relates to a method of inducing or promoting pathogen resistance in plants. This method involves providing a transgenic plant or plant seed transformed with a nucleic acid construct effective in silencing expression of a S3H protein capable of causing leaf senescence in a plant; and growing the transgenic plant or the plant grown from the transgenic plant seed under conditions effective to induce or promote pathogen resistance in the transgenic plant or the plant grown from the transgenic plant seed.

In one embodiment, a transgenic plant is provided. In another embodiment, a transgenic plant seed is provided.

Imparting disease or pathogen resistance or enhancing disease or pathogen resistance refers to an increase in the ability of a plant to prevent pathogen infection or pathogen-induced symptoms. Pathogen resistance may be increased compared to, for example, an unmodified or non-transgenic plant. Pathogen resistance can be increased resistance relative to a particular pathogen species or genus or can be increased resistance to all pathogens (e.g., systemic acquired resistance).

A further aspect of the present invention that is contemplated relates to a method of identifying a candidate plant suitable for breeding that displays a delayed senescence phenotype and or enhanced pathogen resistance. This method involves providing a candidate plant; analyzing the candidate plant for the presence, in its genome, of a gene encoding an S3H protein; identifying, based on said analyzing, a candidate plant suitable for breeding that includes in its genome, a gene encoding an S3H protein; and breeding the identified plant with at least one other plant.

In one embodiment, analyzing the candidate plant for the presence, in its genome, of a gene encoding an S3H protein involves isolating genomic DNA from the plant, germplasm, pollen, or seed of the plant; analyzing genomic DNA from the plant, germplasm, pollen, or seed of the plant for the presence of the gene encoding the S3H protein; and detecting the gene encoding the S3H protein.

In one embodiment, the breeding involves crossing, making hybrids, backcrossing, self-crossing, double haploid breeding, and/or combinations thereof.

In one embodiment, a transgenic plant transformed with a nucleic acid molecule that encodes an S3H protein is provided as the candidate plant. In one embodiment, providing the transgenic plant involves transforming a plant or plant seed with a nucleic acid construct according to the present invention and growing the transgenic plant or a plant grown from the transgenic plant seed under conditions effective to express the nucleic acid molecule in the transgenic plant or said plant grown from the transgenic plant seed.

EXAMPLES

Example 1—Plant Materials and Growth Conditions

*Arabidopsis thaliana* ecotype Col-0 was used as WT for all experiments. The T-DNA insertion line SALK_059907 was obtained from *Arabidopsis* Biological Resource Center (ABRC). Seeds were sown on Petri dishes containing MS with 0.7% w/v phytoagar and appropriate antibiotics and kept at 4° C. for 2 days before being moved to a growth chamber. Seedlings with two true leaves were transplanted to Cornell mix soils (3 parts peat moss: 2 parts vermiculite: 1 part perlite). WT, mutant and/or transgenic plants were grown side by side in the same tray to minimize possible variation of growth conditions. Plants were grown in 22° C. growth chamber with 60% relative humidity, under constant light (120 µmol m$^2$ sec$^{-1}$ light from a mixture of fluorescent and incandescent bulbs).

Example 2—Identification of T-DNA Insertion s3h Plants

Gene-specific primers G2563, G2564 (all the primers used in this research are listed in FIG. 1E) and T-DNA left border primer G2325 (LB1) were used to identify homozygous mutant plants of s3h.

Example 3—Chemicals and SA Treatment

All chemicals used in this research were purchased from Sigma-Aldrich (St. Louis, Mo.), unless otherwise stated. Col-0 plants (25 DAG) were sprayed with 5 mM SA in 0.005% Silwet L-77 (Lehele Seeds, Tex.) or only 0.005% Silwet L-77 (mock). All rosette leaves of individual plants for RNA extraction were collected at different time points after the spray.

Example 4—Constructs (i) The coding sequence of S3H, which was PCR amplified with S3H-specific primers G2563 and G2564, was cloned into pGEM-T easy vector (Promega, Madison, Wis.), released with HindIII and PstI, and subcloned to the binary vector pGL800 (Zhou et al., "An *Arabidopsis* Mitogen-Activated Protein Kinase Cascade, MKK9-MPK6, Plays a Role in Leaf Senescence," *Plant Physiol.* 150(1):167-177 (2009), which is hereby incorporated by reference in its entirety) to form pGL3135 that allows the overexpression of S3H in plants. (ii) The DNA fragment released from EcoRI-digestion of BAC F7L13 DNA (obtained from ABRC) contained the whole S3H gene including its promoter region and was cloned into the binary vector pPZP211 at EcoRI site to form pGL3228 for the complementation of s3h. (iii) To produce His-tagged S3H recombinant protein, the open reading frame of S3H was PCR amplified using a pair of primers, S3H_BamHI and S3H_HindIII, and was cloned into pET28a (Novagen, Madison, Wis.) to form pET28a-S3H. All constructs were verified by DNA sequencing.

Example 5—Chlorophyll Contents, $F_v/F_m$ Assay and Survival Curves

Chlorophyll was extracted and quantified as described previously (He & Gan, "A Gene Encoding an Acyl Hydrolase Is Involved in Leaf Senescence in *Arabidopsis*," *Plant Cell* 14(4):805-815 (2002), which is hereby incorporated by reference in its entirety). Fluorescence in leaves was measured using a portable chlorophyll fluorometer (model: OS1-FL) according to the manufacturer's instructions (Opti-Sciences, Tyngsboro, Mass.). The ratio of variable fluorescence to maximal fluorescence ($F_v/F_m$) for each leaf was quantified directly using the fluorometer's test mode 1. The survival curve assay was based on visual observation of leaf yellowing. The completely yellowed leaf was regarded as a dead leaf. The survival rate of WT, s3h and S3HOE1 plants were counted from 20 DAG to 70 DAG.

Example 6—Transcript Analyses

Total RNA extraction and RNA blot analysis were performed as described previously (He & Gan, "A Gene Encoding an Acyl Hydrolase Is Involved in Leaf Senescence in *Arabidopsis*," *Plant Cell* 14(4):805-815 (2002), which is hereby incorporated by reference in its entirety). The DNA templates for probe labeling were amplified by the following different pairs of primers: S3H, G2956 and G2957; AtNAP, G3149 and G3150; SAG12, G10 and G246; SAG13, G9 and G16; EDS1, EDS1F and EDS1R; PAD4, PAD4F and PAD4R; PR1, PR1F and PR1R (FIG. 1E). The ethidium bromide staining of the RNA gels was used to show approximate amount of total RNA loading on each lane.

Example 7—Transformation

The binary vectors were electroporated into the *Agrobacterium tumefaciens* strain ABI1 and transformed into the WT or s3h mutant via the floral dip method (Clough & Bent, "Floral Dip: A Simplified Method for *Agrobacterium*-Mediated Transformation of *Arabidopsis thaliana*," Plant J. 16(6):735-743 (1998), which is hereby incorporated by reference in its entirety). Approximately 40 kanamycin-resistant T1 transgenic lines for each transgene were selected. Phenotypic analyses were performed in the T2 generation and confirmed in the T3 generation. Homozygous plants were used in all experiments.

Example 8—Metabolite Analysis

All rosette leaves of 25 DAG and 35 DAG plants of WT, s3h and S3HOE1 transgenic plants were collected for analysis of free SA, 2,3-DHBA and 2,5-DHBA using a protocol described previously (Pan et al., "Simultaneous Quantification of Major Phytohormones and Related Compounds in Crude Plant Extracts by Liquid Chromatography-Electrospray Tandem Mass Spectrometry," *Phytochemistry* 69(8): 1773-1781 (2008), which is hereby incorporated by reference in its entirety). 10 µL extracts were injected for analysis using a liquid chromatography mass-spectrometry (LC-MS) (Quantum Access; Thermo Scientific, Waltham, Mass.) as described (Thaler et al., "Salicylate-Mediated Interactions Between Pathogens and Herbivores," *Ecology* 91(4):1075-1082 (2010), which is hereby incorporated by reference in its entirety). The SAG, 2,3-DHBX, 2,3-DHBG, 2,5-DHBX and 2,5-DHBG samples with internal standard [$^2$H4]SA (CDN Isotopes, Pointe-Claire, QC, Canada) were extracted as described previously (Zhang et al., "An Engineered Monolignol 4-o-Methyltransferase Depresses Lignin Biosynthesis and Confers Novel Metabolic Capability in *Arabidopsis*," *Plant Cell* 24(7):3135-3152 (2012), which is hereby incorporated by reference in its entirety). Glycosides were separated on a C18 reversed phase column (Gemini-NX, 3 µm, 150×4.6 mm, Phenomenex, Torrance, Calif.) and the following solvent gradient (solvent A: 0.1% formic acid in water; solvent B: 0.1% formic acid in acetonitrile): initial 5% B to 75% B at 45 min, and 45-52 min 75% B at a flow rate of 0.2 mL min$^{-1}$. The MS detector was equipped with an electrospray ionization (ESI) probe operated under negative ionization conditions: spray voltage 4.0 kV, capillary temperature 360° C., sheath gas (N$_2$) pressure 15 arbitrary units, auxiliary gas (N$_2$) pressure 10 arbitrary units. Mass spectra were recorded in full scan mode (m/z 100 to m/z 1000) to determine molecular ions [M-H]$^-$ used for glycoside quantification. Glycoside identity was verified by comparing UV absorption, retention time, and collision-induced dissociation (CID energy 20 V, CID gas (Ar) pressure 1.5 mTorr) fragmentation of selected molecular ions with published data (Bartsch et al., "Accumulation of Isochorismate-Derived 2,3-Dihydroxybenzoic 3-O-beta-D-Xyloside in *Arabidopsis* Resistance to Pathogens and Ageing of Leaves," *J. Biol. Chem.* 285(33):25654-25665 (2010), which is hereby incorporated by reference in its entirety). Five to six biological replicates of each genotype were analyzed.

Example 9—S3H Recombinant Protein Expression in and Purification from *Escherichia coli*

The construct pET28a-S3H was introduced into *E. coli* BL21 (DE3, pLys3, Invitrogen, Carlsbad, Calif.). The bacterial cells containing pET28a-S3H were induced with 0.5 mM isopropyl β-D-1-thiogalactoside (IPTG) for 24 hr at 18° C., and were collected and disrupted by sonication in lysis buffer (20 mM Tris-Cl, pH7.5, 2 mM EDTA, 2 mM β-mercaptoethanol, 1 mM PMSF, 10 mM Imidazole, 0.1% Triton X-100, 20 mM sodium ascorbate). All subsequent purification procedures involving His-Bind® resin were performed at 4° C. according to the manufacturer (Novagen, Madison, Wis.). The recombinant protein concentration was quantified using Quick Start Bradford Dye Reagent (Biorad, Hercules, Calif.). 2 mM DTT was added to the enzyme solution and the protein was immediately kept in a −80° C. refrigerator.

Example 10—Enzyme Assay

The enzyme assay was performed using a method modified from Satio et al. (Saito et al., "Direct Evidence for Anthocyanidin Synthase as a 2-Oxoglutarate-Dependent Oxygenase: Molecular Cloning and Functional Expression of cDNA From a Red Forma of *Perilla frutescens*," *Plant J.* 17(2):181-189 (1999), which is hereby incorporated by reference in its entirety). The reaction mixture (100 µl) contained 5 mM DTT, 4 mM sodium ascorbate, 1 mM 2-oxoglutaric acid, 0.4 mM FeSO$_4$, 0.1 mg/ml catalase, 50 mM Tris-Cl pH8.0 or other buffer, 8-15 µg recombinant protein, various concentrations of SA. To determine the optimal temperature and pH for enzyme activity of S3H, the protein was incubated with 200 µM SA substrate in Tris-Cl buffer (pH8.0) at different temperatures for 15 min; or 500 µM SA substrate, in 50 mM Sodium citrate, Tris-Cl and Glycine buffers with different pH at 40° C. for 15 min. For enzyme kinetics analysis, various substrate SA concentrations ranging from 10 to 500 µM were used and the incubation proceeded for 6 min with pH 6.0. All the reactions were started by adding the enzyme and stopped by adding 100 µl 50% (v/v) acetonitrile and heated at 99° C. for 1 min to pellet the protein. After centrifugation for 10 min at full speed, the samples were resolved on a Gemini C18 reversephase column (Phenomenex, Torrance, Calif.) in the following solvent gradient (solvent A: 0.2% acetic acid in water; solvent B: 0.2% acetic acid in acetonitrile): initial 5% B to 48% B at 10 min, and 11-15 min 51% B, then 16-21 min 100% B at a flow rate of 1 mL min$^{-1}$. For MS analysis, an HP 1100 series II LC system (Agilent, Danbury, Conn.) was coupled to a Bruker Esquire ion-trap mass spectrometer (MSD trap XCT system) equipped with an electrospray ionization source. Negative ionization was attained using an ion source voltage of 3.5 kV, a corona of 4000 nA, and a skimmer at a voltage of 40 V. Nebulization was aided by a coaxial nitrogen sheath gas at 50 p.s.i. pressure. Desolvation was insured by a counter current nitrogen flow set at 7 p.s.i. pressure, with both the capillary and vaporizer temperature at 300° C. Mass spectra were recorded over 15 to 800 m/z in the negative mode. $K_m$ and $V_{max}$ were determined by Graphpad Prism 5 software using non-linear regression for Michaelis-Menten equation.

Sequence described herein can be found in the GenBank/EMBL databases under the following accession numbers, each of which is hereby incorporated by reference in its entirety: AT4G10500 (S3H, SAG108), AT3G51240 (F3H), AT2G14610 (PR1), AT1G69490 (AtNAP), AT5G45890 (SAG12), AT2G29350 (SAG13), AT3G48090 (EDS1), AT3G52430 (PAD4), AT1G74710 (ICS1) and AT1G18870 (ICS2), AT2G43840 (UGT74F1) and AT2G43820 (UGT74F2), AT3G11480 (BSMT1); AT2G23620 (AtMES1), AT2G23600 (AtMES2), AT2G23580 (AtMES4), AT2G23560 (AtMES7), AT4G37150 (AtMES9).

Example 11—Pathogen Test

The pathogen test was essentially followed the method described by Katagiri et al., "The *Arabidopsis Thaliana-Pseudomonas Syringae* Interaction," *Arabidopsis Book* 1:e0039 (2002), which is hereby incorporated by reference in its entirety. The plants used for pathogen test were gown at 20° C. growth chamber with 70-80% relative humidity, under 14 hrs light (120 µmol m$^{-2}$ sec$^{-1}$ of fluorescent light). The adult leaves at same position of 4-week plants were used for pathogen inoculation. The bacterial strain *Pseudomonas syringae* pv tomato DC 3000 was diluted to OD600 0.002 (1×10$^6$ cfu/mL) and injected in the middle of a leaf with a needleless syringe. 0 (shortly after inoculation), 1 or 3 days post inoculation, the leaf was washed for 1 min in 70% ethanol and 1 min in water then leaf discs were cut using a cork borer immediately. Subsequently, three leaf discs from three plants were put into 100 µL of distilled water and were immediately homogenized. Appropriate dilutions were plated on Kings B plates and incubated for approximately 2 days at 28° C., and then the colony-forming units for each dilution of each sample were counted.

Example 12—SAG108/S3H is a Senescence-Associated Gene and can be Induced by SA

At4g10500 was initially identified as a senescence-associated gene called SAG108 from previous transcriptomic analyses of leaf senescence in *Arabidopsis* (Guo et al., "Transcriptome of *Arabidopsis* Leaf Senescence," *Plant Cell Environ.* 27(5):521-549 (2004), which is hereby incorporated by reference in its entirety) and was found to encode a functional S3H as described herein. RNA gel blot analysis revealed that the S3H transcript accumulated in senescing leaves but was barely detectable in non-senescence leaves, which showed similar expression pattern to a known senescence-associated transcription factor AtNAP (FIG. 1A) (Guo & Gan, "AtNAP, a NAC Family Transcription Factor, Has an Important Role in Leaf Senescence," *Plant J.* 46(4): 601-612 (2006), which is hereby incorporated by reference in its entirety). The S3H expression was also readily inducible after SA treatment for 6 hours, with a similar induction pattern to that of PR1 which is well known for its inducibility by SA (FIG. 1B) (Uknes et al., "Acquired Resistance in *Arabidopsis,*" *Plant Cell* 4(6):645-656 (1992), which is hereby incorporated by reference in its entirety).

Example 13—S3H Regulates Onset and Progression of Leaf Senescence

Figures 3A, 3B:
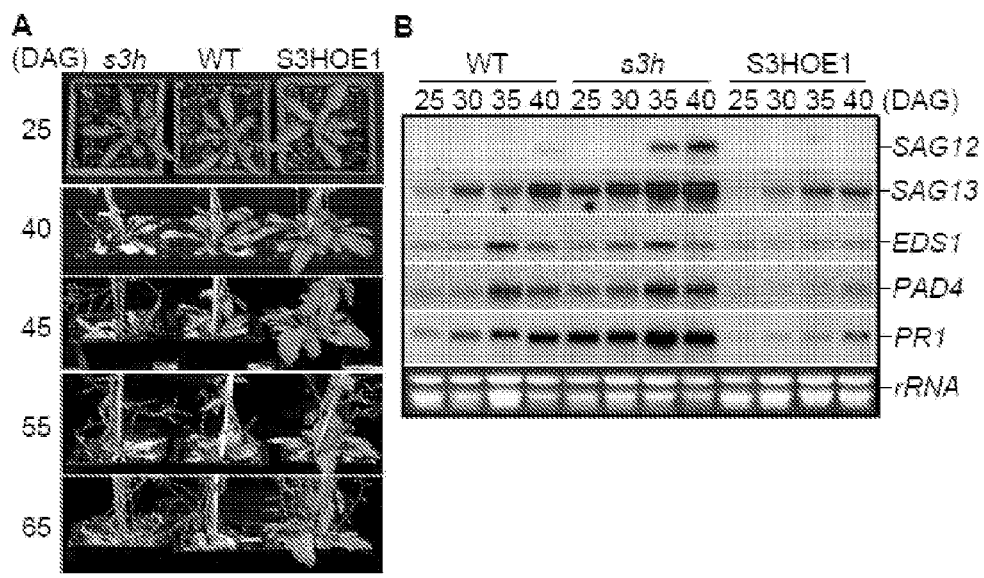
FIGS. 3A-3B show experimental results demonstrating phenotypic and transcriptional changes in s3h and S3HOE1 plants compared with those of WT.
Figures 6A, 6B, 6C:
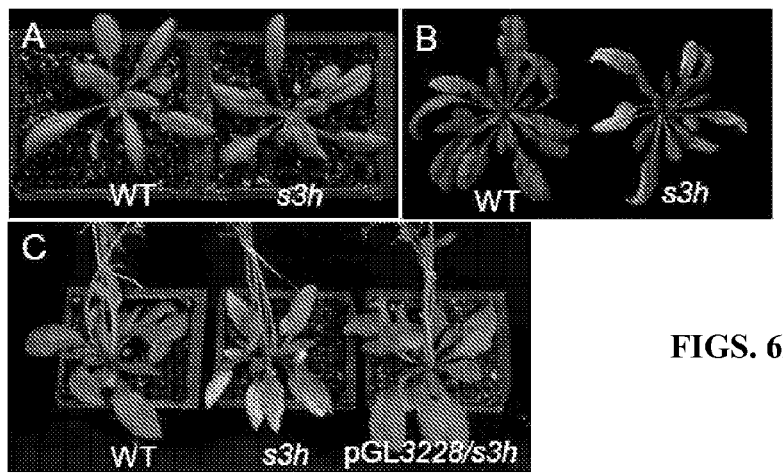
FIGS. 6A-6C are images of experimental results relating to accelerated leaf senescence in the s3h knockout mutant and its complementation test with S3H genomic DNA.

To investigate the biological function of S3H, a T-DNA insertion line (SALK_059907) was characterized. This line contains a T-DNA insertion in the 2$^{nd}$ exon of S3H that completely abolishes S3H expression in homozygous mutant plants as revealed by RNA gel blot analysis (FIGS. 1C and D). The s3h knockout plants exhibited a remarkably accelerated leaf senescence phenotype characterized by lower chlorophyll content and reduced $F_v/F_m$ ratios compared with those of age-matched wild type (WT) (FIGS. 2A-C and FIG. 6B); however, the early stages of growth and development of the plants that were 25 DAG old (days after germination of seeds) appeared to be normal (FIG. 3A and FIG. 6A). The $F_v/F_m$ ratio reflects the activity of photosystem II.

The leaf senescence program in s3h mutants was accelerated in two aspects. First, the senescence rate was accelerated. It took 9.5 days on average for senescence to progress from the leaf tip to the petiole in WT but only 2.7 days in the s3h leaves (FIG. 2G). Second, the onset of senescence was earlier (visible sign of yellowing at the leaf tip); in s3h the onset occurred 16.8 days after emergence (DAE) of leaves, compared to 19.2-DAE in WT (FIG. 2G). The earlier onset of senescence and the faster senescence progression are also observed from the leaf survival curves (FIG. 2H). The s3h null mutation is responsible for the phenotype because a construct (pGL3228) carrying an intact S3H (including its promoter region) restored s3h to WT (FIG. 6C).

Figure 7:
FIG. 7 is an image of an RNA gel blot analysis of constitutive S3H overexpression lines (S3HOEs). The $1^{st}$ through $6^{th}$ rosette leaves were harvested from 35-DAG transgenic plants for RNA extraction and RNA gel blot analysis.

In contrast, when S3H was constitutively overexpressed in WT under the direction of the CaMV 35S promoter (FIG. 7), leaf senescence was significantly delayed (FIGS. 2D-F and FIG. 3A), but the flowering time was not altered (FIG. 3A). As shown in FIG. 2D, leaves of the 45-DAG WT plants had been senescing but leaves of the age-matched S3H overexpression transgenic plants remained green. Also, it took 14.6 days for senescence to progress from the leaf tip to the petiole in the S3H overexpression lines (S3HOE) compared to 9.5 and 2.7 days in WT and s3h, respectively (FIG. 2G). The onset of leaf senescence in S3HOE, which occurred at 21.2 DAE, was also delayed compared to 19.2 DAE in WT and 16.8 DAE in s3h, respectively (FIG. 2G).

Example 14—Expression of Senescence-Associated Genes and Defense-Related Genes is Accelerated in s3h and Delayed in S3HOE Lines In addition to the above phenotypic characterization, RNA gel blot analyses of two widely used leaf senescence marker genes SAG12 and SAG13, and three SA signaling marker genes EDS1, PAD4 and PR1 was performed in leaves of WT, s3h and S3HOE lines at different ages (FIG. 3B). The highly senescence-specific SAG12 transcripts were readily detectable in the rosette leaves of 35-DAG s3h mutant and 40-DAG WT plants, but were not detected in the S3HOE1 plants at 40 DAG. Likewise, the SAG13, PR1, EDS1 and PAD4 were also found to be precociously expressed in the s3h mutants but significantly suppressed in the overexpression lines. These data suggest that S3H regulates senescence-associated genes and genes involved in SA signaling.

Example 15—S3H Mediates the Conversion of SA to 2,3-DHBA in Planta

The metabolite profiles of SA in young and senescing plants of WT, s3h and S3HOE lines were analyzed using LC-MS/MS. The levels of free SA, SA sugar conjugates, SA derivatives including 2,3-DHBA, 2,5-DHBA and their sugar conjugates are summarized in FIG. 4H.

The free SA levels in rosette leaves of young (Y) or senescing (S) s3h mutant plants were 625% and 710% of those of WT, whereas the free SA concentrations in rosette leaves of young or senescing S3HOE1 lines were reduced to only 10-12.5% of those in WT. Similarly, the concentrations of SA glucosides (SAG) in leaves of young or senescing s3h mutant plants were also increased to 267% and 317% of those of WT, respectively. However, the SAG levels were reduced to undetectable levels in leaves of both young and senescing S3HOE1 lines (FIG. 4H).

In contrast to SA, the levels of free 2,3-DHBA and 2,5-DHBA, two major catabolites of SA in *Arabidopsis*, were too low to be detected but the levels of their sugar conjugates were drastically changed. In s3h mutant, free SA and SAG were accumulated to very high levels as mentioned above. However, the total levels of 2,3-DHBA sugar conjugates (2,3-DHBX+2,3-DHBG) were not detected in the s3h mutant while the total levels of 2,5-DHBA sugar conjugates (2,5-DHBX+2,5-DHBG) were increased to 113% and 162% of those of WT in the young leaves and senescing leaves, respectively. By contrast, in the S3HOE1 leaves, the levels of both 2,3-DHBA sugar conjugates (2,3-DHBX+2,3-DHBG) were significantly increased to 187% and 224% of those of rosette leaves of WT (Y or S), respectively, but the levels of 2,5-DHBA sugar conjugates (2,5-DHBX+2,5-DHBG) were significantly reduced to 43% and 40% of those of WT, respectively (FIG. 4H). These data strongly suggest that S3H converts SA to 2,3-DHBA in vivo.

Example 16—Recombinant S3H Possesses SA 3- and 5-Hydroxylase Activities

Figures 4A, 4B, 4C, 4D:
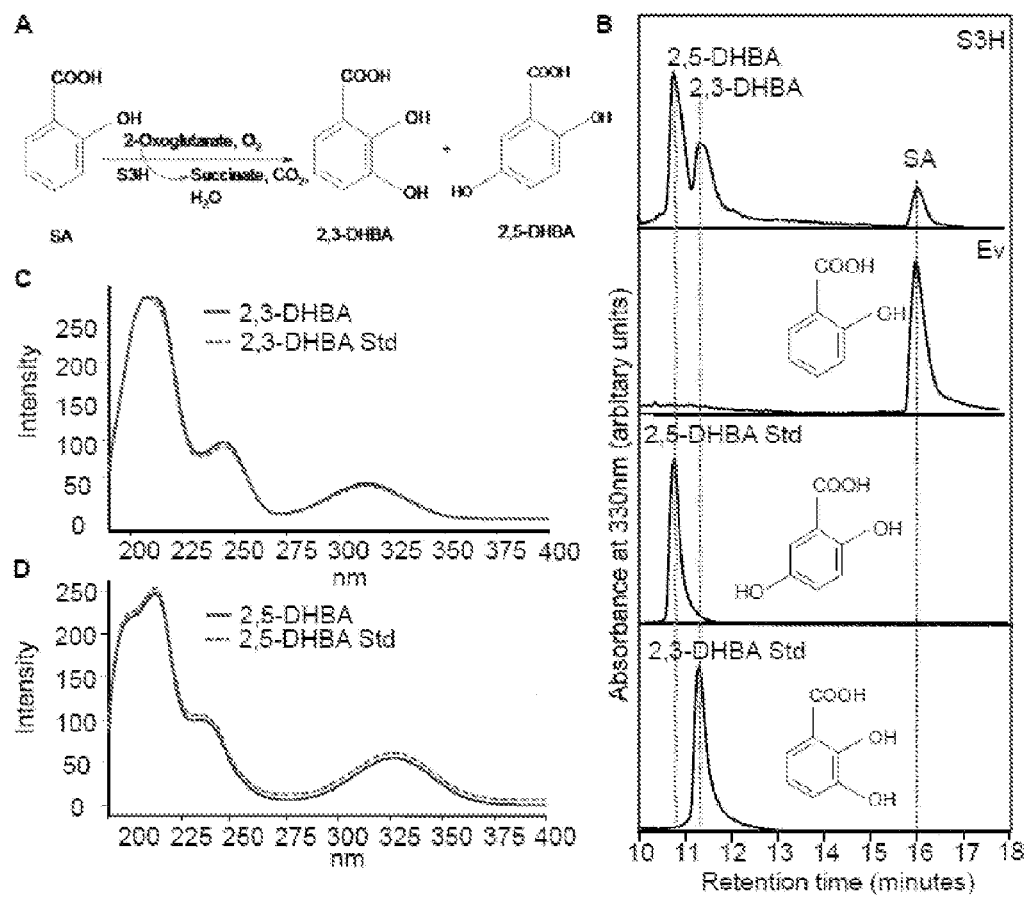
Figures 4E, 4F, 4G:
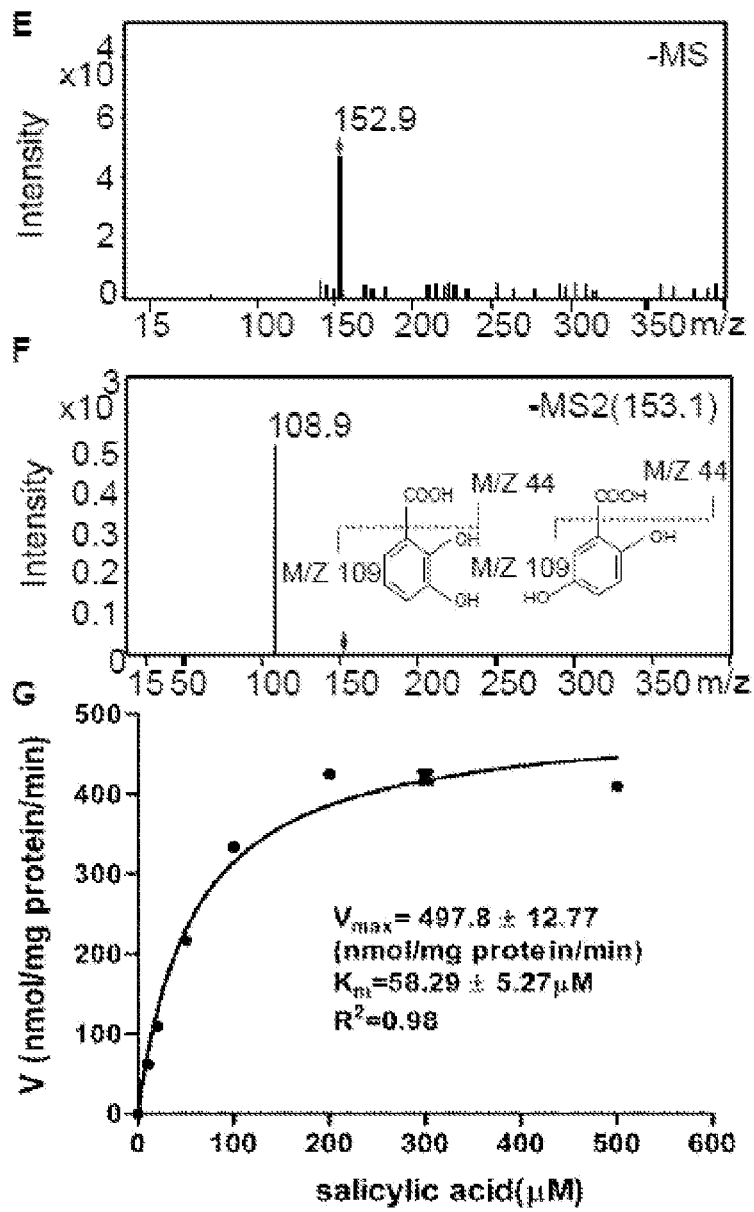

Sequence analyses revealed that S3H encodes a protein with similarity to the 2OG-Fe(II) oxygenase family enzymes (including a well-known F3H enzyme) that have a conserved catalytic domain Pfam PF03171 (FIGS. 8 and 9) (Wisman et al., "Knock-out Mutants From an En-1 Mutagenized *Arabidopsis thaliana* Population Generate Phenylpropanoid Biosynthesis Phenotypes," *Proc. Nat'l Acad. Sci. U.S.A.* 95(21):12432-12437 (1998), which is hereby incorporated by reference in its entirety). Because the above phytochemical analyses implied that S3H catalyzes SA to produce 2,3-DHBA, biochemical analyses was performed to confirm the enzymatic activity using recombinant S3H enzyme overproduced in and purified from *E. coli*. To eliminate non-enzymatic oxidation of SA due to hydroxyl radicals (.OH), catalase was added to each reaction to remove the hydroxyl radicals. The recombinant S3H enzyme converted SA to both 2,3-DHBA and 2,5-DHBA in the presence of ferrous iron, ascorbate, 2-oxoglutarate (2OG) and catalase (FIGS. 4A and B). The 2,3-DHBA and 2,5-DHBA produced by the recombinant S3H have the same retention times and UV spectra as those of the 2,3-DHBA and 2,5-DHBA authentic standards, respectively (FIG. 4B-D). The mass spectra of produced 2,3-DHBA and 2,5-DHBA were also characterized by LC-MS/MS (FIG. 4E-F). The enzyme activity increased with the increase of temperature from 4° C. to 40° C. and decreased from 40° C. to 50° C., suggesting the optimal temperature of this enzyme is approximate 40° C. (FIG. 10A). The effect of pH on the enzyme activities was also tested and the optimal pH was 6.0 under the test conditions (FIG. 10B). The apparent $K_m$ value for SA of the recombinant S3H was determined to be 58.29 µM at the optimal temperature and pH conditions (FIG. 4G). The substrate specificity of the recombinant S3H was also investigated using benzoic acid and anthranilic acid, two chemicals with similar structures to SA. The S3H enzyme did not have detectable activity after 30-min reaction under the same conditions as those for SA (Table 1), suggesting that the recombinant S3H enzyme has high substrate specificity.

TABLE 1

Substrate Specificity of S3H[a]

| Substrates | Specific activity (nmol mg$^{-1}$ min$^{-1}$) | $K_m$ (µM) | $V_{max}$ (nmol mg$^{-1}$ min$^{-1}$) | $K_{cat}/K_m$ (M$^{-1}$s$^{-1}$) |
|---|---|---|---|---|
| Salicylic acid | 78.06 ± 9.75 | 58.29 ± 5.27 | 497.8 ± 12.77 | 6.09 × 10$^3$ |
| Benzoic acid | n.d.[b] | | | |
| Anthranilic acid | n.d | | | |

[a]The specific activity was measured from the reaction at pH 6.0 and 40° C. for 30 min, the data represent the mean ± SE of three replicates. Kinetic parameters were obtained from the reactions at pH 6.0 and 40° C. for 6 min as described in methods, the data represent the mean ± SE of four replicates
[b]n.d. not detectable.

The data described herein has revealed a novel negative feedback regulation mechanism by which plants modulate their endogenous SA levels at the onset of and during leaf senescence and has provided strong molecular genetic evidence that S3H, via modulating SA levels, has a pivotal role in controlling leaf senescence.

Elucidation of biosynthesis and catabolism of SA is important for understanding its biological functions. The PAL and IC pathway have been well studied and proposed to be the two main routes responsible for SA biosynthesis (Dempsey et al., "Salicylic Acid Biosynthesis and Metabolism," *Arabidopsis Book* 9:e0156 (2011), which is hereby incorporated by reference in its entirety). However, the catabolism of SA is less understood (Dempsey et al., "Salicylic Acid Biosynthesis and Metabolism," *Arabidopsis Book* 9:e0156 (2011), which is hereby incorporated by reference in its entirety). This identification and characterization of S3H uncovered a negative feedback regulatory mechanism by which plants regulate SA levels. Briefly, S3H is induced by SA and the induced S3H enzyme in turn hydrolyzes SA to 2,3-DHBA, a de-activated form of SA (Bartsch et al., "Accumulation of Isochorismate-Derived 2,3-Dihydroxybenzoic 3-O-beta-D-Xyloside in *Arabidopsis* Resistance to Pathogens and Ageing of Leaves," *J. Biol. Chem.* 285(33): 25654-25665 (2010) and Hennig et al., "Interconversion of the Salicylic Acid Signal and its Glucoside in Tobacco," *Plant J.* 4(4):593-600 (1993), each of which is hereby incorporated by reference in its entirety), to prevent overaccumulation of SA.

Figure 11:
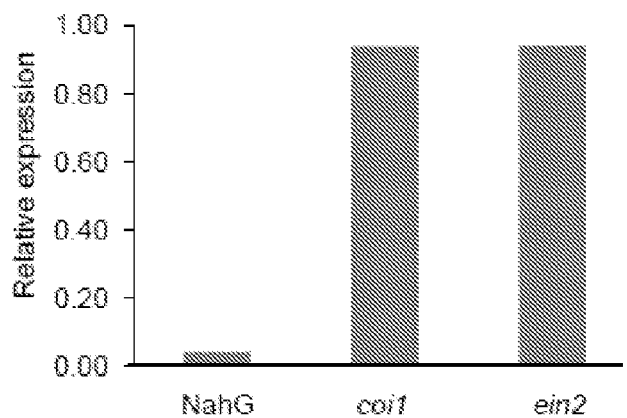
FIG. 11 is graph showing experimental results of S3H Expression in senescent leaves of WT, NahG, coi1 and ein2 mutants. S3H gene expression in senescent leaves of SA deficient line NahG, JA mutant coi1 and enthylene mutant ein2. The ratios of expression in senescing leaves of mutant and WT are shown. The data analyzed here were extracted from microarray data reported in a previous publication (Buchanan-Wollaston et al., "Comparative Transcriptome Analysis Reveals Significant Differences in Gene Expression and Signalling Pathways Between Developmental and Dark/Starvation-Induced Senescence in Arabidopsis," Plant J. 42(4):567-585 (2005), which is hereby incorporated by reference in its entirety).

The feedback regulation is supported by the facts that (i) S3H is readily induced by the treatment with SA (FIG. 1B and Table 2), and (ii) S3H is highly expressed in senescing leaves (FIG. 1A), which is most likely caused by the elevated levels of endogenous SA in senescing leaves (FIG. 4H; Bartsch et al., "Accumulation of Isochorismate-Derived 2,3-Dihydroxybenzoic 3-O-beta-D-Xyloside in *Arabidopsis* Resistance to Pathogens and Ageing of Leaves," *J. Biol. Chem.* 285(33):25654-25665 (2010) and Morris et al., "Salicylic Acid has a Role in Regulating Gene Expression During Leaf Senescence," *Plant J.* 23(5):677-685 (2000), each of which is hereby incorporated by reference in its entirety)). In senescing leaves of the SA-deficient NahG transgenic plants, the expression of S3H is almost undetectable but in the senescing leaves of the JA-deficient mutant coi1 and the ethylene-signaling mutant ein2 (as controls), S3H expression is not affected (FIG. 11) (Buchanan-Wollaston et al., "Comparative Transcriptome Analysis Reveals Significant Differences in Gene Expression and Signalling Pathways Between Developmental and Dark/Starvation-Induced Senescence in *Arabidopsis,*" *Plant J.* 42(4):567-585 (2005), which is hereby incorporated by reference in its entirety).

TABLE 2

S3H was induced by SA and pathogens[a]

| Stimulus | Concentration | Materials | Treat time | Induction folds |
|---|---|---|---|---|
| Salicylic acid | 10 μM | Col-0 (Seedling) | 3 hrs | 36.72 |
| Pst[b](DC3000) | 2 × 10⁵ cfu/ml | Ler (Adult leaf) | 12 hrs | 11.73 |
| Pst (DC3000) | 1 × 10⁵ cfu/ml | Col-0 (Adult leaf) | 48 hrs | 4.7 |
| Pst (DC3000, AvrRpt1) | 1 × 10⁸ cfu/ml | Col-0 (Adult leaf) | 6 hrs | 4.41 |
| Pst (DC3000, AvrRpt2) | 1 × 10⁵ cfu/ml | Col-0 (Adult leaf) | 48 hrs | 5.09 |
| Pst (DC3118) | 2 × 10⁷ cfu/ml | Col-5 (Adult leaf) | 10 hrs | 8.54 |
| H. arabidopsis | 5 × 10⁵ spores/ml | Col-0 (Adult leaf) | 4 days | 10.61 |
| H. arabidopsis | 5 × 10⁵ spores/ml | Col-0 (Seedling) | 6 days | 4.89 |
| Turnip mosaic virus | n.d[c]. | Col-0 (Adult leaf) | Zone[d] 0 | 26.24 |

[a]Data were collected from perturbation treatments in (genevestigator.com).
[b]Pst, *P.syringe* pv. Tomato.
[c]No description.
[d]Zone represents viral infection stage.

Figure 5:
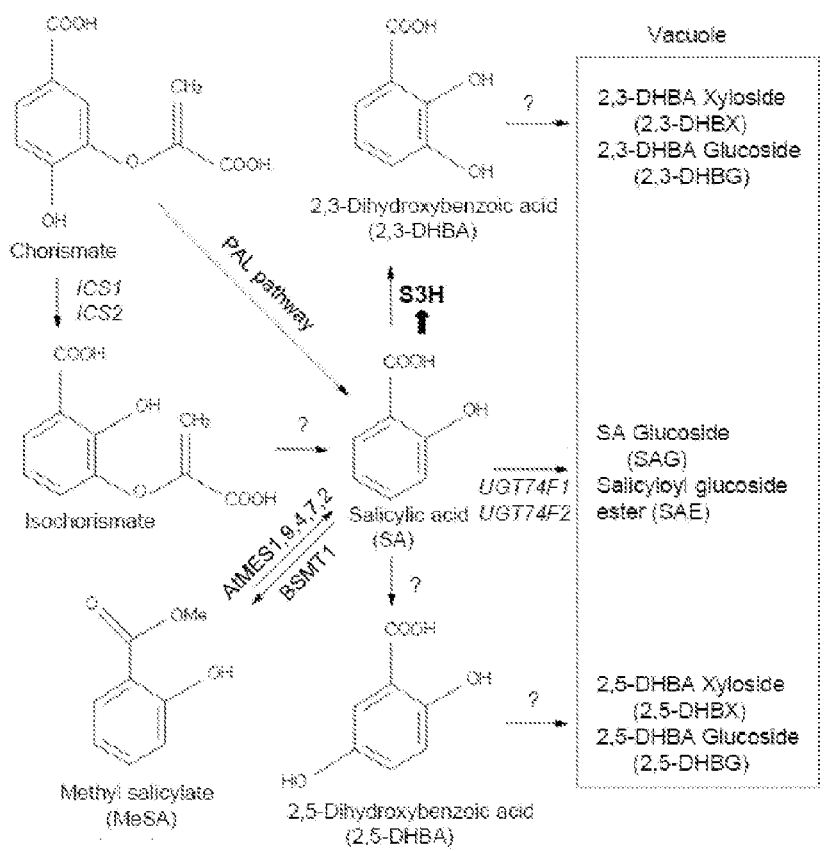
FIG. 5 is a schematic illustration of proposed SA metabolic pathways enriched with the newly discovered S3H in Arabidopsis. The SA 3-hydroxylase (S3H) indicated in bold reported here is induced by accumulating SA (indicated by a black arrow) and it catalyzes the SA to form 2,3-DHBA that will be subsequently conjugated by sugars by unknown enzymes to produce the storage form 2,3-DHBA sugar conjugates. The SA may also be converted to 2,5-DHBA (by an unknown enzyme) that is then converted to its sugar conjugates. In addition, SA can be catalyzed to produce its storage form salicylic sugar conjugates by enzyme UGT74F1 and UGT74F2. The methytransferase BSMT1 is responsible for the production of functional form methylsalicylic acid from SA while methyl easterase 1, 2, 4, 7, 9 are responsible for the reverse reaction from methylsalicylic acid to SA. Anabolically, two routes including isochorismate (IC) pathway and phenylalanine ammonia-lyase (PAL) pathway have been implicated in SA synthesis. In Arabidopsis the ICS pathway plays the main role while the PAL pathway plays a minor role, either directly or indirectly in the production of SA. The ICS1 and ICS2 are responsible for converting chorismate to isochorismate. The enzyme from isochorimate to SA is yet to be discovered.

The feedback regulation is further supported by the demonstration of S3H's enzymatic activity. Although the recombinant S3H possesses both 3-hydroxylase and 5-hydroxylase activities that convert SA to respective 2,3- and 2,5-DHBA in vitro (FIG. 4), S3H most likely acts as SA 3-hydroxylase in vivo because disruption of S3H renders 2,3-DHBA sugar conjugates undetectable whereas overexpression of S3H leads to a very high level accumulation of the 2,3-DHBA sugar conjugates (FIG. 4H). In contrast, the levels of 2,5-DHBA sugar conjugates increased in s3h and decreased in the overexpression lines, respectively (FIG. 4H), presumably resulting from changes in the SA metabolic flux in these mutants. For example, as shown in FIG. 5, because the conversion of SA to 2,3-DHBA is blocked in s3h, more SA becomes available for its conversion to 2,5-DHBA. It has been postulated that 2,3- and 2,5-DHBA species are products of SA oxidation by reactive oxygen species (ROS) (Bartsch et al., "Accumulation of Isochorismate-Derived 2,3-Dihydroxybenzoic 3-O-beta-D-Xyloside in *Arabidopsis* Resistance to Pathogens and Ageing of Leaves," *J. Biol. Chem.* 285(33):25654-25665 (2010), which is hereby incorporated by reference in its entirety). This research, however, provides direct evidence that 2,3-DHBA is enzymatically synthesized from SA, which enriches current understanding of SA metabolic pathways as shown in FIG. 5. Whether 2,5-DHBA is also enzymatically formed needs to be investigated.

The experimental results reported herein also provide strong molecular genetic evidence that S3H has a pivotal role in regulating the onset and rate of leaf senescence in *Arabidopsis* by modulating the endogenous levels of SA. S3H was initially identified during leaf senescence transcriptomic analyses (Guo et al., "Transcriptome of *Arabidopsis* Leaf Senescence," *Plant Cell Environ.* 27(5):521-549 (2004), each of which is hereby incorporated by reference in its entirety) as a senescence-associated gene whose transcript levels increase with the progression of leaf senescence (FIG. 1A). Leaf senescence was significantly accelerated in the T-DNA insertion s3h knockout plants but remarkably attenuated in the S3H overexpression lines (FIGS. 2 and 3A). Specifically, under the experimental growth conditions, a WT leaf started to senesce (as visible sign of yellowing at the leaf tip) at 19.2 DAE and took 9.5 days for the senescence to progress from the tip to the petiole. By comparison, a leaf of s3h or S3HOE began senescence 2.4 days earlier or 2 days later than that of WT, respectively. The rate of leaf senescence was also 72% faster in s3h and 54% slower in S3HOE than the rate of WT (FIG. 2G). Consistently, the expression of the leaf senescence marker genes SAG12 and SAG13 was also enhanced in s3h and inhibited in S3HOE (FIG. 3B).

S3H regulates leaf senescence most likely by controlling the SA levels. As discussed above, S3H modulates the SA levels in plants via a negative feedback regulatory mechanism. The SA levels in the senescing leaves were higher than those in the young leaves (FIG. 4H). Furthermore, the SA levels in s3h were much higher than in WT (FIG. 4H). In contrast, the SA levels in S3HOE were much lower (FIG. 4H). Previous correlative studies that revealed low SA levels in young leaves and high concentration in senescing leaves have suggested that SA promotes leaf senescence (Gan, in *Plant Hormones: Biosynthesis, Signal Transduction, Action!*, Ed. Davies (Springer, Dordrecht), pp 597-617 (2010), which is hereby incorporated by reference in its entirety). The suppression of SAG101, whose product interacts with PAD4 and EDS1 of SA signaling (Zhu et al., "SAG101 Forms a Ternary Complex With EDS1 and PAD4 and Is Required for Resistance Signaling Against Turnip Crinkle Virus," *PLoS Pathog.* 7(11):e1002318 (2011), which is hereby incorporated by reference in its entirety), displayed a delay in leaf senescence (He & Gan, "A Gene Encoding an Acyl Hydrolase Is Involved in Leaf Senescence in *Arabidopsis*," *Plant Cell* 14(4):805-815 (2002), which is hereby incorporated by reference in its entirety), also supporting a role of SA in leaf senescence. Overexpression of a bacterial gene named NahG reduced the SA levels and delayed leaf senescence, which further supports a role of SA in promoting leaf senescence (Morris et al., "Salicylic Acid has a Role in Regulating Gene Expression During Leaf Senescence," *Plant J.* 23(5):677-685 (2000), which is hereby incorporated by reference in its entirety). This research provides two lines of evidence for SA's role in leaf senescence. One line of evidence comes from S3HOE plants that, like NahG plants, have very low levels of SA (FIG. 4H) and display a significant delay in leaf senescence (FIGS. 2D and 3A). The other line of the evidence comes from s3h knockout plants that accumulate high levels of SA (FIG. 4H) and exhibit an early senescence phenotype (FIGS. 2A and 3A). It should be noted that although Nah G-overexpressing plants have been useful in many studies involving SA, the introduction of the bacterial gene may complicate interpretation of the data. For example, the NahG enzyme converts SA to catechol, which is quite different from the natural metabolites of SA in plants. Therefore, the S3HOE may be a better system for SA-related research in the future.

Figures 12A, 12B, 12C:
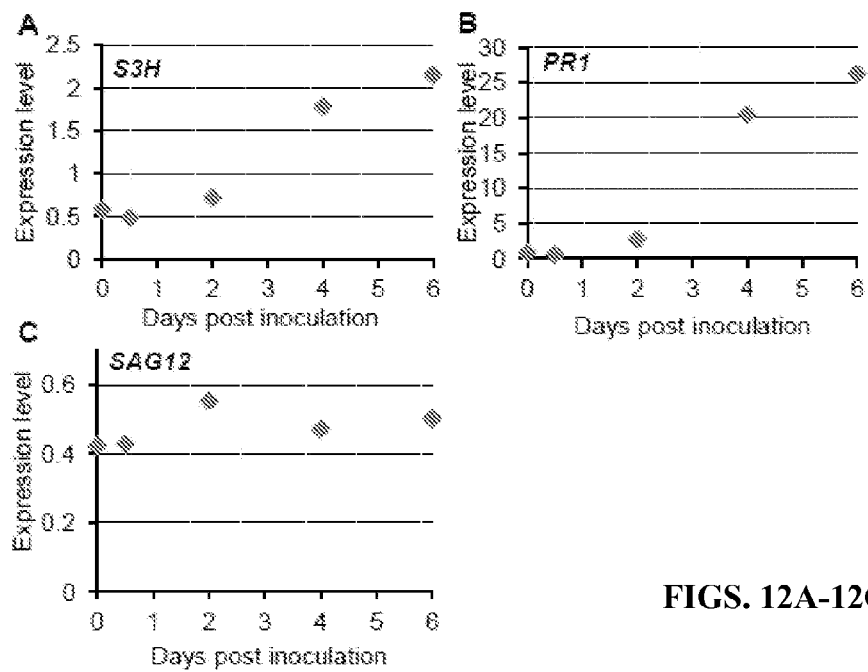
FIGS. 12A-12C show the time-course expression pattern of S3H (FIG. 12A), PR1 (FIG. 12B), SAG12 (FIG. 12C) after H. arabidopsis inoculation. The gene expression pattern of S3H is similar to pathogen induced marker gene PR1 after pathogen inoculation. The senescence specific expression marker gene SAG12 did not change during the inoculation, indicating the senescence was not significantly induced 6 days post inoculation. The data was extracted from microarray data reported in a previous publication (Wang et al., "Timing of Plant Immune Responses by a Central Circadian Regulator," Nature 470(7332):110-114 (2011), which is hereby incorporated by reference in its entirety).
Figure 13:
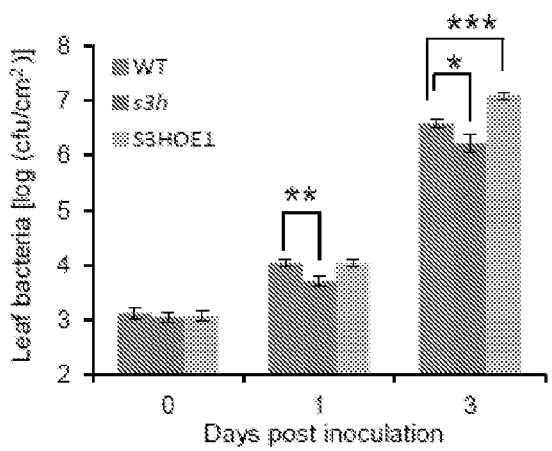
FIG. 13 is a graph showing results of an experiment demonstrating Resistant Phenotype of s3h mutant and Susceptible Phenotype S3HOE line Infected with P. syringae pv tomato DC3000. WT (left bars), s3h (center bars) and S3HOE1 (right bars) plants were infected with P. syringae DC3000, and the number of colony-forming units (cfu) per $cm^2$ leaf area was determined after 0, 1 and 3 days on agar plates. Leaf discs of 3 infected plants were pooled for this experiment. Error bars indicate SD of three biological repeats. *P<0.001P<0.01, *P<0.05.

In addition to leaf senescence, S3H appears to have a role in plant defense. Analyses of published (Wang et al., "Timing of Plant Immune Responses by a Central Circadian Regulator," Nature 470(7332):110-114 (2011), which is hereby incorporated by reference in its entirety) and other online microarray data (genevestigator.com) revealed that S3H can be induced by pathogen infection (FIGS. 12A-12C and Table 2). Consistently, the levels of 2,3-DHBA (the product of S3H-catalyzed reaction) derivatives were increased in Arabidopsis after challenging with pathogen (Bartsch et al., "Accumulation of Isochorismate-Derived 2,3-Dihydroxybenzoic 3-O-beta-D-Xyloside in Arabidopsis Resistance to Pathogens and Ageing of Leaves," J. Biol. Chem. 285(33):25654-25665 (2010), which is hereby incorporated by reference in its entirety). Knockout and overexpression of this gene resulted in enhanced and reduced resistance to Pseudomonas syringae pv. Tomato DC3000, respectively (FIG. 13).

Figure 8:
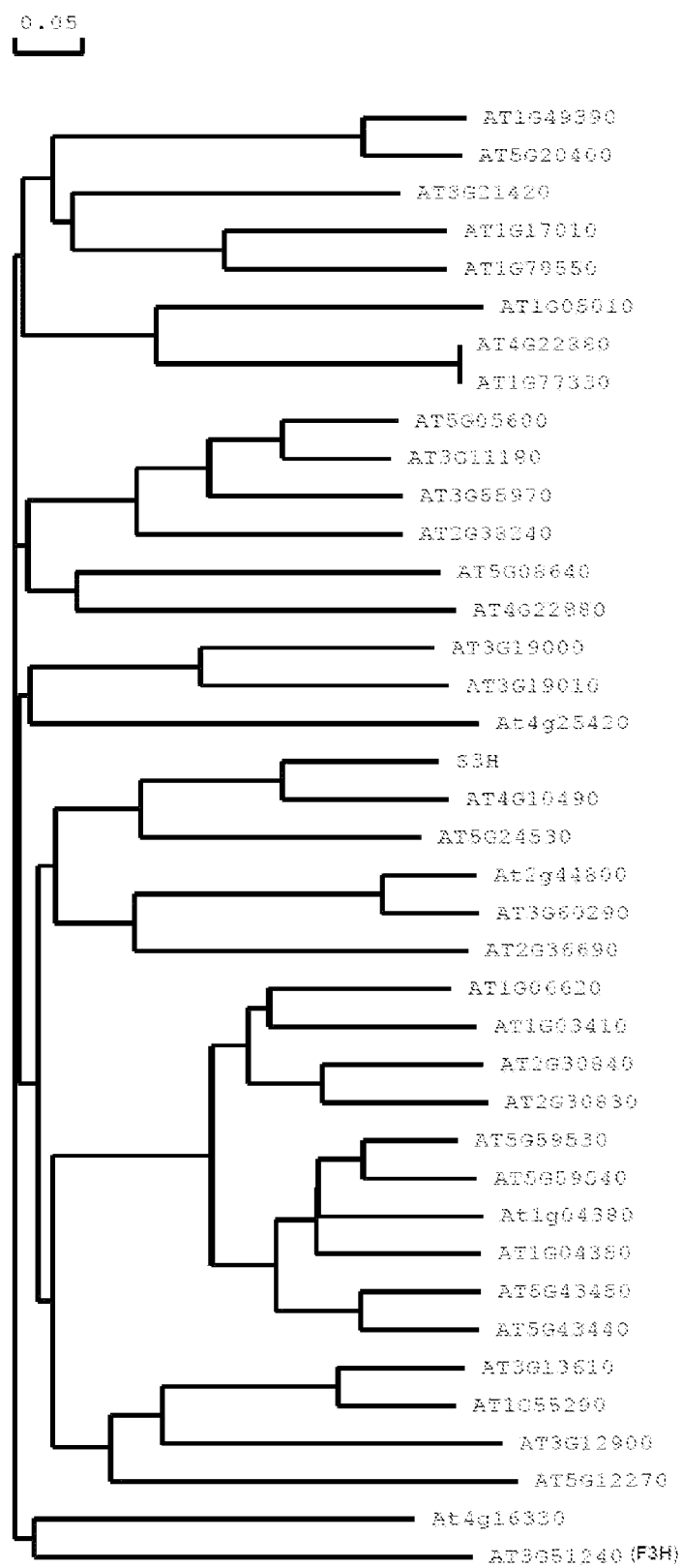
FIG. 8 is a phylogeny of S3H and its homologues in Arabidopsis genome. The deduced protein of S3H was used to search the protein sequence of its homologues and the phylogenetic tree was generated with DNAMAN software (version 7).
Figures 9, 10A, 10B:
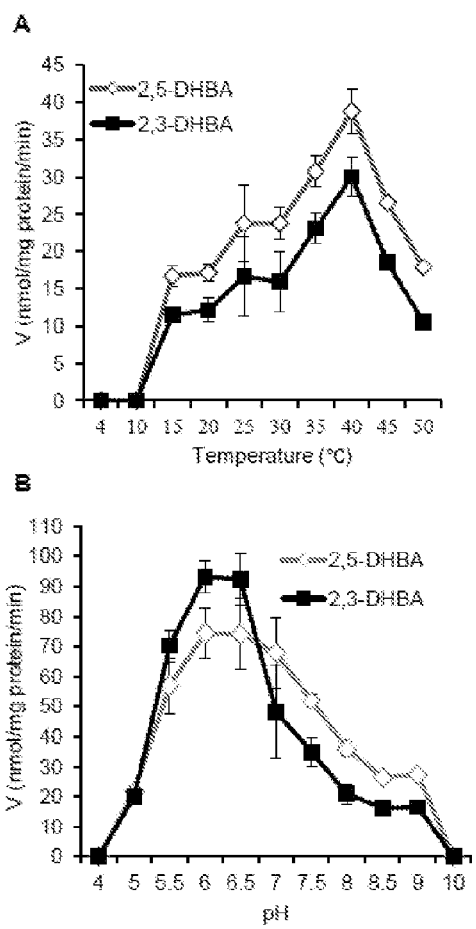
FIG. 9 is an amino acid alignment of deduced S3H protein (SEQ ID NO:3) and flavanone 3-hydroxylase enzyme (F3H) (SEQ ID NO:49). The alignment was done with DNAMAN software (version 7).
FIGS. 10A-10B show experimental results relating to effects of temperature (FIG. 10A) and pH value (FIG. 10B) on the S3H enzyme activities. The optimal temperature is around 40° C. and optimal pH value is 6.0. The data are the means and SE of three replicates.

In addition FIG. 8 is a phylogeny of S3H and its homologues in Arabidopsis genome. The deduced protein of S3H was used to search the protein sequence of its homologues and the phylogenetic tree was generated with DNAMAN software (version 7).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

```

What is claimed:

1. A transgenic plant having a reduced level of salicylic acid 3-hydroxylase ("S3H"), compared to that of a non-transgenic plant, wherein the transgenic plant displays a precocious or premature leaf senescence phenotype, relative to a non-transgenic plant, wherein the plant is transformed with a nucleic acid construct comprising a nucleic acid molecule configured to silence expression of an S3H protein having the amino acid sequence of SEQ ID NO: 3.

2. The plant according to claim 1, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, Arabidopsis thaliana, Saintpaulia, petunia, pelargonium, poinsettia, chrysanthemum, carnation, crocus, marigold, daffodil, pine, Medicago truncatula, Sandersonia aurantiaca, Populus trichocarpa, and zinnia.

3. Seed produced from the plant according to claim 1, wherein the seed comprises the nucleic acid construct.

4. A transgenic plant having an increased level of S3H, compared to that of a non-transgenic plant, wherein said transgenic plant displays a delayed leaf senescence phenotype, relative to a non-transgenic plant, wherein the plant is transformed with a nucleic acid construct that encodes an S3H protein having the amino acid sequence of SEQ ID NO: 3.

5. The plant according to claim 4, wherein the plant is selected from the group consisting of rice, corn, soybean, canola, potato, wheat, mung bean, alfalfa, barley, rye, cotton, sunflower, peanut, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, tobacco, tomato, sorghum, sugarcane, banana, Arabidopsis thaliana, Saintpaulia, petunia, pelargonium, poinsettia, chrysanthemum, carnation, crocus, marigold, daffodil, pine, Medicago truncatula, Sandersonia aurantiaca, Populus trichocarpa, and zinnia.

6. Seed produced from the plant according to claim 4, wherein the seed comprises the nucleic acid construct.

7. A mutant plant comprising an inactivated gene encoding an S3H protein having the amino acid sequence of SEQ ID NO:3, wherein the mutant plant displays a premature or precocious leaf senescence phenotype, relative to a non-mutant plant.

8. A method for promoting premature or precocious leaf senescence in a plant, said method comprising:

providing a transgenic plant or plant seed transformed with a nucleic acid construct effective in silencing expression of an S3H protein having the amino acid sequence of SEQ ID NO:3 and growing the transgenic plant or the plant grown from the transgenic plant seed under conditions effective to promote premature or precocious leaf senescence in the transgenic plant or the plant grown from the transgenic plant seed.

9. The method according to claim 8, wherein said nucleic acid construct comprises:

a nucleic acid molecule configured to silence the S3H protein expression;

a 5' DNA promoter sequence; and a 3' terminator sequence, wherein the nucleic acid molecule, the promoter, and the terminator are operatively coupled to permit expression of the nucleic acid molecule.

10. A method for delaying leaf senescence in a plant, said method comprising:

transforming a plant cell with a nucleic acid molecule encoding an S3H protein comprising the amino acid sequence of SEQ ID NO: 3, wherein the nucleic acid molecule is operably associated with a promoter to obtain a transformed plant cell, wherein expression of the nucleic acid molecule in the plant cell causes delayed leaf senescence; and regenerating a plant from the transformed plant cell under conditions effective to delay leaf senescence in the plant.

11. The method according to claim 10, wherein said transforming comprises transforming the plant cell with a nucleic acid construct comprising:
- the nucleic acid molecule;
- a 5' heterologous DNA promoter sequence; and
- a 3' terminator sequence, wherein the nucleic acid molecule, the DNA promoter sequence, and the terminator sequence are operatively coupled to permit transcription of the nucleic acid molecule.

12. A method of making a mutant plant having a decreased level of S3H protein compared to that of a non-mutant plant, wherein the mutant plant displays a premature or precocious leaf senescence phenotype relative to a non-mutant plant, said method comprising:
- providing at least one cell of a non-mutant plant containing a gene encoding a functional S3H protein comprising the amino acid sequence of SEQ ID NO:3;
- treating said at least one cell of a non-mutant plant under conditions effective to inactivate said gene, thereby yielding at least one mutant plant cell containing an inactivated S3H protein encoding gene; and
- propagating said at least one mutant plant cell into a mutant plant, wherein said mutant plant has a decreased level of S3H protein compared to that of the non-mutant plant and displays a premature or precocious leaf senescence phenotype relative to a non-mutant plant.

13. A method of inducing or promoting pathogen resistance in plants, said method comprising:
- providing a transgenic plant or plant seed transformed with a nucleic acid construct effective in silencing expression of an S3H protein comprising the amino acid sequence of SEQ ID NO:3; and
- growing the transgenic plant or the plant grown from the transgenic plant seed under conditions effective to induce or promote pathogen resistance in the transgenic plant or the plant grown from the transgenic plant seed.

* * * * *

                        SEQUENCE LISTING

<160> NUMBER OF SEQ ID NOS: 49

<210> SEQ ID NO 1
<211> LENGTH: 30
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 1

Asn Xaa Tyr Pro Xaa Cys Pro Xaa Pro Xaa Leu Xaa Xaa Gly Xaa Xaa
1               5                   10                  15

Xaa His Xaa Asp Xaa Xaa Xaa Xaa Thr Xaa Leu Leu Gln Asp
            20                  25                  30

<210> SEQ ID NO 2
<211> LENGTH: 1050
<212> TYPE: DNA
<213> ORGANISM: Arabidopsis thaliana
```

<400> SEQUENCE: 2

```
atggcaactt ctgcaatatc taagctctta gtgtctgatt tcgcctcctc cgttcacatc    60
ccttcaaact atgtccgacc aatctccgac cgtccgaact tgtccgaggt cgagagttct   120
ggcgattcca tccctctgat cgatctccgg gacctccatg gacctaatcg agccgtaatt   180
gtccaacaac ttgctagtgc cgtgttccact tatggtttct ttcagatcaa gaatcatgga   240
gtaccagata caaccgtcaa taaaatgcaa accgttgcga gagagttctt ccatcaaccc   300
gagagcgaaa gagtcaaaca ctactccgca gatccaacaa agacaacgag actctccacc   360
agtttcaacg tcggcgcaga caaagtcttg aactggagag acttccttag actccattgc   420
tttcccatag aagatttcat cgaagaatgg ccatctagtc ccatctcttt cagagaagtc   480
acagctgaat atgccacgag cgtaagagct ttggttttga cttcttga ggccatctca    540
gagagtttag gccttgaaag cgaccatata agcaatatat aggcaaaca cgctcaacac    600
atggcgttta actactatcc gccgtgtcca gaacccgagc taacttacgg acttcccgga   660
cataaagacc caaccgttat cactgtcctt cttcaagacc aagtctctgg tttgcaagtc   720
tttaaggatg ataaatgggt cgctgttagt ccaattccca cactttcat cgtcaatatc    780
ggcgaccaaa tgcaggtcat aagcaatgat aaatacaaga gtgtgctcca tagagccgta   840
gtaaacaccg agaacgagcg gttatcgatt ccgactttct atttcccttc aacagatgca   900
gtgattggtc cagcacacga gctggtcaat gaacaagact ctcttgccat ttacagaacc   960
tacccgtttg ttgagtattg ggacaagttt tggaacagat cacttgctac tgcgagctgt  1020
ctagacgcct tcaaagctcc aacaacctaa                                   1050
```

<210> SEQ ID NO 3
<211> LENGTH: 349
<212> TYPE: PRT
<213> ORGANISM: Arabidopsis thaliana

<400> SEQUENCE: 3

```
Met Ala Thr Ser Ala Ile Ser Lys Leu Leu Val Ser Asp Phe Ala Ser
1               5                   10                  15

Ser Val His Ile Pro Ser Asn Tyr Val Arg Pro Ile Ser Asp Arg Pro
            20                  25                  30

Asn Leu Ser Glu Val Glu Ser Ser Gly Asp Ser Ile Pro Leu Ile Asp
        35                  40                  45

Leu Arg Asp Leu His Gly Pro Asn Arg Ala Val Ile Val Gln Gln Leu
    50                  55                  60

Ala Ser Ala Cys Ser Thr Tyr Gly Phe Phe Gln Ile Lys Asn His Gly
65                  70                  75                  80

Val Pro Asp Thr Thr Val Asn Lys Met Gln Thr Val Ala Arg Glu Phe
                85                  90                  95

Phe His Gln Pro Glu Ser Glu Arg Val Lys His Tyr Ser Ala Asp Pro
            100                 105                 110

Thr Lys Thr Thr Arg Leu Ser Thr Ser Phe Asn Val Gly Ala Asp Lys
        115                 120                 125

Val Leu Asn Trp Arg Asp Phe Leu Arg Leu His Cys Phe Pro Ile Glu
    130                 135                 140

Asp Phe Ile Glu Glu Trp Pro Ser Ser Pro Ile Ser Phe Arg Glu Val
145                 150                 155                 160

Thr Ala Glu Tyr Ala Thr Ser Val Arg Ala Leu Val Leu Arg Leu Leu
                165                 170                 175
```

Glu Ala Ile Ser Glu Ser Leu Gly Leu Glu Ser Asp His Ile Ser Asn
                180                 185                 190

Ile Leu Gly Lys His Ala Gln His Met Ala Phe Asn Tyr Tyr Pro Pro
            195                 200                 205

Cys Pro Glu Pro Glu Leu Thr Tyr Gly Leu Pro Gly His Lys Asp Pro
    210                 215                 220

Thr Val Ile Thr Val Leu Leu Gln Asp Gln Val Ser Gly Leu Gln Val
225                 230                 235                 240

Phe Lys Asp Asp Lys Trp Val Ala Val Ser Pro Ile Pro Asn Thr Phe
                245                 250                 255

Ile Val Asn Ile Gly Asp Gln Met Gln Val Ile Ser Asn Asp Lys Tyr
            260                 265                 270

Lys Ser Val Leu His Arg Ala Val Val Asn Thr Glu Asn Glu Arg Leu
    275                 280                 285

Ser Ile Pro Thr Phe Tyr Phe Pro Ser Thr Asp Ala Val Ile Gly Pro
290                 295                 300

Ala His Glu Leu Val Asn Glu Gln Asp Ser Leu Ala Ile Tyr Arg Thr
305                 310                 315                 320

Tyr Pro Phe Val Glu Tyr Trp Asp Lys Phe Trp Asn Arg Ser Leu Ala
                325                 330                 335

Thr Ala Ser Cys Leu Asp Ala Phe Lys Ala Pro Thr Thr
                340                 345

<210> SEQ ID NO 4
<211> LENGTH: 1053
<212> TYPE: DNA
<213> ORGANISM: Populus trichocarpa

<400> SEQUENCE: 4

```
atggctccca ccgccaagct actactagcc gaccttgcat cttcaggtgt aaaacaaatt      60
ccttccaact tcatccgtcc catctccgac cgtccgaatc tctccgatgt tcagatttcg     120
gatggctcga ttcctctaat tgaccttcgt ggccttgatg gtcccaacca ctctactata     180
atcgaacaaa ttggccaagc atgccaaagg gatgggttct tcaggtgaa gaatcatggg      240
ataccagagg aaatgatcag tatcatacta acatagcta gacagttctt caaattgcct      300
gaaagtgaaa ggttaaaaaa ttactctgac gatcccacta agacaaccag ttgtctact      360
agtttcaata ttaagacaga acaagtttca agctggagag atttcttgag acttcattgt     420
tatcctctcg aagattacgt acatgaatgg cctagcaatc ctccatcatt caggaaagat     480
gtggctgaat attgcacaag tgttagaggt ctagtgttga gactgcttga ggccatatcc     540
gagagcttgg gtttggaaag agactatatt gataagaaat taggcgggca tggacaacat     600
atggctatga actactatcc accctgtcca cagccagaac tcacatatgg attgcctgga     660
cacaccgacc ctaatttaat caccatcctg ttacaagatc acgtgcctgg attgcaggtt     720
ctaagaaatg gcaagtggat tgctgtgaat ccgattccca atactttcat cgtcaacatc     780
ggtgatcaaa tgcaggtact tagcaatgat cgttacaaga gtgtgcttca ccgagcagtt     840
gtgaacagtg ataaagaccg aatatctata ccgacgttct actgtccttc accggatgct     900
gtaatcgggc ctccaaagga gctagtcgac gacgagcatc ctgccgtcta tagagatttt     960
acgtacggtg aatactatga gaagttttgg aacaagggac ttgtaaaaga atgttgcttg    1020
gacttgttca agccttctaa taatacaacc tag                                 1053
```

```
<210> SEQ ID NO 5
<211> LENGTH: 350
<212> TYPE: PRT
<213> ORGANISM: Populus trichocarpa

<400> SEQUENCE: 5
```

| | | | | | | | | | | | | | | | |
|---|---|---|---|---|---|---|---|---|---|---|---|---|---|---|---|
|Met|Ala|Pro|Thr|Ala|Lys|Leu|Leu|Ala|Asp|Leu|Ala|Ser|Ser|Gly| |
|1| | | |5| | | | |10| | | | |15| |
|Val|Lys|Gln|Ile|Pro|Ser|Asn|Phe|Ile|Arg|Pro|Ile|Ser|Asp|Arg|Pro|
| | | |20| | | | |25| | | | |30| | |
|Asn|Leu|Ser|Asp|Val|Gln|Ile|Ser|Asp|Gly|Ser|Ile|Pro|Leu|Ile|Asp|
| | | |35| | | | |40| | | | |45| | |
|Leu|Arg|Gly|Leu|Asp|Gly|Pro|Asn|His|Ser|Thr|Ile|Ile|Glu|Gln|Ile|
|50| | | | |55| | | | |60| | | | | |
|Gly|Gln|Ala|Cys|Gln|Arg|Asp|Gly|Phe|Phe|Gln|Val|Lys|Asn|His|Gly|
|65| | | | |70| | | | |75| | | | |80|
|Ile|Pro|Glu|Glu|Met|Ile|Ser|Ile|Ile|Leu|Asn|Ile|Ala|Arg|Gln|Phe|
| | | | |85| | | | |90| | | | |95| |
|Phe|Lys|Leu|Pro|Glu|Ser|Glu|Arg|Leu|Lys|Asn|Tyr|Ser|Asp|Asp|Pro|
| | | |100| | | | |105| | | | |110| | |
|Thr|Lys|Thr|Thr|Arg|Leu|Ser|Thr|Ser|Phe|Asn|Ile|Lys|Thr|Glu|Gln|
| | | |115| | | | |120| | | | |125| | |
|Val|Ser|Ser|Trp|Arg|Asp|Phe|Leu|Arg|Leu|His|Cys|Tyr|Pro|Leu|Glu|
|130| | | | |135| | | | |140| | | | | |
|Asp|Tyr|Val|His|Glu|Trp|Pro|Ser|Asn|Pro|Pro|Ser|Phe|Arg|Lys|Asp|
|145| | | | |150| | | | |155| | | | |160|
|Val|Ala|Glu|Tyr|Cys|Thr|Ser|Val|Arg|Gly|Leu|Val|Leu|Arg|Leu|Leu|
| | | | |165| | | | |170| | | | |175| |
|Glu|Ala|Ile|Ser|Glu|Ser|Leu|Gly|Leu|Glu|Arg|Asp|Tyr|Ile|Asp|Lys|
| | | |180| | | | |185| | | | |190| | |
|Lys|Leu|Gly|Gly|His|Gly|Gln|His|Met|Ala|Met|Asn|Tyr|Tyr|Pro|Pro|
| | | |195| | | | |200| | | | |205| | |
|Cys|Pro|Gln|Pro|Glu|Leu|Thr|Tyr|Gly|Leu|Pro|Gly|His|Thr|Asp|Pro|
|210| | | | |215| | | | |220| | | | | |
|Asn|Leu|Ile|Thr|Ile|Leu|Leu|Gln|Asp|His|Val|Pro|Gly|Leu|Gln|Val|
|225| | | | |230| | | | |235| | | | |240|
|Leu|Arg|Asn|Gly|Lys|Trp|Ile|Ala|Val|Asn|Pro|Ile|Pro|Asn|Thr|Phe|
| | | | |245| | | | |250| | | | |255| |
|Ile|Val|Asn|Ile|Gly|Asp|Gln|Met|Gln|Val|Leu|Ser|Asn|Asp|Arg|Tyr|
| | | |260| | | | |265| | | | |270| | |
|Lys|Ser|Val|Leu|His|Arg|Ala|Val|Asn|Ser|Asp|Lys|Asp|Arg|Ile|
| | | |275| | | | |280| | | | |285| | |
|Ser|Ile|Pro|Thr|Phe|Tyr|Cys|Pro|Ser|Pro|Asp|Ala|Val|Ile|Gly|Pro|
| | | |290| | | | |295| | | | |300| | |
|Pro|Lys|Glu|Leu|Val|Asp|Asp|Glu|His|Pro|Ala|Val|Tyr|Arg|Asp|Phe|
|305| | | | |310| | | | |315| | | | |320|
|Thr|Tyr|Gly|Glu|Tyr|Tyr|Glu|Lys|Phe|Trp|Asn|Lys|Gly|Leu|Val|Lys|
| | | | |325| | | | |330| | | | |335| |
|Glu|Cys|Cys|Leu|Asp|Leu|Phe|Lys|Pro|Ser|Asn|Asn|Thr|Thr| | |
| | | |340| | | | |345| | | | |350| | |

```
<210> SEQ ID NO 6
<211> LENGTH: 1056
<212> TYPE: DNA
<213> ORGANISM: Zea mays
```

<400> SEQUENCE: 6

```
atggccccag ccatttccaa gcctctcctt accgatctcg ttgcacagat cgggaaggtc    60
ccatcgagcc acatcaggcc tgtcggagac cgcccggacc tcgccaatgt cgacaacgag   120
tccggcgccg ggatcccgct catcgacctc aagaagctca acggcccgga gcgccgtaag   180
gtggtggagg ccatcggcaa ggcctgcgaa tccgacggct tcttcatggt gacgaaccac   240
ggcatcccgg cggcggtcgt ggagggcatg ctgcgcgtgg cgcgggagtt cttccacctg   300
ccggagtcgg agcggctcaa gtgctactcc gacgacccca caaggcgat ccggctgtcc   360
accagcttca acgtgcgcac ggagaaggtc agcaactggc gcgacttcct gcgcctgcat   420
tgctaccccc tccagagctt cgtcgaccag tggccgtcaa acccgccgtc cttcaggcaa   480
gtggtgggca cctacgcgac ggaggccagg gcgctggcgc tgaggctgct ggaggccata   540
tcggagagcc tgggcctgga gcggagccac atggtggcgg ccatggggag gcacgcgcag   600
cacatggcgg tgaactacta cccgccgtgc ccgcagccgg agctcaccta cgggctgccg   660
ggccacaagg accccaatgc catcacgctg ctgctgcagg acgcgtctc cggcctccag   720
gtgcagcgtg gcggccgctg ggtggccgtc aaccccgtgc caacgcgct ggtcatcaac   780
atcggagacc agatgcaggc actgagcaac gaccggtaca agagcgtgct ccaccgcgtg   840
atcgtcaaca gcgagagcga gcggatctcg gtgccgacgt tctactgccc gtccccggac   900
gcggtgatcg cgccggccga cgcgctggtg acgacggcc accctctggc ctaccgcccc   960
ttcacttacc aggagtacta cgacgcgttc tggaacatgg cctccagtc ggccagctgc  1020
ctcgaccggt ttaggcccgg aggatcgttg gagtga                           1056
```

<210> SEQ ID NO 7
<211> LENGTH: 351
<212> TYPE: PRT
<213> ORGANISM: Zea mays

<400> SEQUENCE: 7

```
Met Ala Pro Ala Ile Ser Lys Pro Leu Leu Thr Asp Leu Val Ala Gln
1               5                   10                  15

Ile Gly Lys Val Pro Ser Ser His Ile Arg Pro Val Gly Asp Arg Pro
            20                  25                  30

Asp Leu Ala Asn Val Asp Asn Glu Ser Gly Ala Gly Ile Pro Leu Ile
        35                  40                  45

Asp Leu Lys Lys Leu Asn Gly Pro Glu Arg Arg Lys Val Val Glu Ala
    50                  55                  60

Ile Gly Lys Ala Cys Glu Ser Asp Gly Phe Phe Met Val Thr Asn His
65                  70                  75                  80

Gly Ile Pro Ala Ala Val Val Glu Gly Met Leu Arg Val Ala Arg Glu
                85                  90                  95

Phe Phe His Leu Pro Glu Ser Glu Arg Leu Lys Cys Tyr Ser Asp Asp
            100                 105                 110

Pro Asn Lys Ala Ile Arg Leu Ser Thr Ser Phe Asn Val Arg Thr Glu
        115                 120                 125

Lys Val Ser Asn Trp Arg Asp Phe Leu Arg Leu His Cys Tyr Pro Leu
    130                 135                 140

Gln Ser Phe Val Asp Gln Trp Pro Ser Asn Pro Ser Phe Arg Gln
145                 150                 155                 160

Val Val Gly Thr Tyr Ala Thr Glu Ala Arg Ala Leu Ala Leu Arg Leu
                165                 170                 175
```

```
Leu Glu Ala Ile Ser Glu Ser Leu Gly Leu Glu Arg Ser His Met Val
            180                 185                 190
Ala Ala Met Gly Arg His Ala Gln His Met Ala Val Asn Tyr Tyr Pro
        195                 200                 205
Pro Cys Pro Gln Pro Glu Leu Thr Tyr Gly Leu Pro Gly His Lys Asp
    210                 215                 220
Pro Asn Ala Ile Thr Leu Leu Gln Asp Gly Val Ser Gly Leu Gln
225                 230                 235                 240
Val Gln Arg Gly Gly Arg Trp Val Ala Val Asn Pro Val Pro Asn Ala
                245                 250                 255
Leu Val Ile Asn Ile Gly Asp Gln Met Gln Ala Leu Ser Asn Asp Arg
            260                 265                 270
Tyr Lys Ser Val Leu His Arg Val Ile Val Asn Ser Glu Ser Glu Arg
        275                 280                 285
Ile Ser Val Pro Thr Phe Tyr Cys Pro Ser Pro Asp Ala Val Ile Ala
    290                 295                 300
Pro Ala Asp Ala Leu Val Asp Asp Gly His Pro Leu Ala Tyr Arg Pro
305                 310                 315                 320
Phe Thr Tyr Gln Glu Tyr Tyr Asp Ala Phe Trp Asn Met Gly Leu Gln
                325                 330                 335
Ser Ala Ser Cys Leu Asp Arg Phe Arg Pro Gly Gly Ser Leu Glu
            340                 345                 350

<210> SEQ ID NO 8
<211> LENGTH: 1056
<212> TYPE: DNA
<213> ORGANISM: Sorghum bicolor

<400> SEQUENCE: 8
atggccccag ccatttccaa gcctctcctc agcgatctcg tggcacagat cgggaaagtc      60
ccatcgagcc acatcaggcc tgtgggagac cgcccggacc tcgccaatgt cgacaacgag     120
tccggcgccg ggatcccgct catcgacctc aagatgctca acgggccgga gcgccgtaag     180
gtggtggagg ccatcggcag ggcctgcgaa tccgacggct tcttcatggt gacgaaccac     240
ggcatcccgg cggcggtggt ggaggggatg ctgcgcgtgg cgagggagtt cttccacctg     300
ccggagtcgg agcggctcaa gtgctactcc gacgacccca agaaggcgat ccggctgtcc     360
accagcttca acgtgcgcac ggagaaggtg aacaactggc gcgacttcct cgcgcctgcat     420
tgctacccgc tcgagagctt cgtcgaccag tggccgtcaa cccgccatc cttcaggcaa     480
gtggtgggca cctacgcgac ggaagcgagg gcgctagcgc tgaggctgct ggaggccata     540
tcggagagcc tgggcctgga gcggagccac atggtgcgcg ccatggggag cacgcgcag     600
cacatggcgg tgaactacta cccgccgtgc ccgcagccgg agctcaccta cgggctgccg     660
ggccacaagg accccaatgc catcacgctg ctgctccagg acggcgtctc cggcctgcag     720
gtgcagcgcg gcggccgatg gtggccgtg aaccccgtgc cgacgcgct ggtcatcaac     780
atcggagacc agatgcaggc actgagcaac gaccgataca gagcgtgct ccaccgcgtg     840
atcgtcaaca gcgagagcga gcggatctcg gtgccgacgt tttactgccc gtcgccggac     900
ggggtgatcg cgccggccga cgcgctggtg acgacgccc accctctggc ctaccgccct     960
ttcacttacc aggagtacta cgacgagttc tggaacatgg gcctccagtc ggcaagctgc    1020
ctcgaccggt ttaggcccgg aggatccata gagtga                              1056

<210> SEQ ID NO 9
```

```
<211> LENGTH: 350
<212> TYPE: PRT
<213> ORGANISM: Sorghum bicolor

<400> SEQUENCE: 9

Met Ala Pro Ala Ile Ser Lys Pro Leu Leu Ser Asp Leu Val Ala Gln
1               5                   10                  15

Ile Gly Lys Val Pro Ser Ser His Ile Arg Pro Val Gly Asp Arg Pro
            20                  25                  30

Asp Leu Ala Asn Val Asp Asn Glu Ser Gly Ala Gly Ile Pro Leu Ile
        35                  40                  45

Asp Leu Lys Met Leu Asn Gly Pro Glu Arg Arg Lys Val Val Glu Ala
    50                  55                  60

Ile Gly Arg Ala Cys Glu Ser Asp Gly Phe Phe Met Val Thr Asn His
65                  70                  75                  80

Gly Ile Pro Ala Ala Val Val Glu Gly Met Leu Arg Val Ala Arg Glu
                85                  90                  95

Phe Phe His Leu Pro Glu Ser Glu Arg Leu Lys Cys Tyr Ser Asp Asp
            100                 105                 110

Pro Lys Lys Ala Ile Arg Leu Ser Thr Ser Phe Asn Val Arg Thr Glu
        115                 120                 125

Lys Val Asn Asn Trp Arg Asp Phe Leu Arg Leu His Cys Tyr Pro Leu
    130                 135                 140

Glu Ser Phe Val Asp Gln Trp Pro Ser Asn Pro Ser Phe Arg Gln
145                 150                 155                 160

Val Val Gly Thr Tyr Ala Thr Glu Ala Arg Ala Leu Ala Leu Arg Leu
                165                 170                 175

Leu Glu Ala Ile Ser Glu Ser Leu Gly Leu Glu Arg Ser His Met Val
            180                 185                 190

Arg Ala Met Gly Arg His Ala Gln His Met Ala Val Asn Tyr Tyr Pro
        195                 200                 205

Pro Cys Pro Gln Pro Glu Leu Thr Tyr Gly Leu Pro Gly His Lys Asp
    210                 215                 220

Pro Asn Ala Ile Thr Leu Leu Leu Gln Asp Gly Val Ser Gly Leu Gln
225                 230                 235                 240

Val Gln Arg Gly Gly Arg Trp Val Ala Val Asn Pro Val Pro Asp Ala
                245                 250                 255

Leu Val Ile Asn Ile Gly Asp Gln Met Gln Ala Leu Ser Asn Asp Arg
            260                 265                 270

Tyr Lys Ser Val Leu His Arg Val Ile Val Asn Ser Glu Ser Glu Arg
        275                 280                 285

Ile Ser Val Pro Thr Phe Tyr Cys Pro Ser Asp Gly Val Ile Ala
    290                 295                 300

Pro Ala Asp Ala Leu Val Asp Asp Ala His Pro Leu Ala Tyr Arg Pro
305                 310                 315                 320

Phe Thr Tyr Gln Glu Tyr Asp Glu Phe Trp Asn Met Gly Leu Gln
                325                 330                 335

Ser Ala Ser Cys Leu Asp Arg Phe Arg Pro Gly Gly Ser Ile
            340                 345                 350

<210> SEQ ID NO 10
<211> LENGTH: 1059
<212> TYPE: DNA
<213> ORGANISM: Oryza sativa

<400> SEQUENCE: 10
```

```
atggctccag ccattgccaa gcctctcctg agcgatctgg tggcacaatc cgggcaagtc    60
ccctcgagcc acattcgtcc ggttggcgac cgcccggacc tcgacaacgt cgaccacgag   120
tccggcgccg gcattccggt catcgacctg aaacagctcg acggcccgga tcgccgcaag   180
gttgtcgagg ccatcggttc ggcgtgcgaa accgacggtt ttttcatggt gaagaatcac   240
gggatcccgg aggaggtggt ggaagggatg ctgcgcgtgg cgagggagtt cttccacatg   300
ccggagtcgg agcggctcaa gtgctattcc gacgacccca agaaggcgat ccggctgtcg   360
acgagcttca acgtgcgcac cgagaaggtg agcaactggc gcgacttcct gcgcttgcat   420
tgctaccctc tcgagagctt catcgaccag tggccctcca acccaccctc cttcaggcaa   480
gtggtcggca cctactcgag ggaggcgagg gcgctggcgc tgcggttgct ggaggcgata   540
tctgagagcc tcgggctgga gggggccac atggtgtcgg ccatggggcg gcaggcgcag   600
cacatggcgg tgaactacta tccgccatgc ccacagccgg agctcaccta cggcctgccg   660
ggcacaagg accccaatgc catcacgctg ctgctccagg acggcgtctc cggcctgcag   720
gtccagcgca acggccgctg ggtggccgtc aaccccgtgc ccgacgccct ggtcatcaac   780
atcggagatc aaatccaggc gctgagcaac gaccggtata gagcgtgct ccaccgggtg   840
atcgtgaaca gcgagagcga gaggatctcc gtgccgacgt tctactgccc gtccccggac   900
gcggtgatcg cgccggccgg cgcgctggtg gacggcgccc tgcacccgct ggcgtaccgg   960
cccttcaagt accaggccta ctacgacgaa ttctggaaca tgggcctcca gtccgccagc  1020
tgcttagacc ggttccggcc taacgatcag gccgtctga                         1059
```

<210> SEQ ID NO 11
<211> LENGTH: 352
<212> TYPE: PRT
<213> ORGANISM: Oryza sativa

<400> SEQUENCE: 11

```
Met Ala Pro Ala Ile Ala Lys Pro Leu Leu Ser Asp Leu Val Ala Gln
1               5                   10                  15

Ser Gly Gln Val Pro Ser Ser His Ile Arg Pro Val Gly Asp Arg Pro
            20                  25                  30

Asp Leu Asp Asn Val Asp His Glu Ser Gly Ala Gly Ile Pro Val Ile
        35                  40                  45

Asp Leu Lys Gln Leu Asp Gly Pro Asp Arg Arg Lys Val Val Glu Ala
    50                  55                  60

Ile Gly Ser Ala Cys Glu Thr Asp Gly Phe Phe Met Val Lys Asn His
65                  70                  75                  80

Gly Ile Pro Glu Glu Val Val Glu Gly Met Leu Arg Val Ala Arg Glu
                85                  90                  95

Phe Phe His Met Pro Glu Ser Glu Arg Leu Lys Cys Tyr Ser Asp Asp
            100                 105                 110

Pro Lys Lys Ala Ile Arg Leu Ser Thr Ser Phe Asn Val Arg Thr Glu
        115                 120                 125

Lys Val Ser Asn Trp Arg Asp Phe Leu Arg Leu His Cys Tyr Pro Leu
    130                 135                 140

Glu Ser Phe Ile Asp Gln Trp Pro Ser Asn Pro Pro Ser Phe Arg Gln
145                 150                 155                 160

Val Val Gly Thr Tyr Ser Arg Glu Ala Arg Ala Leu Ala Leu Arg Leu
                165                 170                 175

Leu Glu Ala Ile Ser Glu Ser Leu Gly Leu Glu Arg Gly His Met Val
```

```
                180                 185                 190
Ser Ala Met Gly Arg Gln Ala Gln His Met Ala Val Asn Tyr Tyr Pro
            195                 200                 205

Pro Cys Pro Gln Pro Glu Leu Thr Tyr Gly Leu Pro Gly His Lys Asp
            210                 215                 220

Pro Asn Ala Ile Thr Leu Leu Gln Asp Gly Val Ser Gly Leu Gln
225                 230                 235                 240

Val Gln Arg Asn Gly Arg Trp Val Ala Val Asn Pro Val Pro Asp Ala
                245                 250                 255

Leu Val Ile Asn Ile Gly Asp Gln Ile Gln Ala Leu Ser Asn Asp Arg
                260                 265                 270

Tyr Lys Ser Val Leu His Arg Val Ile Val Asn Ser Glu Ser Glu Arg
            275                 280                 285

Ile Ser Val Pro Thr Phe Tyr Cys Pro Ser Pro Asp Ala Val Ile Ala
            290                 295                 300

Pro Ala Gly Ala Leu Val Asp Gly Ala Leu His Pro Leu Ala Tyr Arg
305                 310                 315                 320

Pro Phe Lys Tyr Gln Ala Tyr Tyr Asp Glu Phe Trp Asn Met Gly Leu
                325                 330                 335

Gln Ser Ala Ser Cys Leu Asp Arg Phe Arg Pro Asn Asp Gln Ala Val
                340                 345                 350
```

<210> SEQ ID NO 12
<211> LENGTH: 1050
<212> TYPE: DNA
<213> ORGANISM: Hordeum vulgare

<400> SEQUENCE: 12

```
atggctccgg cgatcgccgc caagcctctc ctcagtgatc tggtggcaca aacccggcga    60
gttccgtcga gccacatcag agcggtcgga gaccgtccgg acctcgccaa tgtcgaccac   120
gagtccggcg cgggcattcc gctcatcgac ctgaagcacc tcgacgggcc agggcgtcgc   180
agggtcgtcg aggccatcgg ctcggcgtgc gagaacgacg ttttttcat ggtgacgaac   240
cacggcatcc ggaggcggt cgtggacggg atgctgcgcg tggcgaggga gttcttccac   300
ctgccggagt ctgaacggct caagtgctac tcagacgacc caagaaggc gatccggctg   360
tccacgagct tcaacgtgcg cacggagaag gtgagcaact ggcgcgattt cctccgcctg   420
cattgctacc ctctcgagag cttcatcgac cagtggccct caaacccgcc ggccttcagg   480
gaagcagtcg gcacctactc gacggaggcg agagcgctgg cgctcaggct gctggaggcg   540
atatcggaga gccttgggct cgagagaggc acatggtga aggccatggg gcggcacgcg   600
cagcacatgg cggtgaacta ctacccgccg tgcccgcagc cggagctgac gtacggactg   660
ccgggccaca aggaccccaa tgccgtcacg ctgctcctcc aggacggcgt gtccgggctt   720
caggtccggc gcgacggccg ctgggtcgcc gtcaacccg tgcccggcgc gttggtcatc   780
aacatcggcg atcaactgca ggctctgagc aacgaccgat acaagagcgt acttcaccgg   840
gtgattgtga acagcgagag cgagaggatc tcggtgccga cgttctactg cccgtccccg   900
gacgcggtgg tcgcgccggc ggaggcgctg gtggacggcg ccaccgtct ggcctatcgg   960
cccttcacct accaggagta ctacgaggag ttctggaaca tgggcctcga ggccgccagc  1020
tgcctcgacc gcttccgacc gatcgcgtga                                    1050
```

<210> SEQ ID NO 13
<211> LENGTH: 349

<212> TYPE: PRT
<213> ORGANISM: Hordeum vulgare

<400> SEQUENCE: 13

```
Met Ala Pro Ala Ile Ala Ala Lys Pro Leu Leu Ser Asp Leu Val Ala
1               5                   10                  15

Gln Thr Arg Arg Val Pro Ser Ser His Ile Arg Ala Val Gly Asp Arg
            20                  25                  30

Pro Asp Leu Ala Asn Val Asp His Glu Ser Gly Ala Gly Ile Pro Leu
        35                  40                  45

Ile Asp Leu Lys His Leu Asp Gly Pro Gly Arg Arg Arg Val Val Glu
    50                  55                  60

Ala Ile Gly Ser Ala Cys Glu Asn Asp Gly Phe Phe Met Val Thr Asn
65                  70                  75                  80

His Gly Ile Pro Glu Ala Val Val Asp Gly Met Leu Arg Val Ala Arg
                85                  90                  95

Glu Phe Phe His Leu Pro Glu Ser Glu Arg Leu Lys Cys Tyr Ser Asp
            100                 105                 110

Asp Pro Lys Lys Ala Ile Arg Leu Ser Thr Ser Phe Asn Val Arg Thr
        115                 120                 125

Glu Lys Val Ser Asn Trp Arg Asp Phe Leu Arg Leu His Cys Tyr Pro
    130                 135                 140

Leu Glu Ser Phe Ile Asp Gln Trp Pro Ser Asn Pro Pro Ala Phe Arg
145                 150                 155                 160

Glu Ala Val Gly Thr Tyr Ser Thr Glu Ala Arg Ala Leu Ala Leu Arg
                165                 170                 175

Leu Leu Glu Ala Ile Ser Glu Ser Leu Gly Leu Glu Arg Gly His Met
            180                 185                 190

Val Lys Ala Met Gly Arg His Ala Gln His Met Ala Val Asn Tyr Tyr
    195                 200                 205

Pro Pro Cys Pro Gln Pro Glu Leu Thr Tyr Gly Leu Pro Gly His Lys
210                 215                 220

Asp Pro Asn Ala Val Thr Leu Leu Leu Gln Asp Gly Val Ser Gly Leu
225                 230                 235                 240

Gln Val Arg Arg Asp Gly Arg Trp Val Ala Val Asn Pro Val Pro Gly
                245                 250                 255

Ala Leu Val Ile Asn Ile Gly Asp Gln Leu Gln Ala Leu Ser Asn Asp
            260                 265                 270

Arg Tyr Lys Ser Val Leu His Arg Val Ile Val Asn Ser Glu Ser Glu
    275                 280                 285

Arg Ile Ser Val Pro Thr Phe Tyr Cys Pro Ser Pro Asp Ala Val Val
290                 295                 300

Ala Pro Ala Glu Ala Leu Val Asp Gly Gly His Arg Leu Ala Tyr Arg
305                 310                 315                 320

Pro Phe Thr Tyr Gln Glu Tyr Tyr Glu Glu Phe Trp Asn Met Gly Leu
                325                 330                 335

Glu Ala Ala Ser Cys Leu Asp Arg Phe Arg Pro Ile Ala
            340                 345
```

<210> SEQ ID NO 14
<211> LENGTH: 1137
<212> TYPE: DNA
<213> ORGANISM: Triticum aestivum

<400> SEQUENCE: 14

```
atggcgccgg tgagcaacga gacgttcctc ccgacggcgg cctgggggga ggcgacgctg      60
cgcccgtcct tcgtgcggga cgaggacgag cggcccaagg tggcgcacga ccgcttcagc     120
gatgcggtgc cggtgatctc gctcgatggc atcgacggcg cgccgcgggc cgagatccgg     180
gaccgcgtgg cggcggcctg cgagggctgg ggcatcttcc aggtggtcga ccacggcgtc     240
gacgccgacc tcatcgccga catgacgcgc ctctctcgcg agttcttcgc gctgcccgcc     300
gaggacaagc tccggtacga catgtccggt ggcaagaagg gcggcttcat cgtctccagc     360
cacctgcagg gtgaggcggt gcaggactgg agggagattg tgacctactt ctcgtacccg     420
gtgaaagcac gggactacgg gcggtggccg gagaagccgg cggggtggcg cgcggtagtg     480
gagcggtaca gcgagcggct gatggagctg tcgtgcaagc tgctgggcgt gctctcggag     540
gcgatgggcc tggagacgga gtccctggcc aaggcgtgcg tggacatgga ccagaaggtg     600
gtggtcaact tctacccgcg cgtgtcccag cccgagctca ccctgggcgt caagcgccac     660
accgaccccg gcaccatcac cctcctcctc caggacctag tcggcggcct gcaggccacc     720
cgcgacggcg gcaagacctg gatcaccgtc cagcccatct ccggcgcctt cgtcgtcaac     780
ctcggcgacc acggccactt catgagcaac ggcaggttca gaacgcgga ccaccaggcg     840
gtggtgaacg gcagagcag ccggctgtcg atcgcgacgt tccagaaccc ggcgccggac     900
gcgagggtgt ggccgctggc ggtgagggag ggggaggagc ccatactgga ggagcccatc     960
accttctccg agatgtaccg ccgcaagatg gagcgcgacc tcgacctcgc caagcgcaag    1020
aagcaggcca aggaccagct gatgcagcag cagctccagc tccagcagca gcagcaggcg    1080
gtcgccgccg cgcccatgcc caccgccacc aagtctctca cgaaattct tgcctag       1137
```

<210> SEQ ID NO 15
<211> LENGTH: 378
<212> TYPE: PRT
<213> ORGANISM: Triticum aestivum

<400> SEQUENCE: 15

```
Met Ala Pro Val Ser Asn Glu Thr Phe Leu Pro Thr Ala Ala Trp Gly
1               5                   10                  15

Glu Ala Thr Leu Arg Pro Ser Phe Val Arg Asp Glu Asp Glu Arg Pro
            20                  25                  30

Lys Val Ala His Asp Arg Phe Ser Asp Ala Val Pro Val Ile Ser Leu
        35                  40                  45

Asp Gly Ile Asp Gly Ala Arg Arg Ala Glu Ile Arg Asp Arg Val Ala
    50                  55                  60

Ala Ala Cys Glu Gly Trp Gly Ile Phe Gln Val Val Asp His Gly Val
65                  70                  75                  80

Asp Ala Asp Leu Ile Ala Asp Met Thr Arg Leu Ser Arg Glu Phe Phe
                85                  90                  95

Ala Leu Pro Ala Glu Asp Lys Leu Arg Tyr Asp Met Ser Gly Gly Lys
            100                 105                 110

Lys Gly Gly Phe Ile Val Ser Ser His Leu Gln Gly Glu Ala Val Gln
        115                 120                 125

Asp Trp Arg Glu Ile Val Thr Tyr Phe Ser Tyr Pro Val Lys Ala Arg
    130                 135                 140

Asp Tyr Gly Arg Trp Pro Glu Lys Pro Ala Gly Trp Arg Ala Val Val
145                 150                 155                 160

Glu Arg Tyr Ser Glu Arg Leu Met Glu Leu Ser Cys Lys Leu Leu Gly
                165                 170                 175
```

```
Val Leu Ser Glu Ala Met Gly Leu Glu Thr Glu Ser Leu Ala Lys Ala
            180                 185                 190

Cys Val Asp Met Asp Gln Lys Val Val Asn Phe Tyr Pro Arg Cys
        195                 200                 205

Pro Gln Pro Glu Leu Thr Leu Gly Val Lys Arg His Thr Asp Pro Gly
    210                 215                 220

Thr Ile Thr Leu Leu Leu Gln Asp Leu Val Gly Gly Leu Gln Ala Thr
225                 230                 235                 240

Arg Asp Gly Gly Lys Thr Trp Ile Thr Val Gln Pro Ile Ser Gly Ala
                245                 250                 255

Phe Val Val Asn Leu Gly Asp His Gly His Phe Met Ser Asn Gly Arg
            260                 265                 270

Phe Lys Asn Ala Asp His Gln Ala Val Val Asn Gly Gln Ser Ser Arg
        275                 280                 285

Leu Ser Ile Ala Thr Phe Gln Asn Pro Ala Pro Asp Ala Arg Val Trp
    290                 295                 300

Pro Leu Ala Val Arg Glu Gly Glu Pro Ile Leu Glu Glu Pro Ile
305                 310                 315                 320

Thr Phe Ser Glu Met Tyr Arg Arg Lys Met Glu Arg Asp Leu Asp Leu
                325                 330                 335

Ala Lys Arg Lys Lys Gln Ala Lys Asp Gln Leu Met Gln Gln Leu
            340                 345                 350

Gln Leu Gln Gln Gln Gln Ala Val Ala Ala Pro Met Pro Thr
        355                 360                 365

Ala Thr Lys Ser Leu Asn Glu Ile Leu Ala
    370                 375

<210> SEQ ID NO 16
<211> LENGTH: 1110
<212> TYPE: DNA
<213> ORGANISM: Nicotiana tabacum

<400> SEQUENCE: 16
atggcacctt cgacattgac agctctagca gaggaaaaga cacttcaaac aagtttcata    60
agggatgaag atgagcgtcc aaaagtggct tataatcaat tcagtgacga gattccgatc   120
atatcgttga agggtattga tgatgagagt ggaattaatg gaaaaagagg tgaaatatgt   180
gaaaagattg ttaaggcatg tgaagattgg gcattttcc aggtagttga tcatggtgtt   240
gatgcccaac ttatctcaca aatgacaacc cttgctaaac aattcttcgc tttgcctcct   300
gaggaaaaac tacgctttga tatgtctggt ggcaagaaag tggcttcat tgtctctagc   360 catctacagg gtgaagtggt ccaagattgg cgtgaaatag tgacctattt ctcatatcca   420
attcgggcta gagactactc tagatggcca gacaaaccag atggatggat aggtgtgact   480
cagaagtaca gtgaaaagtt aatggagttg gcttgcaaat tattggaagt actatcagag   540
gcaatgggct tagagaagga ggccttaacc aaggcatgtg tggatatgga ccaaaaagtg   600
gttgtcaatt tttacccaaa gtgtccacag cccgacctta cccttggact gaaacgacac   660
actgatccag gaaccattac cctcttgtta caagaccaag ttggtgggct tcaagccact   720
aaagataatg gcaaaacttg gattactgtt cagcccgttg aaggcgcttt tgttgtcaat   780
cttggtgacc atggtcactt tttgagcaat ggaaggttta agaatgctga tcatcaagca   840
gtggtgaact cgaatagtag cagattatcg atagctacgt ttcagaatcc agcaccagaa   900
gctatagtgt acccattgaa aattagggaa ggagagaagg cagtaatgga cgagcccata   960
```

-continued

```
acatttgcag agatgtacag gaggaaaatg agcaaggacc ttgagcttgc taggctcaag    1020
aaactggcca aggaacacca aatacaagct gaaaaagctg ctgagaaggc caagttgaaa    1080
accaagccca ttgaagaaat tcttgcttaa                                     1110
```

<210> SEQ ID NO 17
<211> LENGTH: 369
<212> TYPE: PRT
<213> ORGANISM: Nicotiana tabacum

<400> SEQUENCE: 17

```
Met Ala Pro Ser Thr Leu Thr Ala Leu Ala Glu Glu Lys Thr Leu Gln
1               5                   10                  15

Thr Ser Phe Ile Arg Asp Glu Asp Glu Arg Pro Lys Val Ala Tyr Asn
            20                  25                  30

Gln Phe Ser Asp Glu Ile Pro Ile Ile Ser Leu Lys Gly Ile Asp Asp
        35                  40                  45

Glu Ser Gly Ile Asn Gly Lys Arg Gly Glu Ile Cys Glu Lys Ile Val
    50                  55                  60

Lys Ala Cys Glu Asp Trp Gly Ile Phe Gln Val Val Asp His Gly Val
65                  70                  75                  80

Asp Ala Gln Leu Ile Ser Gln Met Thr Thr Leu Ala Lys Gln Phe Phe
                85                  90                  95

Ala Leu Pro Pro Glu Glu Lys Leu Arg Phe Asp Met Ser Gly Gly Lys
            100                 105                 110

Lys Gly Gly Phe Ile Val Ser Ser His Leu Gln Gly Glu Val Val Gln
        115                 120                 125

Asp Trp Arg Glu Ile Val Thr Tyr Phe Ser Tyr Pro Ile Arg Ala Arg
    130                 135                 140

Asp Tyr Ser Arg Trp Pro Asp Lys Pro Asp Gly Trp Ile Gly Val Thr
145                 150                 155                 160

Gln Lys Tyr Ser Glu Lys Leu Met Glu Leu Ala Cys Lys Leu Leu Glu
                165                 170                 175

Val Leu Ser Glu Ala Met Gly Leu Glu Lys Glu Ala Leu Thr Lys Ala
            180                 185                 190

Cys Val Asp Met Asp Gln Lys Val Val Val Asn Phe Tyr Pro Lys Cys
        195                 200                 205

Pro Gln Pro Asp Leu Thr Leu Gly Leu Lys Arg His Thr Asp Pro Gly
    210                 215                 220

Thr Ile Thr Leu Leu Leu Gln Asp Gln Val Gly Gly Leu Gln Ala Thr
225                 230                 235                 240

Lys Asp Asn Gly Lys Thr Trp Ile Thr Val Gln Pro Val Glu Gly Ala
                245                 250                 255

Phe Val Val Asn Leu Gly Asp His Gly His Phe Leu Ser Asn Gly Arg
            260                 265                 270

Phe Lys Asn Ala Asp His Gln Ala Val Val Asn Ser Asn Ser Ser Arg
        275                 280                 285

Leu Ser Ile Ala Thr Phe Gln Asn Pro Ala Pro Glu Ala Ile Val Tyr
    290                 295                 300

Pro Leu Lys Ile Arg Glu Gly Glu Lys Ala Val Met Asp Glu Pro Ile
305                 310                 315                 320

Thr Phe Ala Glu Met Tyr Arg Arg Lys Met Ser Lys Asp Leu Glu Leu
                325                 330                 335

Ala Arg Leu Lys Lys Leu Ala Lys Glu His Gln Ile Gln Ala Glu Lys
            340                 345                 350
```

Ala Ala Glu Lys Ala Lys Leu Lys Thr Lys Pro Ile Glu Glu Ile Leu
        355                 360                 365

Ala

<210> SEQ ID NO 18
<211> LENGTH: 1047
<212> TYPE: DNA
<213> ORGANISM: Petunia spp.

<400> SEQUENCE: 18

```
atgaaaacag ctcaaggtgt cagtgcaacc ctaacaatgg aagtggcaag agtacaagca      60
atagcatcgt taagcaagtg catggacaca attccatcag agtacattag gtccgagaat     120
gagcaaccag cagccacaac cctgcatggg gtagttcttc aagtgccagt gattgaccta     180
cgtgaccctg atgagaacaa gatggtgaag ctcatagctg atgctagcaa agagtggggg     240
atattccaac tgatcaacca tggcattcct gatgaggcta tcgcggattt acagaaagta     300
gggaaagagt tctttgaaca tgttccacag gaggagaaag agctgattgc caagactcca     360
ggatcaaacg acattgaagg ctatggaact tctctgcaga aggaagtgga aggcaagaaa     420
ggttgggtgg atcatttgtt ccataagatt tggcctcctt ctgccgtcaa ctatcgttat     480
tggcctaaaa accctccttc atacagggaa gcaaacgaag aatatggaaa gaggatgcga     540
gaagttgtag acagaatttt taagagcttg tctcttgggc ttgggcttga aggccatgaa     600
atgatagagg cagctggtgg tgatgagata gtttacttgt tgaagatcaa ctattaccca     660
ccatgcccaa ggcccgattt ggctcttggt gttgtggccc atacggacat gtcatatatc     720
accattcttg tcccaaatga agtccaaggc ctccaagtgt tcaaggatgg ccattggtat     780
gatgtcaagt acataccaaa tgccttaatt gtccatattg gtgaccaagt tgagattctt     840
agcaatggca aatacaagag tgtataccat aggacaacgg tgaacaagga caagacaaga     900
atgtcatggc cggttttctt ggagcccccg tcagagcatg aagttgggcc aattcctaag     960
ctgcttagtg aggccaaccc acccaaattc aagaccaaga agtacaagga ttacgtctat    1020
tgtaagctta acaagcttcc tcagtga                                        1047
```

<210> SEQ ID NO 19
<211> LENGTH: 348
<212> TYPE: PRT
<213> ORGANISM: Petunia spp.

<400> SEQUENCE: 19

Met Lys Thr Ala Gln Gly Val Ser Ala Thr Leu Thr Met Glu Val Ala
1               5                   10                  15

Arg Val Gln Ala Ile Ala Ser Leu Ser Lys Cys Met Asp Thr Ile Pro
            20                  25                  30

Ser Glu Tyr Ile Arg Ser Glu Asn Glu Gln Pro Ala Ala Thr Thr Leu
        35                  40                  45

His Gly Val Val Leu Gln Val Pro Val Ile Asp Leu Arg Asp Pro Asp
    50                  55                  60

Glu Asn Lys Met Val Lys Leu Ile Ala Asp Ala Ser Lys Glu Trp Gly
65                  70                  75                  80

Ile Phe Gln Leu Ile Asn His Gly Ile Pro Asp Glu Ala Ile Ala Asp
                85                  90                  95

Leu Gln Lys Val Gly Lys Glu Phe Phe Glu His Val Pro Gln Glu Glu
            100                 105                 110

```
Lys Glu Leu Ile Ala Lys Thr Pro Gly Ser Asn Asp Ile Glu Gly Tyr
            115                 120                 125
Gly Thr Ser Leu Gln Lys Glu Val Glu Gly Lys Lys Gly Trp Val Asp
        130                 135                 140
His Leu Phe His Lys Ile Trp Pro Pro Ser Ala Val Asn Tyr Arg Tyr
145                 150                 155                 160
Trp Pro Lys Asn Pro Pro Ser Tyr Arg Glu Ala Asn Glu Glu Tyr Gly
                165                 170                 175
Lys Arg Met Arg Glu Val Val Asp Arg Ile Phe Lys Ser Leu Ser Leu
            180                 185                 190
Gly Leu Gly Leu Glu Gly His Glu Met Ile Glu Ala Ala Gly Gly Asp
        195                 200                 205
Glu Ile Val Tyr Leu Leu Lys Ile Asn Tyr Tyr Pro Pro Cys Pro Arg
    210                 215                 220
Pro Asp Leu Ala Leu Gly Val Ala His Thr Asp Met Ser Tyr Ile
225                 230                 235                 240
Thr Ile Leu Val Pro Asn Glu Val Gln Gly Leu Gln Val Phe Lys Asp
                245                 250                 255
Gly His Trp Tyr Asp Val Lys Tyr Ile Pro Asn Ala Leu Ile Val His
            260                 265                 270
Ile Gly Asp Gln Val Glu Ile Leu Ser Asn Gly Lys Tyr Lys Ser Val
        275                 280                 285
Tyr His Arg Thr Thr Val Asn Lys Asp Lys Thr Arg Met Ser Trp Pro
    290                 295                 300
Val Phe Leu Glu Pro Pro Ser Glu His Glu Val Gly Pro Ile Pro Lys
305                 310                 315                 320
Leu Leu Ser Glu Ala Asn Pro Pro Lys Phe Lys Thr Lys Lys Tyr Lys
                325                 330                 335
Asp Tyr Val Tyr Cys Lys Leu Asn Lys Leu Pro Gln
            340                 345

<210> SEQ ID NO 20
<211> LENGTH: 1038
<212> TYPE: DNA
<213> ORGANISM: Glycine max

<400> SEQUENCE: 20
atggccacca caaagccatt gttaaccgac ttagcctcca ccgttgatcg tgttccctct      60
aacttcatca ggcccattgg tgaccgtcca aaccttcagc aacttcactc ctccattgct     120
tctattccca tcatcgacct tcaaggcctt ggtggctcca tcattcccaa atcatccaa     180
aacattgcac atgcttgcca aaattatggc ttctttcaaa ttgtgaacca tgggattccg     240
gaggaggtgg tgagcaagat ggtgaatgtg tcaaaagagt tctttggttt gccggagagt     300
gagaggctga agaattactc tgatgaccca accaagacca caagactctc caccagtttc     360
aatgtcaaga ctgagaaagt ttccaactgg agagacttct tgagacttca ctgccacccc     420
cttgaggatt acattcaaga atggcctggc aaccctccat ctttcaggga gatgtggcg     480
gagtatagta gaaagatgag gggtttatca ctgaagttgc ttgaggcaat ctcagagagt     540
ttggggttgg aaaaggatta tagacaaag cattgggga acatgggca gcacatggcc     600
ataaactact accctccatg tcctgagcca gagttaacat atggtttgcc agctcatgct     660
gacccaaatg caattactat tctgctccaa aatcaagtcc ctggcttgca agtcctccat     720
gatggcaagt ggctaaccgt caatcctgtt cctaacacct tcattgtcaa tattgctgac     780
```

| | | | |
|---|---|---|---|
| caaattcagg tgataagcaa cgataggtac aagagtgtgc tgcatcgagc attggtgaat | 840 |
| tgtgagaagg agagaatgtc cattccaaca ttctattgcc cttcacctga tgcattgata | 900 |
| aaaccagcac cacaactcgt agacaaggaa catcctgcgc agtacacaaa cttcacatac | 960 |
| agagaatact acgacaagtt ctggatcaga ggactttcaa aagaaacatg cgtggacatg | 1020 |
| ttcaaggctc aagattaa | 1038 |

<210> SEQ ID NO 21
<211> LENGTH: 345
<212> TYPE: PRT
<213> ORGANISM: Glycine max

<400> SEQUENCE: 21

```
Met Ala Thr Thr Lys Pro Leu Leu Thr Asp Leu Ala Ser Thr Val Asp
1               5                   10                  15

Arg Val Pro Ser Asn Phe Ile Arg Pro Ile Gly Asp Arg Pro Asn Leu
            20                  25                  30

Gln Gln Leu His Ser Ser Ile Ala Ser Ile Pro Ile Ile Asp Leu Gln
        35                  40                  45

Gly Leu Gly Gly Ser Asn His Ser Gln Ile Ile Gln Asn Ile Ala His
    50                  55                  60

Ala Cys Gln Asn Tyr Gly Phe Phe Gln Ile Val Asn His Gly Ile Pro
65                  70                  75                  80

Glu Glu Val Val Ser Lys Met Val Asn Val Ser Lys Glu Phe Phe Gly
                85                  90                  95

Leu Pro Glu Ser Glu Arg Leu Lys Asn Tyr Ser Asp Asp Pro Thr Lys
            100                 105                 110

Thr Thr Arg Leu Ser Thr Ser Phe Asn Val Lys Thr Glu Lys Val Ser
        115                 120                 125

Asn Trp Arg Asp Phe Leu Arg Leu His Cys His Pro Leu Glu Asp Tyr
    130                 135                 140

Ile Gln Glu Trp Pro Gly Asn Pro Pro Ser Phe Arg Glu Asp Val Ala
145                 150                 155                 160

Glu Tyr Ser Arg Lys Met Arg Gly Leu Ser Leu Lys Leu Leu Glu Ala
                165                 170                 175

Ile Ser Glu Ser Leu Gly Leu Glu Lys Asp Tyr Ile Asp Lys Ala Leu
            180                 185                 190

Gly Lys His Gly Gln His Met Ala Ile Asn Tyr Tyr Pro Pro Cys Pro
        195                 200                 205

Glu Pro Glu Leu Thr Tyr Gly Leu Pro Ala His Ala Asp Pro Asn Ala
    210                 215                 220

Ile Thr Ile Leu Leu Gln Asn Gln Val Pro Gly Leu Gln Val Leu His
225                 230                 235                 240

Asp Gly Lys Trp Leu Thr Val Asn Pro Val Pro Asn Thr Phe Ile Val
                245                 250                 255

Asn Ile Ala Asp Gln Ile Gln Val Ile Ser Asn Asp Arg Tyr Lys Ser
            260                 265                 270

Val Leu His Arg Ala Leu Val Asn Cys Glu Lys Glu Arg Met Ser Ile
        275                 280                 285

Pro Thr Phe Tyr Cys Pro Ser Pro Asp Ala Leu Ile Lys Pro Ala Pro
    290                 295                 300

Gln Leu Val Asp Lys Glu His Pro Ala Gln Tyr Thr Asn Phe Thr Tyr
305                 310                 315                 320

Arg Glu Tyr Tyr Asp Lys Phe Trp Ile Arg Gly Leu Ser Lys Glu Thr
```

```
                    325                 330                 335
Cys Val Asp Met Phe Lys Ala Gln Asp
            340                 345

<210> SEQ ID NO 22
<211> LENGTH: 1107
<212> TYPE: DNA
<213> ORGANISM: Gossypium spp.

<400> SEQUENCE: 22
atggctcctt caactctgac ggctcttgcg gaagagaaaa ccttgcaggc aagcttcgtt     60
cgtgatgaag atgagcgtcc taaggttgct tacaaccaat tcagtaatga tatccctgtc    120
atctctcttg ctggtatcga tgatgttgat ggcaagaggg gtgagatatg caagaagatt    180
gttgaggctt gtgaggattg gggtgtcttc caggttgtgg atcatggtgt tgatactaaa    240
ctcgtgtccg aaatgacccg ttttgccaga gagttttttg ctttgcctgc tgaagagaag    300
cttcggttcg atatgtctgg tggcaagaaa ggtggtttca tcgtctccag ccaccttcag    360
ggagaagcag tgcaagattg cgggagattg tgacatact tttcatacc attgaagagc     420 agggactatt caaggtggcc tgataagcca gagggttgga ttgaagttac aaaggagtac    480
agcgagaagt tgatgggcct agcttgcaag cttcttgagg tgttgtcaga ggccatgggg    540
ttagagaagg aggctttgac taaggcatgt gtggacatgg atcagaaagt ggtggttaac    600
ttctatccta aatgccctca acctgacctc actttaggac tcaagcgcca cactgaccca    660
ggcaccatca cactcttgct tcaagaccaa gttggtgggc ttcaggccac ccgggacaat    720
ggcaagacgt ggatcactgt ccaacctgtg aaggagcct tgtggtcaa ccttggagac      780 catggccatt atctgagcaa tgggaggttc aagaatgctg atcaccaagc agtggtgaac    840
tcaaactgca gcagattgtc aatagccaca ttccaaaatc cagcacccga tgccacagtg    900
tatcccttga agatcagaga gggagagaaa ccaatccttg aggagcccat cacatttgct    960
gagatgtata ggaggaagat gagcaaggat cttgagcttg ccaggctgaa gaagctggcc   1020
aaagagcagc aacagttgaa ggagaaagag gctgagaatg agaagcccaa gcttgaagcc   1080
aagccattgg aggaaatcct tgcctaa                                       1107

<210> SEQ ID NO 23
<211> LENGTH: 368
<212> TYPE: PRT
<213> ORGANISM: Gossypium spp.

<400> SEQUENCE: 23

Met Ala Pro Ser Thr Leu Thr Ala Leu Ala Glu Glu Lys Thr Leu Gln
1               5                   10                  15

Ala Ser Phe Val Arg Asp Glu Asp Glu Arg Pro Lys Val Ala Tyr Asn
            20                  25                  30

Gln Phe Ser Asn Asp Ile Pro Val Ile Ser Leu Ala Gly Ile Asp Asp
        35                  40                  45

Val Asp Gly Lys Arg Gly Glu Ile Cys Lys Lys Ile Val Glu Ala Cys
    50                  55                  60

Glu Asp Trp Gly Val Phe Gln Val Val Asp His Gly Val Asp Thr Lys
65                  70                  75                  80

Leu Val Ser Glu Met Thr Arg Phe Ala Arg Glu Phe Phe Ala Leu Pro
                85                  90                  95

Ala Glu Glu Lys Leu Arg Phe Asp Met Ser Gly Gly Lys Lys Gly Gly
            100                 105                 110
```

```
Phe Ile Val Ser Ser His Leu Gln Gly Glu Ala Val Gln Asp Trp Arg
            115                 120                 125
Glu Ile Val Thr Tyr Phe Ser Tyr Pro Leu Lys Ser Arg Asp Tyr Ser
        130                 135                 140
Arg Trp Pro Asp Lys Pro Glu Gly Trp Ile Glu Val Thr Lys Glu Tyr
145                 150                 155                 160
Ser Glu Lys Leu Met Gly Leu Ala Cys Lys Leu Leu Glu Val Leu Ser
                165                 170                 175
Glu Ala Met Gly Leu Glu Lys Glu Ala Leu Thr Lys Ala Cys Val Asp
            180                 185                 190
Met Asp Gln Lys Val Val Asn Phe Tyr Pro Lys Cys Pro Gln Pro
            195                 200                 205
Asp Leu Thr Leu Gly Leu Lys Arg His Thr Asp Pro Gly Thr Ile Thr
        210                 215                 220
Leu Leu Leu Gln Asp Gln Val Gly Gly Leu Gln Ala Thr Arg Asp Asn
225                 230                 235                 240
Gly Lys Thr Trp Ile Thr Val Gln Pro Val Glu Gly Ala Phe Val Val
                245                 250                 255
Asn Leu Gly Asp His Gly His Tyr Leu Ser Asn Gly Arg Phe Lys Asn
            260                 265                 270
Ala Asp His Gln Ala Val Val Asn Ser Asn Cys Ser Arg Leu Ser Ile
        275                 280                 285
Ala Thr Phe Gln Asn Pro Ala Pro Asp Ala Thr Val Tyr Pro Leu Lys
        290                 295                 300
Ile Arg Glu Gly Glu Lys Pro Ile Leu Glu Glu Pro Ile Thr Phe Ala
305                 310                 315                 320
Glu Met Tyr Arg Arg Lys Met Ser Lys Asp Leu Glu Leu Ala Arg Leu
                325                 330                 335
Lys Lys Leu Ala Lys Glu Gln Gln Gln Leu Lys Glu Lys Glu Ala Glu
            340                 345                 350
Asn Glu Lys Pro Lys Leu Glu Ala Lys Pro Leu Glu Glu Ile Leu Ala
        355                 360                 365

<210> SEQ ID NO 24
<211> LENGTH: 1098
<212> TYPE: DNA
<213> ORGANISM: Malus domestica

<400> SEQUENCE: 24
atggctcctc ctgctactac gctgacatcc attgcgcatg agaaacccct acaacaaaaa      60
ttcgtccgag acgaagacga gcgtccaaag gttgcctaca acgaattcag caacgaaatt     120
ccgatcatct cgcttgccgg gatcgatgag gttgaaggcc gccgggccga gatttgcaag     180
aagattgtgg aagcttgtga ggactggggt attttccaga ttgttgatca tggagttgat     240
gccgagctca tatcggaaat gaccggtctc gccaaagagt tctttgattt gccatcggag     300
gagaagctcc gcttcgacat gtccggtggc aaaaagggtg gattcatcgt gtccagtcat     360
ttacagggag aagctgtgca agattggcgt gaaattgtga cctactttt atacccgatt     420 cgccaccggg actactcgag gtggccggac aagccagagg catggaggga ggtgacgaag     480
aagtacagcg acgagctgat ggggctggca tgcaagctct gggggtttt atcagaagcc     540 atggggttgg atacagaggc attgacaaag gcatgtgtgg acatggacca aaaagtggtg     600
gtgaatttct atccgaagtg ccctcagccc gacctaactc ttggcctcaa gcgccacacg     660
```

-continued

```
gacccgggca caattaccct tttgcttcag gaccaagttg gtggccttca ggctactagg       720
gatgatggga agacatggat caccgttcaa ccagtggaag gagcttttgt ggtcaatctc       780
ggagatcatg gtcattttct gagcaatggg aggttcaaga atgctgatca ccaagcagtg       840
gtgaactcaa acagcagcag gctgtccata gccacattcc agaacccagc tcaagatgca       900
atagtgtatc cactcagtgt gagggaggga gagaagccga ttctcgaggc gccgatcacc       960
tacaccgaga tgtacaagaa gaagatgagc aaagatcttg agcttgccag gctgaaaaag      1020
ctggccaagg aacagcaact gcaggacttg gagaaagcca agtggagaca aaagccagcg      1080
gacgacatat ttgcttag                                                    1098
```

<210> SEQ ID NO 25
<211> LENGTH: 365
<212> TYPE: PRT
<213> ORGANISM: Malus domestica

<400> SEQUENCE: 25

Met Ala Pro Pro Ala Thr Thr Leu Thr Ser Ile Ala His Glu Lys Thr
1               5                   10                  15

Leu Gln Gln Lys Phe Val Arg Asp Glu Asp Glu Arg Pro Lys Val Ala
            20                  25                  30

Tyr Asn Glu Phe Ser Asn Glu Ile Pro Ile Ile Ser Leu Ala Gly Ile
        35                  40                  45

Asp Glu Val Glu Gly Arg Arg Ala Glu Ile Cys Lys Lys Ile Val Glu
    50                  55                  60

Ala Cys Glu Asp Trp Gly Ile Phe Gln Ile Val Asp His Gly Val Asp
65                  70                  75                  80

Ala Glu Leu Ile Ser Glu Met Thr Gly Leu Ala Lys Glu Phe Phe Asp
                85                  90                  95

Leu Pro Ser Glu Glu Lys Leu Arg Phe Asp Met Ser Gly Gly Lys Lys
            100                 105                 110

Gly Gly Phe Ile Val Ser Ser His Leu Gln Gly Glu Ala Val Gln Asp
        115                 120                 125

Trp Arg Glu Ile Val Thr Tyr Phe Leu Tyr Pro Ile Arg His Arg Asp
    130                 135                 140

Tyr Ser Arg Trp Pro Asp Lys Pro Glu Ala Trp Arg Glu Val Thr Lys
145                 150                 155                 160

Lys Tyr Ser Asp Glu Leu Met Gly Leu Ala Cys Lys Leu Leu Gly Val
                165                 170                 175

Leu Ser Glu Ala Met Gly Leu Asp Thr Glu Ala Leu Thr Lys Ala Cys
            180                 185                 190

Val Asp Met Asp Gln Lys Val Val Asn Phe Tyr Pro Lys Cys Pro
        195                 200                 205

Gln Pro Asp Leu Thr Leu Gly Leu Lys Arg His Thr Asp Pro Gly Thr
    210                 215                 220

Ile Thr Leu Leu Leu Gln Asp Gln Val Gly Gly Leu Gln Ala Thr Arg
225                 230                 235                 240

Asp Asp Gly Lys Thr Trp Ile Thr Val Gln Pro Val Glu Gly Ala Phe
                245                 250                 255

Val Val Asn Leu Gly Asp His Gly His Phe Leu Ser Asn Gly Arg Phe
            260                 265                 270

Lys Asn Ala Asp His Gln Ala Val Val Asn Ser Asn Ser Ser Arg Leu
        275                 280                 285

Ser Ile Ala Thr Phe Gln Asn Pro Ala Gln Asp Ala Ile Val Tyr Pro

```
                290               295               300
Leu Ser Val Arg Glu Gly Glu Lys Pro Ile Leu Glu Ala Pro Ile Thr
305                 310               315               320

Tyr Thr Glu Met Tyr Lys Lys Met Ser Lys Asp Leu Glu Leu Ala
              325               330               335

Arg Leu Lys Lys Leu Ala Lys Glu Gln Leu Gln Asp Leu Glu Lys
          340               345               350

Ala Lys Val Glu Thr Lys Pro Ala Asp Asp Ile Phe Ala
        355               360               365

<210> SEQ ID NO 26
<211> LENGTH: 1077
<212> TYPE: DNA
<213> ORGANISM: Brassica napus

<400> SEQUENCE: 26
atggctccag gaactctaaa tgagcttgcc ggagagacta agctcaactc caagtttgtc      60
cgggacgagg acgaacgtcc caaggttgcc tacaatgagt ttagcacgga gatccccgtg     120
atctctctcg ccggaatcga cgatgttggt gagaaaagag agagatctg tcgacagatc     180
gttgaggctt gtgagaactg gggtgttttt caggtggtcg atcatggagt ggatactagt     240
ttggtggccg atatgactcg tctcgctcga gacttcttcg cgttacctcc tgaggagaaa     300
ctcaagttcg acatgtctgg tggtaaaaag ggaggattca ttgtctctag tcatcttcag     360
ggagagtctg ttcaagattg agagagatc gtgacgtatt ctcgtaccc ggtgagaaac       420
agagactact cacggtggcc gactaagccg aaggatgggt gaaagtgac ggaggagtac      480
agcgagaggc tgatgggttt ggcttgtaaa cttcttgagg ttttgtctga agctatgggg     540
ctcgagaaag aggcactcac caatgcatgc gtcgatatgg accagaaaat agttgttaac     600
tattacccaa aatgccctca gcctgatcta accctcgggc tcaagcgtca cactgaccct     660
ggaaccatca ctttgctgct ccaagaccaa gttggtggtt acaagccac acgagacgat     720
gggaagacat ggattacagt tcagcctgtt gaaggagctt tgttgttaa tcttggcgac     780
catggtcact atctgagcaa cgggaggttc aagaacgctg accaccaggc ggtggtgaac     840
tccaactcga gcagactatc aatagccacg ttccagaatc cggcgccgga agcaaccgtg     900
tatccgctta agtgagagaa ggagagaaag ccgatcttgg aggagccaat tacgtttgcg     960
gagatgtata agagaaagat gagtagagat ctcgagctgg ctcgcctcaa gaagctggcg    1020
aaagaagagc atgaccacaa ggaagctgcc aagcctctag accaaatcat cgcttag       1077

<210> SEQ ID NO 27
<211> LENGTH: 358
<212> TYPE: PRT
<213> ORGANISM: Brassica napus

<400> SEQUENCE: 27

Met Ala Pro Gly Thr Leu Asn Glu Leu Ala Gly Glu Thr Lys Leu Asn
1                5                  10                  15

Ser Lys Phe Val Arg Asp Glu Asp Arg Pro Lys Val Ala Tyr Asn
              20                  25                  30

Glu Phe Ser Thr Glu Ile Pro Val Ile Ser Leu Ala Gly Ile Asp Asp
            35                  40                  45

Val Gly Glu Lys Arg Gly Glu Ile Cys Arg Gln Ile Val Glu Ala Cys
        50                  55                  60

Glu Asn Trp Gly Val Phe Gln Val Val Asp His Gly Val Asp Thr Ser
```

```
                65                  70                  75                  80
Leu Val Ala Asp Met Thr Arg Leu Ala Arg Asp Phe Phe Ala Leu Pro
                        85                  90                  95
Pro Glu Glu Lys Leu Lys Phe Asp Met Ser Gly Gly Lys Gly Gly
                100                 105                 110
Phe Ile Val Ser Ser His Leu Gln Gly Glu Ser Val Gln Asp Trp Arg
                115                 120                 125
Glu Ile Val Thr Tyr Phe Ser Tyr Pro Val Arg Asn Arg Asp Tyr Ser
            130                 135                 140
Arg Trp Pro Thr Lys Pro Glu Gly Trp Val Lys Val Thr Glu Glu Tyr
145                 150                 155                 160
Ser Glu Arg Leu Met Gly Leu Ala Cys Lys Leu Leu Glu Val Leu Ser
                165                 170                 175
Glu Ala Met Gly Leu Glu Lys Glu Ala Leu Thr Asn Ala Cys Val Asp
                180                 185                 190
Met Asp Gln Lys Ile Val Val Asn Tyr Tyr Pro Lys Cys Pro Gln Pro
                195                 200                 205
Asp Leu Thr Leu Gly Leu Lys Arg His Thr Asp Pro Gly Thr Ile Thr
            210                 215                 220
Leu Leu Leu Gln Asp Gln Val Gly Gly Leu Gln Ala Thr Arg Asp Asp
225                 230                 235                 240
Gly Lys Thr Trp Ile Thr Val Gln Pro Val Glu Gly Ala Phe Val Val
                245                 250                 255
Asn Leu Gly Asp His Gly His Tyr Leu Ser Asn Gly Arg Phe Lys Asn
                260                 265                 270
Ala Asp His Gln Ala Val Val Asn Ser Asn Ser Ser Arg Leu Ser Ile
                275                 280                 285
Ala Thr Phe Gln Asn Pro Ala Pro Glu Ala Thr Val Tyr Pro Leu Lys
                290                 295                 300
Val Arg Glu Gly Glu Lys Pro Ile Leu Glu Glu Pro Ile Thr Phe Ala
305                 310                 315                 320
Glu Met Tyr Lys Arg Lys Met Ser Arg Asp Leu Glu Leu Ala Arg Leu
                325                 330                 335
Lys Lys Leu Ala Lys Glu Glu His Asp His Lys Glu Ala Ala Lys Pro
                340                 345                 350
Leu Asp Gln Ile Ile Ala
            355

<210> SEQ ID NO 28
<211> LENGTH: 1077
<212> TYPE: DNA
<213> ORGANISM: Solanum tuberosum

<400> SEQUENCE: 28
atggcttcaa cactaacagc tctagctaat gaaaagaccc ttcaaacaag ttttattagg      60
gatgaagaag aacgtccaaa agtggcttac aataaattta gtgacgaaat tccagtaata     120
tcgttgcaag gtattgatga tattaatgga agaagaagtg aaatatgtga gaaaattgta     180
aatgcttgtg aagattgggg agtttttcag gtaattgatc atggggccga tgctcaatta     240
atatcagaaa tgacaaaatt ggctaaggaa ttttttcgaat tgcctcctga cgaaaagctt     300
cggtttgaca tgtctggtgg caagaaaggc ggctttattg tctcaagcca tttacagggt     360
gaagtggttc aagactggcg tgaaatagtg acctactttt cttacccaat tcgagctaga     420
gactactcca gatggccaga caaaccacaa ggctggatag ctgtaactga gaaatacagt     480
```

-continued

```
gaaaaattaa tggacttggc ttgcaaatta ttagaagtat tatcagaggc aatgggctta      540
gagaaagagg ctttaaccaa ggcatgtgtg gatatggacc aaaaagtagt tgtcaatttt      600
tacccaaagt gtccagagcc tgaccttacc cttgggctga acgacatac tgatccagga       660 accatcaccc tcttgttaca agaccaagtt ggtgggcttc aagccactaa agataatggc      720
aaaacttgga tcactgttca gcccgttgaa ggcgcttttg ttgttaatct tggtgatcat      780
ggtcattatt tgagcaatgg gaggttcaag aatgctgatc atcaagcagt tgtgaattcg      840
aatagcagca gattatcgat agccactttt cagaatccag caccggatgc aaaagtgtat      900
ccgttaaaaa ttagggaagg agagaaggca ataatggatg agccgattac atttgcagaa      960
atgtacagga ggaaaatgag taaggatctt gagcttgcta ggctcaagaa actggccaag     1020
gaacagactg aagaggccaa gttggagtcc aagcccattg aggaaattct tgcttaa       1077
```

<210> SEQ ID NO 29
<211> LENGTH: 358
<212> TYPE: PRT
<213> ORGANISM: Solanum tuberosum

<400> SEQUENCE: 29

```
Met Ala Ser Thr Leu Thr Ala Leu Ala Asn Glu Lys Thr Leu Gln Thr
1               5                   10                  15

Ser Phe Ile Arg Asp Glu Glu Arg Pro Lys Val Ala Tyr Asn Lys
            20                  25                  30

Phe Ser Asp Glu Ile Pro Val Ile Ser Leu Gln Gly Ile Asp Asp Ile
        35                  40                  45

Asn Gly Arg Arg Ser Glu Ile Cys Glu Lys Ile Val Asn Ala Cys Glu
    50                  55                  60

Asp Trp Gly Val Phe Gln Val Ile Asp His Gly Ala Asp Ala Gln Leu
65                  70                  75                  80

Ile Ser Glu Met Thr Lys Leu Ala Lys Glu Phe Phe Glu Leu Pro Pro
                85                  90                  95

Asp Glu Lys Leu Arg Phe Asp Met Ser Gly Gly Lys Lys Gly Gly Phe
            100                 105                 110

Ile Val Ser Ser His Leu Gln Gly Glu Val Val Gln Asp Trp Arg Glu
        115                 120                 125

Ile Val Thr Tyr Phe Ser Tyr Pro Ile Arg Ala Arg Asp Tyr Ser Arg
    130                 135                 140

Trp Pro Asp Lys Pro Gln Gly Trp Ile Ala Val Thr Glu Lys Tyr Ser
145                 150                 155                 160

Glu Lys Leu Met Asp Leu Ala Cys Lys Leu Leu Glu Val Leu Ser Glu
                165                 170                 175

Ala Met Gly Leu Glu Lys Glu Ala Leu Thr Lys Ala Cys Val Asp Met
            180                 185                 190

Asp Gln Lys Val Val Asn Phe Tyr Pro Lys Cys Pro Glu Pro Asp
        195                 200                 205

Leu Thr Leu Gly Leu Lys Arg His Thr Asp Pro Gly Thr Ile Thr Leu
    210                 215                 220

Leu Leu Gln Asp Gln Val Gly Leu Gln Ala Thr Lys Asp Asn Gly
225                 230                 235                 240

Lys Thr Trp Ile Thr Val Gln Pro Val Glu Gly Ala Phe Val Val Asn
                245                 250                 255

Leu Gly Asp His Gly His Tyr Leu Ser Asn Gly Arg Phe Lys Asn Ala
            260                 265                 270
```

```
Asp His Gln Ala Val Val Asn Ser Asn Ser Ser Arg Leu Ser Ile Ala
        275                 280                 285

Thr Phe Gln Asn Pro Ala Pro Asp Ala Lys Val Tyr Pro Leu Lys Ile
        290                 295                 300

Arg Glu Gly Glu Lys Ala Ile Met Asp Glu Pro Ile Thr Phe Ala Glu
305                 310                 315                 320

Met Tyr Arg Arg Lys Met Ser Lys Asp Leu Glu Leu Ala Arg Leu Lys
                325                 330                 335

Lys Leu Ala Lys Glu Gln Thr Glu Glu Ala Lys Leu Glu Ser Lys Pro
            340                 345                 350

Ile Glu Glu Ile Leu Ala
            355

<210> SEQ ID NO 30
<211> LENGTH: 1029
<212> TYPE: DNA
<213> ORGANISM: Solanum lycopersicum

<400> SEQUENCE: 30
atgacaacaa caagtgttct ttctagtgga ttcaaccact caaccctccc tcagtcttac        60
gttcgacctg aatctcaaag accttgcatg tctgaagttg ttgatagcga cgatcttgtc       120
ccagtcattg atatgtcttg tactaatagg aacgttatcg ttcatcaaat cggtgaagct       180
tgtcgtcttt atgggttttt ccaggtgata aatcacggtg tgtcgaagaa ggtgatagat       240
gaaatgttag gggtaagtca tgaatttttt aagctaccag ttgaagaaaa gatgaaattg       300
tattctgatg atccatcaaa aactatgaga ttatcaacta gttttaatgt taagaaggaa       360
gctgttcata attggagaga ttatcttagg ctacattgtt atcctttgga caaatatgcc       420
cctgaatggc cttctaatcc tccttctttc agggaaatag taagcaaata ttgcatggaa       480
gttagagagc ttggatatag attggaagaa gcaatatcag agagcttagg gcttgagaag       540
gattgtataa aaaatgtgtt aggtgaacaa ggacaacata tggctatcaa tttttatcct       600
cagtgtccac aacctgaatt aacttatggg ttaccagccc atacagatcc aaatgcaatt       660
acaattcttc ttcaagattt gcaagtggct ggccttcaag ttcttaagga tggaaaatgg       720
ctatctatta aacctcagcc taatgccttt gtcatcaatc ttggtgatca attggaggcg       780
ttgagtaatg ggaagtataa aagtatatgg catagagcta tagtgaattc agacaaagca       840
aggatgtctg tggcttcttt cctctgtccc aatgattgtt ccattatcag tgctccaaaa       900
accttaactg aagatggatc ttctgcaatt tatcgacatt tcacttatgc tgaatattat       960
gaaaaattct ggagcaggaa tttagatcag gaatattgtt tagaactttt caagaacgat      1020
ggaacctag                                                             1029

<210> SEQ ID NO 31
<211> LENGTH: 342
<212> TYPE: PRT
<213> ORGANISM: Solanum lycopersicum

<400> SEQUENCE: 31

Met Thr Thr Thr Ser Val Leu Ser Ser Gly Phe Asn His Ser Thr Leu
1               5                   10                  15

Pro Gln Ser Tyr Val Arg Pro Glu Ser Gln Arg Pro Cys Met Ser Glu
            20                  25                  30

Val Val Asp Ser Asp Asp Leu Val Pro Val Ile Asp Met Ser Cys Thr
        35                  40                  45
```

Asn Arg Asn Val Ile Val His Gln Ile Gly Glu Ala Cys Arg Leu Tyr
            50                  55                  60

Gly Phe Phe Gln Val Ile Asn His Gly Val Ser Lys Lys Val Ile Asp
65                  70                  75                  80

Glu Met Leu Gly Val Ser His Glu Phe Phe Lys Leu Pro Val Glu Glu
                            85                  90                  95

Lys Met Lys Leu Tyr Ser Asp Asp Pro Ser Lys Thr Met Arg Leu Ser
                100                 105                 110

Thr Ser Phe Asn Val Lys Lys Glu Ala Val His Asn Trp Arg Asp Tyr
                115                 120                 125

Leu Arg Leu His Cys Tyr Pro Leu Asp Lys Tyr Ala Pro Glu Trp Pro
            130                 135                 140

Ser Asn Pro Pro Ser Phe Arg Glu Ile Val Ser Lys Tyr Cys Met Glu
145                 150                 155                 160

Val Arg Glu Leu Gly Tyr Arg Leu Glu Glu Ala Ile Ser Glu Ser Leu
                            165                 170                 175

Gly Leu Glu Lys Asp Cys Ile Lys Asn Val Leu Gly Glu Gln Gly Gln
                180                 185                 190

His Met Ala Ile Asn Phe Tyr Pro Gln Cys Pro Gln Pro Glu Leu Thr
            195                 200                 205

Tyr Gly Leu Pro Ala His Thr Asp Pro Asn Ala Ile Thr Ile Leu Leu
210                 215                 220

Gln Asp Leu Gln Val Ala Gly Leu Gln Val Leu Lys Asp Gly Lys Trp
225                 230                 235                 240

Leu Ser Ile Lys Pro Gln Pro Asn Ala Phe Val Ile Asn Leu Gly Asp
                245                 250                 255

Gln Leu Glu Ala Leu Ser Asn Gly Lys Tyr Lys Ser Ile Trp His Arg
                260                 265                 270

Ala Ile Val Asn Ser Asp Lys Ala Arg Met Ser Val Ala Ser Phe Leu
            275                 280                 285

Cys Pro Asn Asp Cys Ser Ile Ile Ser Ala Pro Lys Thr Leu Thr Glu
290                 295                 300

Asp Gly Ser Ser Ala Ile Tyr Arg His Phe Thr Tyr Ala Glu Tyr Tyr
305                 310                 315                 320

Glu Lys Phe Trp Ser Arg Asn Leu Asp Gln Glu Tyr Cys Leu Glu Leu
                325                 330                 335

Phe Lys Asn Asp Gly Thr
            340

<210> SEQ ID NO 32
<211> LENGTH: 26
<212> TYPE: DNA
<213> ORGANISM: Artificial
<220> FEATURE:
<223> OTHER INFORMATION: Primer

<400> SEQUENCE: 32
actagtatgg caacttctgc aatatc                                        26

<210> SEQ ID NO 33
<211> LENGTH: 26
<212> TYPE: DNA
<213> ORGANISM: Artificial
<220> FEATURE:
<223> OTHER INFORMATION: Primer

<400> SEQUENCE: 33
ctgcagttag gttgttggag ctttga                                              26

<210> SEQ ID NO 34
<211> LENGTH: 22
<212> TYPE: DNA
<213> ORGANISM: Artificial
<220> FEATURE:
<223> OTHER INFORMATION: Primer

<400> SEQUENCE: 34
tggttcacgt agtgggccat cg                                                  22

<210> SEQ ID NO 35
<211> LENGTH: 29
<212> TYPE: DNA
<213> ORGANISM: Artificial
<220> FEATURE:
<223> OTHER INFORMATION: Primer

<400> SEQUENCE: 35
aacggatcca tggcaacttc tgcaatatc                                           29

<210> SEQ ID NO 36
<211> LENGTH: 29
<212> TYPE: DNA
<213> ORGANISM: Artificial
<220> FEATURE:
<223> OTHER INFORMATION: Primer

<400> SEQUENCE: 36
ggcaagcttt taggttgttg gagctttga                                           29

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
cgtaaagcat caacgaaacg                                                     20

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
tcatgtaccc aaactaacca                                                     20

<210> SEQ ID NO 39
<211> LENGTH: 18
<212> TYPE: DNA
<213> ORGANISM: Artificial
<220> FEATURE:
<223> OTHER INFORMATION: Primer

<400> SEQUENCE: 39
cagctgcgga tgttgttg                                                       18

<210> SEQ ID NO 40
<211> LENGTH: 19
<212> TYPE: DNA

```
<213> ORGANISM: Artificial
<220> FEATURE:
<223> OTHER INFORMATION: Primer

<400> SEQUENCE: 40
ccactttctc cccattttg                                               19

<210> SEQ ID NO 41
<211> LENGTH: 18
<212> TYPE: DNA
<213> ORGANISM: Artificial
<220> FEATURE:
<223> OTHER INFORMATION: Primer

<400> SEQUENCE: 41
gcaaccaaag gagccatg                                                18

<210> SEQ ID NO 42
<211> LENGTH: 19
<212> TYPE: DNA
<213> ORGANISM: Artificial
<220> FEATURE:
<223> OTHER INFORMATION: Primer

<400> SEQUENCE: 42
gtttggccaa ctagtctgc                                               19

<210> SEQ ID NO 43
<211> LENGTH: 22
<212> TYPE: DNA
<213> ORGANISM: Artificial
<220> FEATURE:
<223> OTHER INFORMATION: Primer

<400> SEQUENCE: 43
ggatagaaga tgaatacaag cc                                           22

<210> SEQ ID NO 44
<211> LENGTH: 21
<212> TYPE: DNA
<213> ORGANISM: Artificial
<220> FEATURE:
<223> OTHER INFORMATION: Primer

<400> SEQUENCE: 44
acctaaggtt caggtatctg t                                            21

<210> SEQ ID NO 45
<211> LENGTH: 21
<212> TYPE: DNA
<213> ORGANISM: Artificial
<220> FEATURE:
<223> OTHER INFORMATION: Primer

<400> SEQUENCE: 45
atggacgatt gtcgattcga g                                            21

<210> SEQ ID NO 46
<211> LENGTH: 21
<212> TYPE: DNA
<213> ORGANISM: Artificial
<220> FEATURE:
<223> OTHER INFORMATION: Primer

<400> SEQUENCE: 46
ctaagtctcc attgcgtcac t                                            21
```

-continued

```
<210> SEQ ID NO 47
<211> LENGTH: 23
<212> TYPE: DNA
<213> ORGANISM: Artificial
<220> FEATURE:
<223> OTHER INFORMATION: Primer

<400> SEQUENCE: 47
tggctattct cgattttttaa tcg                                             23

<210> SEQ ID NO 48
<211> LENGTH: 19
<212> TYPE: DNA
<213> ORGANISM: Artificial
<220> FEATURE:
<223> OTHER INFORMATION: Primer

<400> SEQUENCE: 48
ccattgcacg tgttcgcag                                                   19

<210> SEQ ID NO 49
<211> LENGTH: 357
<212> TYPE: PRT
<213> ORGANISM: artificial
<220> FEATURE:
<223> OTHER INFORMATION: F3H sequence

<400> SEQUENCE: 49

Met Ala Pro Gly Thr Leu Thr Glu Leu Ala Gly Glu Ser Lys Leu Asn
1               5                   10                  15

Ser Lys Phe Val Arg Asp Glu Asp Glu Arg Pro Lys Val Ala Tyr Asn
            20                  25                  30

Val Phe Ser Asp Glu Ile Pro Val Ile Ser Leu Ala Gly Ile Asp Asp
        35                  40                  45

Val Asp Gly Lys Arg Gly Glu Ile Cys Arg Gln Ile Val Glu Ala Cys
    50                  55                  60

Glu Asn Trp Gly Ile Phe Gln Val Val Asp His Gly Val Asp Thr Asn
65                  70                  75                  80

Leu Val Ala Asp Met Thr Arg Leu Ala Arg Asp Phe Phe Ala Leu Pro
                85                  90                  95

Pro Glu Asp Lys Leu Arg Phe Asp Met Ser Gly Gly Lys Lys Gly Gly
            100                 105                 110

Phe Ile Val Ser Ser His Leu Gln Gly Glu Ala Val Gln Asp Trp Arg
        115                 120                 125

Glu Ile Val Thr Tyr Phe Ser Tyr Pro Val Arg Asn Arg Asp Tyr Ser
    130                 135                 140

Arg Trp Pro Asp Lys Pro Glu Gly Trp Val Lys Val Thr Glu Glu Tyr
145                 150                 155                 160

Ser Glu Arg Leu Met Ser Leu Ala Cys Lys Leu Leu Glu Val Leu Ser
                165                 170                 175

Glu Ala Met Gly Leu Glu Lys Glu Ser Leu Thr Asn Ala Cys Val Asp
            180                 185                 190

Met Asp Gln Lys Ile Val Val Asn Tyr Tyr Pro Lys Cys Pro Gln Pro
        195                 200                 205

Asp Leu Thr Leu Gly Leu Lys Arg His Thr Asp Pro Gly Thr Ile Thr
    210                 215                 220

Leu Leu Leu Gln Asp Gln Val Gly Gly Leu Gln Ala Thr Arg Asp Asn
225                 230                 235                 240
```

-continued

```
Gly Lys Thr Trp Ile Thr Val Gln Pro Val Glu Gly Ala Phe Val Val
                245                 250                 255

Asn Leu Gly Asp His Gly His Phe Leu Ser Asn Gly Arg Phe Lys Asn
            260                 265                 270

Ala Asp His Gln Ala Val Val Asn Ser Asn Ser Ser Arg Leu Ser Ile
        275                 280                 285

Ala Thr Phe Gln Asn Pro Ala Pro Asp Ala Thr Val Tyr Pro Leu Lys
    290                 295                 300

Val Arg Glu Gly Glu Lys Ala Ile Leu Glu Glu Pro Ile Thr Phe Ala
305                 310                 315                 320

Glu Met Tyr Lys Arg Lys Met Gly Arg Asp Leu Glu Leu Ala Arg Leu
                325                 330                 335

Lys Lys Leu Ala Lys Glu Glu Arg Asp His Lys Glu Val Asp Lys Pro
            340                 345                 350

Val Asp Gln Ile Phe
            355
```